(12) United States Patent
Chin et al.

(10) Patent No.: US 11,096,998 B2
(45) Date of Patent: Aug. 24, 2021

(54) CHIMERIC ANTIGEN RECEPTORS COMPRISING BCMA-SPECIFIC FIBRONECTIN TYPE III DOMAINS AND USES THEREOF

(71) Applicant: Janssen Biotech, Inc., Horsham, PA (US)

(72) Inventors: Chen Ni Chin, Devon, PA (US); John Lee, North Wales, PA (US); Timothy McCabe, Doylestown, PA (US); Jill Mooney, San Diego, CA (US); Michael Naso, Swarthmore, PA (US); William Strohl, Bridgewater, NJ (US)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

(21) Appl. No.: 16/323,121

(22) PCT Filed: Sep. 11, 2017

(86) PCT No.: PCT/US2017/050888
§ 371 (c)(1),
(2) Date: Feb. 4, 2019

(87) PCT Pub. No.: WO2018/052828
PCT Pub. Date: Mar. 22, 2018

(65) Prior Publication Data
US 2019/0330361 A1  Oct. 31, 2019

Related U.S. Application Data

(60) Provisional application No. 62/394,329, filed on Sep. 14, 2016.

(51) Int. Cl.
| | | |
|---|---|---|
| *C07K 16/00* | (2006.01) | |
| *C07K 16/46* | (2006.01) | |
| *C07K 16/28* | (2006.01) | |
| *A61K 39/00* | (2006.01) | |
| *C12N 15/82* | (2006.01) | |
| *A61P 35/00* | (2006.01) | |
| *C07K 14/525* | (2006.01) | |
| *C07K 14/705* | (2006.01) | |
| *C07K 14/75* | (2006.01) | |
| *C07K 14/78* | (2006.01) | |

(52) U.S. Cl.
CPC .......... *A61K 39/0011* (2013.01); *A61P 35/00* (2018.01); *C07K 14/525* (2013.01); *C07K 14/705* (2013.01); *C07K 14/75* (2013.01); *C07K 14/78* (2013.01); *C07K 16/2878* (2013.01); *C12N 15/8257* (2013.01); *A61K 2039/5158* (2013.01); *C07K 2317/24* (2013.01); *C07K 2317/50* (2013.01); *C07K 2317/622* (2013.01); *C07K 2319/03* (2013.01); *C07K 2319/033* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,223,409 A | 6/1993 | Ladner et al. |
| 5,643,768 A | 7/1997 | Kawasaki |
| 5,827,642 A | 10/1998 | Riddell et al. |
| 5,858,358 A | 1/1999 | June et al. |
| 5,883,223 A | 3/1999 | Gray |
| 6,040,177 A | 3/2000 | Riddell et al. |
| 6,172,197 B1 | 1/2001 | McCafferty et al. |
| 6,352,694 B1 | 3/2002 | June et al. |
| 6,472,147 B1 | 10/2002 | Janda et al. |
| 6,534,055 B1 | 3/2003 | June et al. |
| 6,582,915 B1 | 6/2003 | Griffiths et al. |
| 6,673,901 B2 | 1/2004 | Koide |

(Continued)

FOREIGN PATENT DOCUMENTS

| | | |
|---|---|---|
| WO | WO 87/00195 A1 | 1/1987 |
| WO | WO 90/03430 A1 | 4/1990 |

(Continued)

OTHER PUBLICATIONS

Jacobs et al. Design of novel FN3 domains with high stability by a consensus sequence approach. Protein Engineering, Design & Selection vol. 25 No. 3 pp. 107-117, 2012. (Year: 2012).*
Maus et al., "Antibody-modified T cells: CARs take the front seat for hematologic malignancies" Blood. Apr. 24, 2014;123(17):2625-35.
Curran and Brentjens, "Chimeric Antigen Receptor T Cells for Cancer Immunotherapy", Journal of Clinical Oncology, May 20, 2015; 33(15):1703-6.
Dai et al., "Chimeric Antigen Receptors Modified T-Cells for Cancer Therapy" J Natl Cancer Inst. Jan. 27, 2016;108(7).

(Continued)

*Primary Examiner* — Maher M Haddad
(74) *Attorney, Agent, or Firm* — Jones Day

(57) ABSTRACT

BCMA-specific fibronectin type III (FN3) domains, BCMA-targeting chimeric antigen receptors (CARs) comprising the FN3 domains, and engineered BCMA-targeting immune cells expressing the CARs are described. Also described are nucleic acids and expression vectors encoding the FN3 domains and the CARs, recombinant cells containing the vectors, and compositions comprising the engineered immune cells. Methods of making the FN3 domains, CARs, and engineered immune cells, and methods of using the engineered immune cells to treat diseases including cancer are also described.

2 Claims, 7 Drawing Sheets
Specification includes a Sequence Listing.

(56) References Cited

U.S. PATENT DOCUMENTS

| | | | |
|---|---|---|---|
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 6,969,108 | B2 | 11/2005 | Fukumoto et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 7,842,476 | B2 | 11/2010 | McGregor et al. |
| 8,278,419 | B2 | 10/2012 | Jacobs et al. |
| 9,200,273 | B2 | 12/2015 | Diem et al. |
| 2006/0121005 | A1 | 6/2006 | Berenson et al. |
| 2010/0216708 | A1 | 8/2010 | Jacobs et al. |
| 2011/0118144 | A1 | 5/2011 | Hyun et al. |
| 2011/0274623 | A1 | 11/2011 | Jacobs |
| 2013/0096019 | A1* | 4/2013 | Jacobs .................. C07K 14/78 506/9 |
| 2013/0226834 | A1 | 8/2013 | Gannalo |

FOREIGN PATENT DOCUMENTS

| | | | | |
|---|---|---|---|---|
| WO | WO 2009/085462 | A1 | 7/2009 | |
| WO | WO-2011140086 | A2 * | 11/2011 | ........... C07K 14/575 |
| WO | WO 2012129514 | A1 | 9/2012 | |
| WO | WO 2013049275 | A1 | 4/2013 | |
| WO | WO 2013/176915 | A1 | 11/2013 | |
| WO | WO 2013/176916 | A1 | 11/2013 | |
| WO | WO 2014/039523 | A1 | 3/2014 | |
| WO | WO 2014/130635 | A1 | 8/2014 | |
| WO | WO 2014/184143 | A1 | 11/2014 | |
| WO | WO 2014/184741 | A1 | 11/2014 | |
| WO | WO 2014/184744 | A1 | 11/2014 | |
| WO | WO 2014/191128 | A1 | 12/2014 | |
| WO | WO 2016014565 | A2 | 1/2016 | |

OTHER PUBLICATIONS

Naymagon and Abdul-Hay, "Novel agents in the treatment of multiple myeloma: a review about the future", Journal of Hematology and Oncology Jun. 30, 2016;9(1):52.
Coquery and Erickson, "Regulatory Roles of the Tumor Necrosis Factor Receptor BCMA", Critical Reviews in Immunology 2012;32(4):287-305.
Novak et al., "Expression of BCMA, TACI, and BAFF-R in multiple myeloma: a mechanism for growth and survival", Blood. Jan. 15, 2004;103(2): 689-94.
Neri et al., "Neutralizing B-Cell ∧ Activating Factor Antibody Improves Survival and Inhibits Osteoclastogenesis in a Severe Combined Immunodeficient Human Multiple Myeloma Model", Clin Cancer Res. Oct. 1, 2007;13(19):5903-9.
Bellucci et al., "Graft-versus-tumor response in patients with multiple myeloma is associated with antibody response to BCMA, a plasma-cell membrane receptor", Blood. May 15, 2005;105(10):3945-50.
Moreaux et al., "BAFF and APRIL protect myeloma cells from apoptosis induced by interleukin 6 deprivation and dexamethasone", Blood. Apr. 15, 2004;103(8):3148-57.
Bork and Doolittle, "Proposed acquisition of an animal protein domain by bacteria", PNAS USA 89:8990-8994, 1992.
Meinke et al.,"Cellulose-Binding Polypeptides from *Cellulomonas fimi*: Engoglucanase D (CenD), a Family A β-1,4-Glucanase", Journal of Bacteriology 175:1910-1918, 1993.
Watanabe et al., "Gene Cloning of Chitinase A1 from *Bacillus circulans* WL-12 Revealed Its Evolutionary Relationship to *Serratia chitinase* and to the Type III homology Units of Fibronectin", J Biol Chem 265:15659-15665, 1990.
GenBank Accession No. NP_001183.2, "tumor necrosis factor receptor superfamily member 17 [*Homo sapiens*]".
Jacobs et al., "Design of novel FN3 domains with high stability by a consensus sequence approach", Protein Engineering, Design, and Selection, 25:107-117, 2012.
Hanes and Pluckthun, "In vitro selection and evolution of functional proteins by using ribosome display", PNAS USA, 94, 4937-4942, 1997.
Roberts and Szostak, "RNA-peptide fusions for the in vitro selection of peptides and proteins", PNAS USA, 94, 12297-12302, 1997.
Odegrip et al., "CIS display: in vitro selection of peptides from libraries of protein—DNA complexes", PNAS USA 101, 2806-2810, 2004.
Lehmann and Wyss, "Engineering proteins for thermostability: the use of sequence alignments versus rational design and directed evolution", Curr Opin Biotechnol, 12, 371-375, 2001.
Patel et al., "Impact of chimeric immune receptor extracellular protein domains on T cell function" Gene Therapy, 1999; 6: 412-419.
Mayfield et al., "Expression and assembly of a fully active antibody in algae", PNAS U.S.A. 2003 100(2):438-42.
Sinclair et al. "Synonymous codon usage bias and the expression of human glucocerebrosidase in the methylotrophic yeast, *Pichia pastoris*", Protein Expr Purif. 2002 (1):96-105.
Connell, N., "Expression systems for use in actinomycetes and related organisms", Curr Opin Biotechnol. 2001 (5):446-9.
Makrides et al. "Strategies for Achieving High-Level Expression of Genes in *Escherichia coli*" Microbiol Rev. 1996 60(3):512-38.
Sharp et al. "Synonymous Codon Usage in *Saccharomyces cerevisiae*", Yeast. 1991 7(7):657-78.
Luckow and Summers, "Trends in the Development of Baculovirus Expression Vectors", Bio/Technology, 6:47, 1988.
Ham et al, "Media and Growth Requirement", Methods in Enzymology 58:44 1979.
Barnes et al, Methods for Growth of Cultured Cells in Serum-Free Medium, Analytical Biochemistry, 102:255 (1980).
Garfall et al., "Immunotherapy with Chimeric Antigen Receptors for Multiple Myeloma" Discovery Medicine, 2014, 17(91):37-46.
Takebe et al., "Generation of Dual Resistance to 4-Hydroperoxycyclophosphamide and Methotrexate by Retroviral Transfer of the Human Aldehyde Dehydrogenase Class 1 Gene and a Mutated Dihydrofolate Reductase Gene" Molecular Therapy Jan. 2001;3(1):88-96.
Sugimoto et al, Drug-selected co-expression of P-glycoprotein and gp91 in vivo from a $MDR_1$ bicistronic retrovirus vector Ha-MDR-IRES-gp91J Gene Med. May 2003;5(5):366-76.
Zielske et al., "In vivo selection of MGMT(P140K) lentivirus-transduced human NOD/SCID repopulating cells without pretransplant irradiation conditioning" J Clin Invest. Nov. 2003;112(10):1561-70.
Nivens et al, "Engineered resistance to camptothecin and antifolates by retroviral coexpression of tyrosyl DNA phosphodiesterase-I and thymidylate synthase", Cancer Chemother Pharmacol. Feb. 2004;53(2):107-15.
Bardenheuer et al., "Resistance to cytarabine and gemcitabine and in vitro selection of transduced cells after retroviral expression of cytidine deaminase in human hematopoietic progenitor cells", Leukemia. Dec. 2005;19(12):2281-8.
Kushman et al., Expression of human glutathione S-transferase P1 confers resistance to benzo[a]pyrene or benzo[a]pyrene-7,8-dihydrodiol mutagenesis,macromolecular alkylation and formation of stable N2-Gua-BPDEadducts in stably transfected V79MZ cells co-expressing hCYP1A1Carcinogenesis. Jan. 2007;28(1):207-14.
Birtalan et al., "The Intrinsic Contributions of Tyrosine, Serine, Glycine and Arginine to the Affinity and Specificity of Antibodies", J Mol Biol. Apr. 11, 2008;377(5):1518-28.
Hammill et al., 2015, "Designed ankyrin repeat proteins are effective targeting elements for chimeric antigen receptors," J Immunother Cancer, 3:55 (11 pages).
Hermanson et al., 2016, "A Novel Bcma-Specific, Centyrin-Based Car-T Product for the Treatment of Multiple Myeloma," Blood Journal, 128(22):2127 (5 pages).

(56) References Cited

OTHER PUBLICATIONS

Kuznetsova, 2016, "Chimeric antigen receptors using alternative targeting modules," Current Issues of Experimental and Clinical Oncology, pp. 110-112, in Russian English abstract.
International Search Report and Written Opinion for International Patent Application No. PCT/US2017/050888 (Pub. No. WO 2018052828) dated Dec. 4, 2017 (11 pages).
GenBank Accession No. NM_001192.2, "Homo sapiens TNF receptor superfamily member 17 (TNFRSF17), mRNA," Nov. 10, 2018.

* cited by examiner

SEQUENCE LISTING

<160> NUMBER OF SEQ ID NOS: 145

<210> SEQ ID NO 1

```
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85

<210> SEQ ID NO 2
<211> LENGTH: 21
<212> TYPE: PRT
<213> ORGANISM: Homo sapiens

<400> SEQUENCE: 2

Met Ala Leu Pro Val Thr Ala Leu Leu Leu Pro Leu Ala Leu Leu Leu
1               5                   10                  15

His Ala Ala Arg Pro
            20

<210> SEQ ID NO 3
<211> LENGTH: 47
<212> TYPE: PRT
<213> ORGANISM: Homo sapiens

<400> SEQUENCE: 3

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 4
<211> LENGTH: 23
<212> TYPE: PRT
<213> ORGANISM: Homo sapiens

<400> SEQUENCE: 4

Ile Trp Ala Pro Leu Ala Gly Thr Cys Gly Val Leu Leu Leu Ser Leu
1               5                   10                  15

Val Ile Thr Leu Tyr Cys Lys
            20

<210> SEQ ID NO 5
<211> LENGTH: 41
<212> TYPE: PRT
<213> ORGANISM: Homo sapiens
```

```
<400> SEQUENCE: 5

Arg Gly Arg Lys Lys Leu Leu Tyr Ile Phe Lys Gln Pro Phe Met Arg
1               5                   10                  15

Pro Val Gln Thr Thr Gln Glu Asp Gly Cys Ser Cys Arg Phe Pro
            20                  25                  30

Glu Glu Glu Glu Gly Gly Cys Glu Leu
            35                  40

<210> SEQ ID NO 6
<211> LENGTH: 112
<212> TYPE: PRT
<213> ORGANISM: Homo sapiens

<400> SEQUENCE: 6

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 7
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (12)..(12)
<223> OTHER INFORMATION: /replace="Arg" or "His"
<220> FEATURE:
<221> NAME/KEY: VARIANT
<222> LOCATION: (13)..(13)
<223> OTHER INFORMATION: /replace="Ile"
<220> FEATURE:
<221> NAME/KEY: VARIANT
<222> LOCATION: (23)..(23)
<223> OTHER INFORMATION: /replace="Ile"
<220> FEATURE:
<221> NAME/KEY: VARIANT
<222> LOCATION: (33)..(33)
<223> OTHER INFORMATION: /replace="Ile" or "Thr" or "Trp" or "Arg" or
      "Pro"
<220> FEATURE:
<221> NAME/KEY: VARIANT
<222> LOCATION: (35)..(35)
<223> OTHER INFORMATION: /replace="Val" or "Lys" or "Arg"
<220> FEATURE:
<221> NAME/KEY: VARIANT
<222> LOCATION: (37)..(37)
<223> OTHER INFORMATION: /replace="Arg" or "Ile" or "Val"
<220> FEATURE:
<221> NAME/KEY: VARIANT
<222> LOCATION: (39)..(39)
<223> OTHER INFORMATION: /replace="Pro" or "Asn" or "Arg" or "Val" or
      "Thr"
```

```
<220> FEATURE:
<221> NAME/KEY: VARIANT
<222> LOCATION: (40)..(40)
<223> OTHER INFORMATION: /replace="Ile" or "Ala" or "Leu"
<220> FEATURE:
<221> NAME/KEY: VARIANT
<222> LOCATION: (41)..(41)
<223> OTHER INFORMATION: /replace="Glu" or "Thr" or "Ala" or "Ile"
<220> FEATURE:
<221> NAME/KEY: VARIANT
<222> LOCATION: (42)..(42)
<223> OTHER INFORMATION: /replace="Thr" or "Trp"
<220> FEATURE:
<221> NAME/KEY: VARIANT
<222> LOCATION: (47)..(47)
<223> OTHER INFORMATION: /replace="Trp" or "His"
<220> FEATURE:
<221> NAME/KEY: VARIANT
<222> LOCATION: (49)..(49)
<223> OTHER INFORMATION: /replace="Asn" or "His" or "Val" or "Asp" or
      "Tyr"
<220> FEATURE:
<221> NAME/KEY: VARIANT
<222> LOCATION: (61)..(61)
<223> OTHER INFORMATION: /replace="Asp"
<220> FEATURE:
<221> NAME/KEY: VARIANT
<222> LOCATION: (69)..(69)
<223> OTHER INFORMATION: /replace="Tyr" or "Val" or "Thr" or "Ala"
<220> FEATURE:
<221> NAME/KEY: VARIANT
<222> LOCATION: (71)..(71)
<223> OTHER INFORMATION: /replace="Arg" or "Gln" or "Leu" or "Val"
<220> FEATURE:
<221> NAME/KEY: VARIANT
<222> LOCATION: (73)..(73)
<223> OTHER INFORMATION: /replace="Ala" or "Asn" or "Ser" or "Asp" or
      "Thr"
<220> FEATURE:
<221> NAME/KEY: VARIANT
<222> LOCATION: (79)..(79)
<223> OTHER INFORMATION: /replace="Asp" or "Asn" or "Pro" or "Trp" or
      "Lys" or "Arg" or "Glu" or "Gly"
<220> FEATURE:
<221> NAME/KEY: VARIANT
<222> LOCATION: (80)..(80)
<223> OTHER INFORMATION: /replace="Ile" or "Glu" or "Thr" or "Ser" or
      "His" or "Arg"
<220> FEATURE:
<221> NAME/KEY: VARIANT
<222> LOCATION: (82)..(82)
<223> OTHER INFORMATION: /replace="Arg" or "Phe" or "Trp" or "Ile" or
      "Ser" or "Tyr" or "Lys" or "Gln"
<220> FEATURE:
<221> NAME/KEY: VARIANT
<222> LOCATION: (85)..(85)
<223> OTHER INFORMATION: /replace="Val" or "Ile"
<220> FEATURE:
<221> NAME/KEY: VARIANT
<222> LOCATION: (87)..(87)
<223> OTHER INFORMATION: /replace="His" or "Pro" or "Thr" or "Ala" or
      "Ser"
<220> FEATURE:
<221> NAME/KEY: MISC_FEATURE
<222> LOCATION: (1)..(90)
<223> OTHER INFORMATION: /note="Variant residues given in the sequence
      have no preference with respect to those in the annotations for
      variant positions"

<400> SEQUENCE: 7

Met Leu Pro Ala Pro Lys Asn Leu Val Val Ser Glu Val Thr Glu Asp
1               5                   10                  15

Ser Ala Arg Leu Ser Trp Thr Ala Pro Asp Ala Ala Phe Asp Ser Phe
            20                  25                  30

Val Ile Gly Tyr Ser Glu Gln Asp Val Cys Gly Glu Ala Ile Val Leu
        35                  40                  45
```

-continued

Thr Val Pro Gly Ser Glu Arg Ser Tyr Asp Leu Thr Gly Leu Lys Pro
            50                  55                  60

Gly Thr Glu Tyr Trp Val Ile Ile Arg Gly Val Lys Gly Gly Ser Phe
65                  70                  75                  80

Ser Glu Pro Leu Ser Ala Ile Phe Thr Thr
                85                  90

<210> SEQ ID NO 8
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
        35                  40                  45

Asp Val Pro Gly Ser Glu Arg Ser Tyr Asp Leu Thr Gly Leu Lys Pro
    50                  55                  60

Gly Thr Glu Tyr Thr Val Val Ile Asp Gly Val Lys Gly Gly Gly Arg
65                  70                  75                  80

Ser Gln Pro Leu Val Ala Thr Phe Thr Thr
                85                  90

<210> SEQ ID NO 9
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Val Tyr Ser Glu Pro Asp Val Cys Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Arg Ile Ala Gly Val Lys Gly Gly Asp Phe
65                  70                  75                  80

Ser Arg Pro Leu Ser Ala Ile Phe Thr Thr
                85                  90

<210> SEQ ID NO 10
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met Leu Pro Ala Pro Lys Asn Leu Val Val Ser Arg Val Thr Glu Asp
1               5                   10                  15

Ser Ala Arg Leu Ser Trp Ile Ala Pro Asp Ala Ala Phe Asp Ser Phe
            20                  25                  30

Ile Ile Val Tyr Arg Glu Asn Ile Glu Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Gln Ile Ala Gly Val Lys Gly Gly Asn Ile
65                  70                  75                  80

Ser Phe Pro Leu Ser Ala Ile Phe Thr Thr
                85                  90

<210> SEQ ID NO 11
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
        35                  40                  45

Asp Val Pro Gly Ser Glu Arg Ser Tyr Asp Leu Thr Gly Leu Lys Pro
    50                  55                  60

Gly Thr Glu Tyr Val Val Val Ile Asp Gly Val Lys Gly Gly Asp His
65                  70                  75                  80

Ser Lys Pro Leu Val Ala Thr Phe Thr Thr
                85                  90

<210> SEQ ID NO 12
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
        35                  40                  45

Tyr Val Pro Gly Ser Glu Arg Ser Tyr Asp Leu Thr Gly Leu Lys Pro
    50                  55                  60

Gly Thr Glu Tyr Thr Val Val Ile Ser Gly Val Lys Gly Gly Glu Ser
65                  70                  75                  80

Ser Tyr Pro Leu Ile Ala Ala Phe Thr Thr

```
                    85                  90

<210> SEQ ID NO 13
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Met Leu Pro Ala Pro Lys Asn Leu Val Val Ser His Val Thr Glu Asp
1               5                  10                  15

Ser Ala Arg Leu Ser Trp Thr Ala Pro Asp Ala Ala Phe Asp Ser Phe
            20                  25                  30

Ile Ile Val Tyr Arg Glu Asn Ile Glu Thr Gly Glu Ala Ile Val Leu
        35                  40                  45

Thr Val Pro Gly Ser Glu Arg Ser Tyr Asp Leu Thr Asp Leu Lys Pro
    50                  55                  60

Gly Thr Glu Tyr Tyr Val Gln Ile Ala Gly Val Lys Gly Gly Asn Ile
65                  70                  75                  80

Ser Phe Pro Leu Ser Ala Ile Phe Thr Thr
                85                  90

<210> SEQ ID NO 14
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Met Leu Pro Ala Pro Lys Asn Leu Val Val Ser Arg Ile Thr Glu Asp
1               5                  10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
        35                  40                  45

Asp Val Pro Gly Ser Glu Arg Ser Tyr Asp Leu Thr Gly Leu Lys Pro
    50                  55                  60

Gly Thr Glu Tyr Ala Val Val Ile Thr Gly Val Lys Gly Gly Arg Phe
65                  70                  75                  80

Ser Ser Pro Leu Val Ala Ser Phe Thr Thr
                85                  90

<210> SEQ ID NO 15
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Met Leu Pro Ala Pro Lys Asn Leu Val Val Ser Arg Val Thr Glu Asp
1               5                  10                  15

Ser Ala Arg Leu Ser Trp Thr Ala Pro Asp Ala Ala Phe Asp Ser Phe
            20                  25                  30
```

Ile Ile Val Tyr Arg Glu Asn Ile Glu Thr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Tyr Val Gln Ile Ala Gly Val Lys Gly Gly Asn Ile
65                  70                  75                  80

Ser Phe Pro Leu Ser Ala Ile Phe Thr Thr
                85                  90

<210> SEQ ID NO 16
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Trp Ile Arg Tyr Val Glu Arg Leu Val Trp Gly Glu Ala Ile His Leu
            35                  40                  45

His Val Pro Gly Ser Glu Arg Ser Tyr Asp Leu Thr Gly Leu Lys Pro
        50                  55                  60

Gly Thr Glu Tyr Val Val Ile Ser Gly Val Lys Gly Gly Trp Glu
65                  70                  75                  80

Ser Thr Pro Leu Val Ala Pro Phe Thr Thr
                85                  90

<210> SEQ ID NO 17
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
            35                  40                  45

Tyr Val Pro Gly Ser Glu Arg Ser Tyr Asp Leu Thr Gly Leu Lys Pro
        50                  55                  60

Gly Thr Glu Tyr Thr Val Val Ile Asp Gly Val Lys Gly Gly Gly Arg
65                  70                  75                  80

Ser Gln Pro Leu Val Ala Ser Phe Thr Thr
                85                  90

<210> SEQ ID NO 18
<211> LENGTH: 90
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 18

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Arg Ile Arg Tyr Val Glu Val Ile Ala Trp Gly Glu Ala Ile Trp Leu
        35                  40                  45

Val Val Pro Gly Ser Glu Arg Ser Tyr Asp Leu Thr Gly Leu Lys Pro
    50                  55                  60

Gly Thr Glu Tyr Val Val Ile Asp Gly Val Lys Gly Gly Lys Thr
65                  70                  75                  80

Ser Ile Pro Leu Ile Ala His Phe Thr Thr
                85                  90
```

<210> SEQ ID NO 19
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Thr Ile Lys Tyr Ile Glu Arg Ala Thr Trp Gly Glu Ala Ile Trp Leu
        35                  40                  45

Asn Val Pro Gly Ser Glu Arg Ser Tyr Asp Leu Thr Gly Leu Lys Pro
    50                  55                  60

Gly Thr Glu Tyr Val Val Leu Ile Asn Gly Val Lys Gly Gly Pro Glu
65                  70                  75                  80

Ser Trp Pro Leu Ile Ala His Phe Thr Thr
                85                  90
```

<210> SEQ ID NO 20
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Val Tyr Ser Glu Pro Asp Val Cys Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Arg Ile Pro Gly Val Lys Gly Gly Asp Phe
```

Phe His Pro Leu Ser Ala Ile Phe Thr Thr
            85                  90

<210> SEQ ID NO 21
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Met Leu Pro Ala Pro Lys Asn Leu Val Val Ser Arg Ile Thr Glu Asp
1               5                   10                  15

Ser Val Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
        35                  40                  45

Asp Val Pro Gly Ser Glu Arg Ser Tyr Asp Leu Thr Gly Leu Lys Pro
    50                  55                  60

Gly Thr Glu Tyr Val Val Ser Ile Asp Gly Val Lys Gly Gly Asp His
65                  70                  75                  80

Ser Lys Pro Leu Val Ala Thr Phe Thr Thr
            85                  90

<210> SEQ ID NO 22
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Val Tyr Ser Glu Pro Asp Val Cys Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Arg Ile Pro Gly Val Lys Gly Gly Asp Phe
65                  70                  75                  80

Ser Gln Pro Leu Ser Ala Ile Phe Thr Thr
            85                  90

<210> SEQ ID NO 23
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Met Leu Pro Ala Pro Lys Asn Leu Val Val Ser Ser Val Thr Glu Asp
1               5                   10                  15

Ser Ala Arg Leu Ser Trp Thr Ala Pro Asp Ala Ala Phe Asp Ser Phe
            20                  25                  30

Val Ile Val Tyr Ser Glu Pro Asp Val Cys Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Arg Ile Pro Gly Val Lys Gly Gly Asp Phe
65                  70                  75                  80

Ser Gln Pro Leu Ser Ala Ile Phe Thr Thr
                85                  90

<210> SEQ ID NO 24
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
        35                  40                  45

Asp Val Pro Gly Ser Glu Arg Ser Tyr Asp Leu Thr Gly Leu Lys Pro
    50                  55                  60

Gly Thr Glu Tyr Thr Val Val Ile Asp Gly Val Lys Gly Gly Gly Arg
65                  70                  75                  80

Ser Gln Pro Leu Phe Ala Gln Phe Thr Thr
                85                  90

<210> SEQ ID NO 25
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
        35                  40                  45

Asp Val Pro Gly Ser Glu Arg Ser Tyr Asp Leu Thr Gly Leu Lys Pro
    50                  55                  60

Gly Thr Glu Tyr Val Val Val Ile Ser Gly Val Lys Gly Gly Trp Glu
65                  70                  75                  80

Ser Thr Pro Leu Val Ala Pro Phe Thr Thr
                85                  90

<210> SEQ ID NO 26
<211> LENGTH: 90

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Val Glu Arg Ile Val Trp Gly Glu Ala Ile Trp Leu
            35                  40                  45

His Val Pro Gly Ser Glu Arg Ser Tyr Asp Leu Thr Gly Leu Lys Pro
    50                  55                  60

Gly Thr Glu Tyr Val Val Ile Ser Gly Val Lys Gly Gly Trp Glu
65                  70                  75                  80

Ser Thr Pro Leu Val Ala Pro Phe Thr Thr
                85                  90

<210> SEQ ID NO 27
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
            35                  40                  45

Asp Val Pro Gly Ser Glu Arg Ser Tyr Asp Leu Thr Gly Leu Lys Pro
    50                  55                  60

Gly Thr Glu Tyr Thr Val Val Ile Gly Gly Val Lys Gly Gly His Asn
65                  70                  75                  80

Ser Trp Pro Leu Ser Ala Lys Phe Thr Thr
                85                  90

<210> SEQ ID NO 28
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Trp Ile Arg Tyr Val Glu Arg Leu Val Trp Gly Glu Ala Ile His Leu
            35                  40                  45

His Val Pro Gly Ser Glu Arg Ser Tyr Asp Leu Thr Gly Leu Lys Pro
```

```
                    50                  55                  60

Gly Thr Glu Tyr Val Val Ile Ser Gly Val Lys Gly Gly Glu Gln
 65                  70                  75                  80

Ser His Pro Leu Tyr Ala Thr Phe Thr Thr
                     85                  90

<210> SEQ ID NO 29
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Pro Ile Arg Tyr Ile Glu Thr Leu Ile Trp Gly Glu Ala Ile Trp Leu
             35                  40                  45

Gln Val Pro Gly Ser Glu Arg Ser Tyr Asp Leu Thr Gly Leu Lys Pro
 50                  55                  60

Gly Thr Glu Tyr Val Val Ile Ser Gly Val Lys Gly Gly Trp Glu
 65                  70                  75                  80

Ser Lys Pro Leu Ile Ala Ala Phe Thr Thr
                     85                  90

<210> SEQ ID NO 30
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Met Leu Pro Ala Pro Lys Asn Leu Val Val Ser Arg Ile Thr Glu Asp
  1               5                  10                  15

Ser Ala Arg Leu Ser Trp Thr Ala Pro Asp Ala Ala Phe Asp Ser Phe
                 20                  25                  30

Pro Ile Arg Tyr Ile Glu Thr Leu Ile Trp Glu Glu Ala Ile Trp Leu
             35                  40                  45

Asp Val Pro Gly Ser Glu Arg Ser Tyr Asp Leu Thr Gly Leu Lys Pro
 50                  55                  60

Gly Thr Glu Tyr Thr Val Ile Asp Gly Val Lys Gly Gly Gly Arg
 65                  70                  75                  80

Ser Gln Pro Leu Val Ala Ser Phe Thr Thr
                     85                  90

<210> SEQ ID NO 31
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31
```

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
            35                  40                  45

Tyr Val Pro Gly Ser Glu Arg Ser Tyr Asp Leu Thr Gly Leu Lys Pro
        50                  55                  60

Gly Thr Glu Tyr Val Val Ile Ser Gly Val Lys Gly Gly Glu Gln
65                  70                  75                  80

Ser His Pro Leu Tyr Ala Thr Phe Thr Thr
                85                  90

<210> SEQ ID NO 32
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
            35                  40                  45

Phe Val Pro Gly Ser Glu Arg Ser Tyr Asp Leu Thr Gly Leu Lys Pro
        50                  55                  60

Gly Thr Glu Tyr Val Val Ile Ser Gly Val Lys Gly Gly Glu Gln
65                  70                  75                  80

Ser His Pro Leu Tyr Ala Thr Phe Thr Thr
                85                  90

<210> SEQ ID NO 33
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Thr Ile Lys Tyr Ile Glu Arg Ala Thr Trp Gly Glu Ala Ile Trp Leu
            35                  40                  45

Asn Val Pro Gly Ser Glu Arg Ser Tyr Asp Leu Thr Gly Leu Lys Pro
        50                  55                  60

Gly Thr Glu Tyr Val Val Leu Ile Asn Gly Val Lys Gly Gly Pro Glu
65                  70                  75                  80

Ser Trp Pro Leu Ile Ala Tyr Phe Thr Thr
                85                  90

<210> SEQ ID NO 34
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 34

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
        35                  40                  45

His Val Pro Gly Ser Glu Arg Ser Tyr Asp Leu Thr Gly Leu Lys Pro
    50                  55                  60

Gly Thr Glu Tyr Val Val Ile Ser Gly Val Lys Gly Gly Glu Gln
65                  70                  75                  80

Ser His Pro Leu Tyr Ala Thr Phe Thr Thr
                85                  90

<210> SEQ ID NO 35
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
        35                  40                  45

Asp Val Pro Gly Ser Glu Arg Ser Tyr Asp Leu Thr Gly Leu Lys Pro
    50                  55                  60

Gly Thr Glu Tyr Val Val Ile Ser Gly Val Lys Gly Gly Glu Gln
65                  70                  75                  80

Ser His Pro Leu Tyr Ala Thr Phe Thr Thr
                85                  90

<210> SEQ ID NO 36
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Lys Tyr Ile Glu Arg Ala Thr Trp Gly Glu Ala Ile Trp Leu

```
                   35                  40                  45

Asn Val Pro Gly Ser Glu Arg Ser Tyr Asp Leu Thr Gly Leu Lys Pro
                50                  55                  60

Gly Thr Glu Tyr Val Val Leu Ile Asn Gly Val Lys Gly Gly Pro Glu
65                  70                  75                  80

Ser Trp Pro Leu Trp Ala Ser Phe Thr Thr
                85                  90

<210> SEQ ID NO 37
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
                20                  25                  30

Pro Ile Arg Tyr Ile Glu Thr Leu Ile Trp Gly Glu Ala Ile Trp Leu
            35                  40                  45

Asp Val Pro Gly Ser Glu Arg Ser Tyr Asp Leu Thr Gly Leu Lys Pro
        50                  55                  60

Gly Thr Glu Tyr Val Val Ile Ser Gly Val Lys Gly Gly Glu Gln
65                  70                  75                  80

Ser His Pro Leu Tyr Ala Thr Phe Thr Thr
                85                  90

<210> SEQ ID NO 38
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
                20                  25                  30

Pro Ile Arg Tyr Ile Glu Thr Leu Ile Trp Gly Glu Ala Ile Trp Leu
            35                  40                  45

Asp Val Pro Gly Ser Glu Arg Ser Tyr Asp Leu Thr Gly Leu Lys Pro
        50                  55                  60

Ala Thr Glu Tyr Val Val Ile Thr Gly Val Lys Gly Gly Arg Lys
65                  70                  75                  80

Ser Tyr Pro Leu Val Ala Glu Phe Thr Thr
                85                  90

<210> SEQ ID NO 39
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 39

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
        35                  40                  45

Asp Val Pro Gly Ser Glu Arg Ser Tyr Asp Leu Thr Gly Leu Lys Pro
    50                  55                  60

Gly Thr Glu Tyr Leu Val Val Ile Ser Gly Val Lys Gly Gly Arg Asp
65                  70                  75                  80

Ser Gln Pro Leu Ile Thr His Phe Thr Thr
                85                  90

<210> SEQ ID NO 40
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Lys Tyr Ile Glu Arg Ala Thr Trp Gly Glu Ala Ile Trp Leu
        35                  40                  45

Asn Val Pro Gly Ser Glu Arg Ser Tyr Asp Leu Thr Gly Leu Lys Pro
    50                  55                  60

Gly Thr Glu Tyr Val Val Leu Ile Asn Gly Val Lys Gly Gly Pro Glu
65                  70                  75                  80

Ser Trp Pro Leu Ile Ala Tyr Phe Thr Thr
                85                  90

<210> SEQ ID NO 41
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Trp Ile Arg Tyr Val Glu Arg Leu Val Trp Gly Glu Ala Ile His Leu
        35                  40                  45

His Val Pro Gly Ser Glu Arg Ser Tyr Asp Leu Thr Gly Leu Lys Pro
    50                  55                  60

Gly Thr Glu Tyr Val Val Ser Ile Asp Gly Val Lys Gly Gly Asp His
65                  70                  75                  80

Ser Lys Pro Leu Val Ala Thr Phe Thr Thr
            85                  90

<210> SEQ ID NO 42
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Gln Tyr Ile Glu Arg Leu Arg Trp Gly Glu Ala Ile Thr Leu
        35                  40                  45

Gly Val Pro Gly Ser Glu Arg Ser Tyr Asp Leu Thr Gly Leu Lys Pro
    50                  55                  60

Gly Thr Glu Tyr Val Val Pro Ile Ser Gly Val Lys Gly Gly Arg Thr
65                  70                  75                  80

Ser Thr Pro Leu Ile Ala Ser Phe Thr Thr
            85                  90

<210> SEQ ID NO 43
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Met Leu Pro Ala Pro Lys Asn Leu Val Val Ser Arg Val Thr Glu Asp
1               5                   10                  15

Ser Ala Arg Leu Ser Trp Thr Thr Pro Asp Ala Ala Phe Asp Ser Phe
            20                  25                  30

Thr Ile Lys Tyr Ile Glu Arg Ala Thr Trp Gly Glu Ala Ile Trp Leu
        35                  40                  45

Asn Val Pro Gly Ser Glu Arg Ser Tyr Asp Leu Thr Gly Leu Lys Pro
    50                  55                  60

Gly Thr Glu Tyr Val Val Leu Ile Asn Gly Val Lys Gly Gly Pro Glu
65                  70                  75                  80

Ser Trp Pro Leu Ile Ala Tyr Phe Thr Thr
            85                  90

<210> SEQ ID NO 44
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe

```
                    20                  25                  30

Ile Ile Gly Tyr Ile Glu Gln Ile Val Trp Gly Glu Ala Ile His Leu
                35                  40                  45

Asn Val Pro Gly Ser Glu Arg Ser Tyr Asp Leu Thr Gly Leu Lys Pro
        50                  55                  60

Gly Thr Glu Tyr Val Val Ile Ile Arg Gly Val Lys Gly Gly Ser Phe
65                  70                  75                  80

Ser Glu Pro Leu Val Ala Pro Phe Thr Thr
                85                  90

<210> SEQ ID NO 45
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85

<210> SEQ ID NO 46
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (32)..(32)
<223> OTHER INFORMATION: /replace="Arg" or "Asn" or "Asp" or "Glu" or
      "Gln" or "Gly" or "His" or "Ile" or "Leu" or "Lys" or "Phe"
      or "Pro" or "Ser" or "Thr" or "Trp" or "Tyr" or "Val"
<220> FEATURE:
<221> NAME/KEY: VARIANT
<222> LOCATION: (34)..(34)
<223> OTHER INFORMATION: /replace="Arg" or "Asn" or "Asp" or "Glu" or
      "Gln" or "Gly" or "His" or "Ile" or "Leu" or "Lys" or "Phe"
      or "Pro" or "Ser" or "Thr" or "Trp" or "Tyr" or "Val"
<220> FEATURE:
<221> NAME/KEY: VARIANT
<222> LOCATION: (36)..(36)
<223> OTHER INFORMATION: /replace="Arg" or "Asn" or "Asp" or "Glu" or
      "Gln" or "Gly" or "His" or "Ile" or "Leu" or "Lys" or "Phe"
      or "Pro" or "Ser" or "Thr" or "Trp" or "Tyr" or "Val"
<220> FEATURE:
<221> NAME/KEY: VARIANT
<222> LOCATION: (38)..(41)
<223> OTHER INFORMATION: /replace="Arg" or "Asn" or "Asp" or "Glu" or
      "Gln" or "Gly" or "His" or "Ile" or "Leu" or "Lys" or "Phe"
      or "Pro" or "Ser" or "Thr" or "Trp" or "Tyr" or "Val"
<220> FEATURE:
<221> NAME/KEY: VARIANT
```

```
<222> LOCATION: (68)..(68)
<223> OTHER INFORMATION: /replace="Arg" or "Asn" or "Asp" or "Glu" or
      "Gln" or "Gly" or "His" or "Ile" or "Leu" or "Lys" or "Phe"
      or "Pro" or "Ser" or "Thr" or "Trp" or "Tyr" or "Val"
<220> FEATURE:
<221> NAME/KEY: VARIANT
<222> LOCATION: (70)..(70)
<223> OTHER INFORMATION: /replace="Arg" or "Asn" or "Asp" or "Glu" or
      "Gln" or "Gly" or "His" or "Ile" or "Leu" or "Lys" or "Phe"
      or "Pro" or "Ser" or "Thr" or "Trp" or "Tyr" or "Val"
<220> FEATURE:
<221> NAME/KEY: VARIANT
<222> LOCATION: (72)..(72)
<223> OTHER INFORMATION: /replace="Arg" or "Asn" or "Asp" or "Glu" or
      "Gln" or "Gly" or "His" or "Ile" or "Leu" or "Lys" or "Phe"
      or "Pro" or "Ser" or "Thr" or "Trp" or "Tyr" or "Val"
<220> FEATURE:
<221> NAME/KEY: VARIANT
<222> LOCATION: (78)..(79)
<223> OTHER INFORMATION: /replace="Arg" or "Asn" or "Asp" or "Glu" or
      "Gln" or "Gly" or "His" or "Ile" or "Leu" or "Lys" or "Phe"
      or "Pro" or "Ser" or "Thr" or "Trp" or "Tyr" or "Val"
<220> FEATURE:
<221> NAME/KEY: VARIANT
<222> LOCATION: (81)..(81)
<223> OTHER INFORMATION: /replace="Arg" or "Asn" or "Asp" or "Glu" or
      "Gln" or "Gly" or "His" or "Ile" or "Leu" or "Lys" or "Phe"
      or "Pro" or "Ser" or "Thr" or "Trp" or "Tyr" or "Val"
<220> FEATURE:
<221> NAME/KEY: MISC_FEATURE
<222> LOCATION: (1)..(89)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 46

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ala Tyr Ala Glu Ala Ala Ala Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ala Val Ala Ile Ala Gly Val Lys Gly Gly Ala Ala Ser
65                  70                  75                  80

Ala Pro Leu Ser Ala Ile Phe Thr Thr
                85

<210> SEQ ID NO 47
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (32)..(32)
<223> OTHER INFORMATION: /replace="Arg" or "Asn" or "Asp" or "Glu" or
      "Gln" or "Gly" or "His" or "Ile" or "Leu" or "Lys" or "Phe"
      or "Pro" or "Ser" or "Thr" or "Trp" or "Tyr" or "Val"
<220> FEATURE:
<221> NAME/KEY: VARIANT
<222> LOCATION: (34)..(34)
<223> OTHER INFORMATION: /replace="Arg" or "Asn" or "Asp" or "Glu" or
      "Gln" or "Gly" or "His" or "Ile" or "Leu" or "Lys" or "Phe"
``` or "Pro" or "Ser" or "Thr" or "Trp" or "Tyr" or "Val"
<220> FEATURE:
<221> NAME/KEY: VARIANT
<222> LOCATION: (36)..(36)
<223> OTHER INFORMATION: /replace="Arg" or "Asn" or "Asp" or "Glu" or
    "Gln" or "Gly" or "His" or "Ile" or "Leu" or "Lys" or "Phe"
    or "Pro" or "Ser" or "Thr" or "Trp" or "Tyr" or "Val"
<220> FEATURE:
<221> NAME/KEY: VARIANT
<222> LOCATION: (38)..(41)
<223> OTHER INFORMATION: /replace="Arg" or "Asn" or "Asp" or "Glu" or
    "Gln" or "Gly" or "His" or "Ile" or "Leu" or "Lys" or "Phe"
    or "Pro" or "Ser" or "Thr" or "Trp" or "Tyr" or "Val"
<220> FEATURE:
<221> NAME/KEY: VARIANT
<222> LOCATION: (46)..(46)
<223> OTHER INFORMATION: /replace="Arg" or "Asn" or "Asp" or "Glu" or
    "Gln" or "Gly" or "His" or "Ile" or "Leu" or "Lys" or "Phe"
    or "Pro" or "Ser" or "Thr" or "Trp" or "Tyr" or "Val"
<220> FEATURE:
<221> NAME/KEY: VARIANT
<222> LOCATION: (48)..(48)
<223> OTHER INFORMATION: /replace="Arg" or "Asn" or "Asp" or "Glu" or
    "Gln" or "Gly" or "His" or "Ile" or "Leu" or "Lys" or "Phe"
    or "Pro" or "Ser" or "Thr" or "Trp" or "Tyr" or "Val"
<220> FEATURE:
<221> NAME/KEY: VARIANT
<222> LOCATION: (68)..(68)
<223> OTHER INFORMATION: /replace="Arg" or "Asn" or "Asp" or "Glu" or
    "Gln" or "Gly" or "His" or "Ile" or "Leu" or "Lys" or "Phe"
    or "Pro" or "Ser" or "Thr" or "Trp" or "Tyr" or "Val"
<220> FEATURE:
<221> NAME/KEY: VARIANT
<222> LOCATION: (70)..(70)
<223> OTHER INFORMATION: /replace="Arg" or "Asn" or "Asp" or "Glu" or
    "Gln" or "Gly" or "His" or "Ile" or "Leu" or "Lys" or "Phe"
    or "Pro" or "Ser" or "Thr" or "Trp" or "Tyr" or "Val"
<220> FEATURE:
<221> NAME/KEY: VARIANT
<222> LOCATION: (72)..(72)
<223> OTHER INFORMATION: /replace="Arg" or "Asn" or "Asp" or "Glu" or
    "Gln" or "Gly" or "His" or "Ile" or "Leu" or "Lys" or "Phe"
    or "Pro" or "Ser" or "Thr" or "Trp" or "Tyr" or "Val"
<220> FEATURE:
<221> NAME/KEY: VARIANT
<222> LOCATION: (78)..(79)
<223> OTHER INFORMATION: /replace="Arg" or "Asn" or "Asp" or "Glu" or
    "Gln" or "Gly" or "His" or "Ile" or "Leu" or "Lys" or "Phe"
    or "Pro" or "Ser" or "Thr" or "Trp" or "Tyr" or "Val"
<220> FEATURE:
<221> NAME/KEY: VARIANT
<222> LOCATION: (81)..(81)
<223> OTHER INFORMATION: /replace="Arg" or "Asn" or "Asp" or "Glu" or
    "Gln" or "Gly" or "His" or "Ile" or "Leu" or "Lys" or "Phe"
    or "Pro" or "Ser" or "Thr" or "Trp" or "Tyr" or "Val"
<220> FEATURE:
<221> NAME/KEY: VARIANT
<222> LOCATION: (84)..(84)
<223> OTHER INFORMATION: /replace="Arg" or "Asn" or "Asp" or "Glu" or
    "Gln" or "Gly" or "His" or "Ile" or "Leu" or "Lys" or "Phe"
    or "Pro" or "Ser" or "Thr" or "Trp" or "Tyr" or "Val"
<220> FEATURE:
<221> NAME/KEY: VARIANT
<222> LOCATION: (86)..(86)
<223> OTHER INFORMATION: /replace="Arg" or "Asn" or "Asp" or "Glu" or
    "Gln" or "Gly" or "His" or "Ile" or "Leu" or "Lys" or "Phe"
    or "Pro" or "Ser" or "Thr" or "Trp" or "Tyr" or "Val"
<220> FEATURE:
<221> NAME/KEY: MISC_FEATURE
<222> LOCATION: (1)..(89)
<223> OTHER INFORMATION: /note="Variant residues given in the sequence
    have no preference with respect to those in the annotations
    for variant positions"
<220> FEATURE:
<221> NAME/KEY: source
<223> OTHER INFORMATION: /note="See specification as filed for detailed
    description of substitutions and preferred embodiments"

<400> SEQUENCE: 47

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ala Tyr Ala Glu Ala Ala Ala Gly Glu Ala Ile Ala Leu Ala
        35                  40                  45

Val Pro Gly Ser Glu Arg Ser Tyr Asp Leu Thr Gly Leu Lys Pro Gly
    50                  55                  60

Thr Glu Tyr Ala Val Ala Ile Ala Gly Val Lys Gly Gly Ala Ala Ser
65                  70                  75                  80

Ala Pro Leu Ala Ala Ala Phe Thr Thr
                85
```

<210> SEQ ID NO 48
<211> LENGTH: 99
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: (22)..(30)
<223> OTHER INFORMATION: /replace="Arg" or "Asn" or "Asp" or "Glu" or "Gln" or "Gly" or "His" or "Ile" or "Leu" or "Lys" or "Phe" or "Pro" or "Ser" or "Thr" or "Trp" or "Tyr" or "Val"
<220> FEATURE:
<221> NAME/KEY: MISC_FEATURE
<222> LOCATION: (22)..(30)
<223> OTHER INFORMATION: /note="This region may encompass 6-9 residues"
<220> FEATURE:
<221> NAME/KEY: VARIANT
<222> LOCATION: (78)..(89)
<223> OTHER INFORMATION: /replace="Arg" or "Asn" or "Asp" or "Glu" or "Gln" or "Gly" or "His" or "Ile" or "Leu" or "Lys" or "Phe" or "Pro" or "Ser" or "Thr" or "Trp" or "Tyr" or "Val"
<220> FEATURE:
<221> NAME/KEY: MISC_FEATURE
<222> LOCATION: (78)..(89)
<223> OTHER INFORMATION: /note="This region may encompass 7-12 residues"
<220> FEATURE:
<221> NAME/KEY: MISC_FEATURE
<222> LOCATION: (1)..(99)
<223> OTHER INFORMATION: /note="Variant residues given in the sequence have no preference with respect to those in the annotations for variant positions"
<220> FEATURE:
<221> NAME/KEY: source
<223> OTHER INFORMATION: /note="See specification as filed for detailed description of substitutions and preferred embodiments"

<400> SEQUENCE: 48

```
Leu Pro Ala Pro Lys Asn Leu Val Val Ser Arg Val Thr Glu Asp Ser
1               5                   10                  15

Ala Arg Leu Ser Trp Ala Ala Ala Ala Ala Ala Ala Ala Phe Asp
            20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Ala Ala Ala
65                  70                  75                  80

Ala Ala Ala Ala Ala Ala Ala Ala Ser Asn Pro Leu Ser Ala Ile
                85                  90                  95
```

Phe Thr Thr

<210> SEQ ID NO 49
<211> LENGTH: 153
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Arg Gly Arg Lys Lys Leu Leu Tyr Ile Phe Lys Gln Pro Phe Met Arg
1               5                   10                  15

Pro Val Gln Thr Thr Gln Glu Glu Asp Gly Cys Ser Cys Arg Phe Pro
            20                  25                  30

Glu Glu Glu Glu Gly Gly Cys Glu Leu Arg Val Lys Phe Ser Arg Ser
        35                  40                  45

Ala Asp Ala Pro Ala Tyr Lys Gln Gly Gln Asn Gln Leu Tyr Asn Glu
    50                  55                  60

Leu Asn Leu Gly Arg Arg Glu Glu Tyr Asp Val Leu Asp Lys Arg Arg
65                  70                  75                  80

Gly Arg Asp Pro Glu Met Gly Gly Lys Pro Arg Arg Lys Asn Pro Gln
                85                  90                  95

Glu Gly Leu Tyr Asn Glu Leu Gln Lys Asp Lys Met Ala Glu Ala Tyr
            100                 105                 110

Ser Glu Ile Gly Met Lys Gly Glu Arg Arg Arg Gly Lys Gly His Asp
        115                 120                 125

Gly Leu Tyr Gln Gly Leu Ser Thr Ala Thr Lys Asp Thr Tyr Asp Ala
    130                 135                 140

Leu His Met Gln Ala Leu Pro Pro Arg
145                 150

<210> SEQ ID NO 50
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Met Glu His Ser Thr Phe Leu Ser Gly Leu Val Leu Ala Thr Leu Leu
1               5                   10                  15

Ser Gln Val Ser Pro
            20

<210> SEQ ID NO 51
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Met Gln Ser Gly Thr His Trp Arg Val Leu Gly Leu Cys Leu Leu Ser
1               5                   10                  15

Val Gly Val Trp Gly Gln
            20

```
<210> SEQ ID NO 52
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 53
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Met Gly Asn Ser Cys Tyr Asn Ile Val Ala Thr Leu Leu Leu Val Leu
1               5                   10                  15

Asn Phe Glu Arg Thr Arg Ser
            20

<210> SEQ ID NO 54
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 55
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 56
<211> LENGTH: 26
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"

<400> SEQUENCE: 56

Ile Tyr Leu Ile Ile Gly Ile Cys Gly Gly Gly Ser Leu Leu Met Val
1               5                   10                  15

Phe Val Ala Leu Leu Val Phe Tyr Ile Thr
            20                  25

<210> SEQ ID NO 57
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Asn Leu Gly Ser Val Tyr Ile Tyr Val Leu Leu Ile Val Gly Thr Leu
1               5                   10                  15

Val Cys Gly Ile Val Leu Gly Phe Leu Phe
            20                  25

<210> SEQ ID NO 58
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Lys
            20                  25                  30

Ile Asn Tyr Arg Glu Glu Pro Ile Phe Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Gln Val Trp Ile Asp Gly Val Lys Gly Leu Trp Ser
65                  70                  75                  80

Leu Pro Leu Ser Ala Ile Phe Thr Thr
                85

<210> SEQ ID NO 59
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Trp Tyr Trp Glu Thr Lys Trp Glu Gly Glu Ala Ile Val Leu Ala 35                  40                  45

Val Pro Gly Ser Glu Arg Ser Tyr Asp Leu Thr Gly Leu Lys Pro Gly
    50                  55                  60

Thr Glu Tyr Asn Val Lys Ile Phe Gly Val Lys Gly Gly Tyr Pro Ser
65                  70                  75                  80

Asp Pro Leu Ser Ala Ile Phe Thr Thr
                85

<210> SEQ ID NO 60
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Trp Tyr Trp Glu Gln Phe Trp Phe Gly Glu Ala Ile Val Leu Thr
                35                  40                  45

Val Pro Gly Ser Glu Arg Ser Tyr Asp Leu Thr Gly Leu Lys Pro Gly
    50                  55                  60

Thr Glu Tyr Asn Val Lys Ile Tyr Gly Val Lys Gly Gly Leu Pro Ser
65                  70                  75                  80

Asn Pro Leu Ser Ala Ile Phe Thr Thr
                85

<210> SEQ ID NO 61
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
                20                  25                  30

Ile Gly Tyr Trp Glu Thr Tyr Glu Gly Gly Glu Ala Ile Val Leu Thr
                35                  40                  45

Val Pro Gly Ser Glu Arg Ser Tyr Asp Leu Thr Gly Leu Lys Pro Gly
    50                  55                  60

Thr Glu Tyr Leu Val Ala Ile Gln Gly Val Lys Gly Gly Gly Tyr Ser
65                  70                  75                  80

Leu Pro Leu Ser Ala Ile Phe Thr Thr
                85

<210> SEQ ID NO 62
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 62

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Ala Tyr Trp Glu Thr Tyr Val Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Ala Ile Val Gly Val Lys Gly Tyr Thr Ser
65                  70                  75                  80

Thr Pro Leu Ser Ala Ile Phe Thr Thr
                85

<210> SEQ ID NO 63
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Phe Lys
            20                  25                  30

Ile Asn Tyr Arg Glu Glu Pro Ile Phe Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Gln Val Trp Ile Asp Gly Val Lys Gly Leu Trp Ser
65                  70                  75                  80

Leu Pro Leu Ser Ala Ile Phe Thr Thr
                85

<210> SEQ ID NO 64
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Ser Tyr Tyr Glu Tyr Arg Ala Leu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Tyr Val Tyr Ile Gln Gly Val Lys Gly Gly Leu Pro Ser
65                  70                  75                  80

```
Glu Pro Leu Ser Ala Ile Phe Thr Thr
                85
```

```
<210> SEQ ID NO 65
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65
```

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Glu Tyr Ala Glu Ile Ala Asn Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Lys Val Trp Ile Leu Gly Val Lys Gly Tyr Tyr Ser
65                  70                  75                  80

Gly Pro Leu Ser Ala Ile Phe Thr Thr
                85
```

```
<210> SEQ ID NO 66
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66
```

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Glu Tyr Trp Glu Ile Asp His Arg Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ile Val Phe Ile Leu Gly Val Lys Gly Gly Tyr Tyr Ser
65                  70                  75                  80

Asp Pro Leu Ser Ala Ile Phe Thr Thr
                85
```

```
<210> SEQ ID NO 67
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67
```

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
```

```
                    20                  25                  30

Ile Glu Tyr Trp Glu Lys Ser Gln Ala Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Ile Val Gly Ile Gly Val Lys Gly Gly Arg Tyr Ser
65                  70                  75                  80

Pro Pro Leu Ser Ala Ile Phe Thr Thr
                85
```

<210> SEQ ID NO 68
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 68

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Ala Tyr Pro Glu Thr Tyr Trp Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Gln Val Gly Ile Gln Gly Val Lys Gly Gly Thr Lys Ser
65                  70                  75                  80

Ser Pro Leu Ser Ala Ile Phe Thr Thr
                85
```

<210> SEQ ID NO 69
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 69

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Ala Tyr Gly Glu Arg Trp Ala Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Tyr Val Tyr Ile Asp Gly Val Lys Val Cys Tyr Tyr Ser
65                  70                  75                  80

Ala Pro Leu Ser Ala Ile Phe Thr Thr
                85
```

<210> SEQ ID NO 70
<211> LENGTH: 90
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 70

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Trp Tyr Tyr Glu Asn Leu Trp Trp Gly Gly Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Leu Val Lys Ile Phe Gly Val Lys Gly Gly Phe Thr
65                  70                  75                  80

Ser Ser Pro Leu Ser Ala Ile Phe Thr Thr
                85                  90

<210> SEQ ID NO 71
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Phe
                20                  25                  30

Ile Pro Tyr Leu Glu Glu Gln Asp Tyr Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Leu Val Gly Ile Gly Gly Val Lys Gly Gly Trp Phe Ser
65                  70                  75                  80

Val Pro Leu Ser Ala Ile Phe Thr Thr
                85

<210> SEQ ID NO 72
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
                20                  25                  30

Ile Pro Tyr Ser Glu Asp Trp Gly Gly Gly Glu Ala Ile Val Leu Thr
            35                  40                  45

Val Pro Gly Ser Glu Arg Ser Tyr Asp Leu Thr Gly Leu Lys Pro Gly
    50                  55                  60
```

Thr Glu Tyr Leu Val Gly Ile Gly Gly Val Lys Gly Gly Arg Ser Ser
65                  70                  75                  80

Gln Pro Leu Ser Ala Ile Phe Thr Thr
                85

<210> SEQ ID NO 73
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
                20                  25                  30

Ile Ala Tyr Ala Glu Tyr Val Gly Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr His Val Val Ile Trp Gly Val Lys Gly Gly Tyr His Ser
65                  70                  75                  80

Leu Pro Leu Ser Ala Ile Phe Thr Thr
                85

<210> SEQ ID NO 74
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
                20                  25                  30

Ile Ser Tyr Glu Glu Ile Asp Arg Trp Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr His Val Val Ile Trp Gly Val Lys Gly Gly Tyr His Ser
65                  70                  75                  80

Leu Pro Leu Ser Ala Ile Phe Thr Thr
                85

<210> SEQ ID NO 75
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Leu Pro Ala Pro Lys Asn Leu Val Val Ser Arg Val Thr Glu Asp Ser

```
                1               5                   10                  15
            Ala Arg Leu Ser Trp Thr Ala Pro Asp Ala Ala Phe Asp Ser Phe Leu
                            20                  25                  30

Ile Gln Tyr Gln Glu Ser Glu Lys Val Gly Glu Ala Ile Val Leu Thr
                            35                  40                  45

Val Pro Gly Ser Glu Arg Ser Tyr Asp Leu Thr Gly Leu Lys Pro Gly
                        50                  55                  60

Thr Glu Tyr Thr Val Ser Ile Tyr Gly Val Gln Thr Asn Lys Tyr Trp
             65                 70                  75                  80

Trp Thr Tyr Trp His Gly Ser Asn Pro Leu Ser Ala Ile Phe Thr Thr
                                85                  90                  95

<210> SEQ ID NO 76
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Leu Pro Ala Pro Lys Asn Leu Val Val Ser Arg Val Thr Glu Asp Ser
             1               5                   10                  15

Ala Arg Leu Ser Trp Thr Ala Pro Asp Ala Ala Phe Asp Ser Phe Asp
                            20                  25                  30

Ile Lys Tyr Tyr Glu Ile Arg Asp Gly Gly Glu Ala Ile Val Leu Thr
                            35                  40                  45

Val Pro Gly Ser Glu Arg Ser Tyr Asp Leu Thr Gly Leu Lys Pro Gly
                        50                  55                  60

Thr Glu Tyr Gly Val Tyr Ile Gln Gly Val Lys Gly Gly Trp Pro Ser
             65                 70                  75                  80

Glu Pro Leu Ser Ala Ile Phe Thr Thr
                            85

<210> SEQ ID NO 77
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Leu Pro Ala Pro Lys Asn Leu Val Val Ser Arg Val Thr Glu Asp Ser
             1               5                   10                  15

Ala Arg Leu Ser Trp Thr Ala Pro Asp Ala Ala Phe Asp Ser Phe Val
                            20                  25                  30

Ile Tyr Tyr Trp Glu Thr Lys Trp Tyr Gly Glu Ala Ile Val Leu Thr
                            35                  40                  45

Val Pro Gly Ser Glu Arg Ser Tyr Asp Leu Thr Gly Leu Lys Pro Gly
                        50                  55                  60

Thr Glu Tyr Gly Val Tyr Ile Gln Gly Val Lys Gly Gly Trp Pro Ser
             65                 70                  75                  80

Glu Pro Leu Ser Ala Ile Phe Thr Thr
                            85

<210> SEQ ID NO 78
```

```
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Arg Glu Ser Glu Lys Val Gly Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Gln Thr Asn Lys Tyr Trp
65                  70                  75                  80

Trp Thr Tyr Trp His Gly Ser Asn Pro Leu Ser Ala Ile Phe Thr Thr
                85                  90                  95

```
<210> SEQ ID NO 79
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79
```

Leu Pro Ala Pro Lys Asn Leu Val Val Ser Arg Val Thr Glu Asp Ser
1               5                   10                  15

Ala Arg Leu Ser Trp Thr Ala Pro Asn Ala Ala Phe Asp Ser Phe Gly
            20                  25                  30

Ile Ala Tyr Tyr Glu Tyr Val Ser Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Tyr Ile Gln Gly Val Lys Gly Gly Ile Pro Ser
65                  70                  75                  80

Glu Pro Leu Ser Ala Ile Phe Thr Thr
                85

```
<210> SEQ ID NO 80
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

```
Val Pro Gly Ser Glu Arg Ser Tyr Asp Gln Thr Gly Leu Lys Pro Gly
 50                  55                  60

Thr Glu Tyr Thr Val Ser Ile Tyr Gly Val Gln Thr Asn Lys Tyr Trp
 65                  70                  75                  80

Trp Thr Tyr Trp His Gly Ser Asn Pro Leu Ser Ala Ile Phe Thr Thr
                 85                  90                  95
```

<210> SEQ ID NO 81
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

```
Leu Pro Ala Pro Lys Asn Leu Val Val Ser Arg Val Thr Glu Asp Ser
 1               5                  10                  15

Ala Arg Leu Ser Trp Thr Ala Pro Asn Ala Ala Phe Asp Ser Phe Gly
                 20                  25                  30

Ile Ala Tyr Tyr Glu Tyr Val Ser Tyr Gly Glu Ala Ile Val Leu Thr
                 35                  40                  45

Val Pro Gly Ser Glu Arg Ser Tyr Asp Leu Thr Gly Leu Lys Pro Gly
 50                  55                  60

Ile Glu Tyr Phe Val Tyr Ile Gln Gly Val Lys Gly Gly Ile Pro Ser
 65                  70                  75                  80

Glu Pro Leu Ser Ala Ile Phe Thr Thr
                 85
```

<210> SEQ ID NO 82
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ala
                 20                  25                  30

Ile Val Tyr Tyr Glu Pro Arg Asn Asp Gly Glu Ala Ile Val Leu Thr
                 35                  40                  45

Val Pro Gly Ser Glu Arg Ser Tyr Asp Leu Thr Gly Leu Lys Pro Gly
 50                  55                  60

Thr Glu Tyr Ile Val Tyr Ile Gln Gly Val Lys Gly Gly Leu Pro Ser
 65                  70                  75                  80

Glu Pro Leu Ser Ala Ile Phe Thr Thr
                 85
```

<210> SEQ ID NO 83
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Ser Tyr Glu Glu Ile Ala Arg Trp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr His Val Ile Ile Trp Gly Val Lys Gly Gly Gln Asp Ser
65                  70                  75                  80

Ile Pro Leu Ser Ala Ile Phe Thr Thr
                85

<210> SEQ ID NO 84
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Phe
            20                  25                  30

Ile Trp Tyr Gly Glu Trp Lys Ser Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Trp Ile Trp Gly Val Lys Gly Gly Val Asp Ser
65                  70                  75                  80

Trp Pro Leu Ser Ala Ile Phe Thr Thr
                85

<210> SEQ ID NO 85
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile His Tyr Tyr Glu Asp Arg Pro Gly Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Glu Val Phe Ile Trp Gly Val Lys Gly Gly Asn Pro
65                  70                  75                  80

Ser Trp Pro Leu Ser Ala Ile Phe Thr Thr
                85                  90

<210> SEQ ID NO 86
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Phe
            20                  25                  30

Ile Pro Tyr Val Glu Glu Trp Ser Asn Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ile Val Gly Ile Gly Gly Val Lys Gly Gly Ile Ala Ser
65                  70                  75                  80

Gln Pro Leu Ser Ala Ile Phe Thr Thr
                85
```

<210> SEQ ID NO 87
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

```
Leu Pro Ala Pro Lys Asn Leu Val Val Ser Arg Val Thr Glu Asp Ser
1               5                   10                  15

Ala Arg Leu Ser Trp Thr Ala Ser Asp Ala Ala Phe Asp Ser Phe Tyr
            20                  25                  30

Ile His Tyr Tyr Glu Asp Arg Pro Gly Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Glu Val Phe Ile Trp Gly Val Lys Gly Gly Asn Pro
65                  70                  75                  80

Ser Trp Pro Leu Ser Ala Ile Phe Thr Thr
                85                  90
```

<210> SEQ ID NO 88
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

```
Leu Pro Ala Pro Lys Asn Leu Val Val Ser Arg Val Thr Glu Asp Ser
1               5                   10                  15

Ala Arg Leu Ser Trp Trp Gln Arg His Asp Ser Phe Asp Ser Phe Leu
            20                  25                  30
```

```
Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Val Tyr Trp Trp Asn Tyr
 65                  70                  75                  80

Gly Thr Ser Asn Pro Leu Ser Ala Ile Phe Thr Thr
                 85                  90

<210> SEQ ID NO 89
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ala
                 20                  25                  30

Ile Arg Tyr Val Glu Ser Ala Asn Phe Gly Glu Ala Ile Trp Leu Lys
            35                  40                  45

Val Pro Gly Ser Glu Arg Ser Tyr Asp Leu Thr Gly Leu Lys Pro Gly
 50                  55                  60

Thr Glu Tyr Ile Val Val Ile Ser Gly Val Lys Gly Leu Phe Ser
 65                  70                  75                  80

Asn Pro Leu Tyr Ala Leu Phe Thr Thr
                 85

<210> SEQ ID NO 90
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ile
                 20                  25                  30

Ile Arg Tyr Arg Glu Gly Asp His Ser Gly Glu Ala Ile Trp Leu Glu
            35                  40                  45

Val Pro Gly Ser Glu Arg Ser Tyr Asp Leu Thr Gly Leu Lys Pro Gly
 50                  55                  60

Thr Glu Tyr Ile Val Val Ile Asp Gly Val Lys Gly Gly Trp Phe Ser
 65                  70                  75                  80

Thr Pro Leu Asn Ala Ser Phe Thr Thr
                 85

<210> SEQ ID NO 91
<211> LENGTH: 89
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic polypeptide"

<400> SEQUENCE: 91

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe His
            20                  25                  30

Ile Arg Tyr Ile Glu Arg Arg Thr Trp Gly Glu Ala Ile Trp Leu Ser
        35                  40                  45

Val Pro Gly Ser Glu Arg Ser Tyr Asp Leu Thr Gly Leu Lys Pro Gly
    50                  55                  60

Thr Glu Tyr Val Val Ile Ile Ser Gly Val Lys Gly Gly His Tyr Ser
65                  70                  75                  80

Lys Pro Leu Thr Ala Ile Phe Thr Thr
                85

<210> SEQ ID NO 92
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Lys
            20                  25                  30

Ile Thr Tyr Ile Glu Val Phe Val Trp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ala Val Phe Ile Gln Gly Val Lys Gly Gly Ser Pro Ser
65                  70                  75                  80

Cys Pro Leu Ser Ala Ile Phe Thr Thr
                85

<210> SEQ ID NO 93
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Leu Pro Ala Pro Lys Asn Leu Val Val Ser Cys Val Thr Glu Asp Ser
1               5                   10                  15

Ala Arg Leu Ser Trp Thr Ala Pro Asp Ala Ala Phe Asp Ser Phe Pro
            20                  25                  30

Ile Gly Tyr His Glu Leu Pro Glu Ala Gly Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ile Val Ala Ile Arg Gly Val Lys Gly Gly Ser Pro Ser
65                  70                  75                  80
```

```
Gly Pro Leu Ser Ala Ile Phe Thr Thr
                85

<210> SEQ ID NO 94
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Ile Tyr Arg Glu Val Tyr Lys Leu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Phe Ile Thr Gly Val Lys Gly Gly Asp Leu Ser
65                  70                  75                  80

Ser Pro Leu Ser Ala Ile Phe Thr Thr
                85

<210> SEQ ID NO 95
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Tyr Tyr Ile Glu Val Ala Glu Trp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ala Val Phe Ile Phe Gly Val Lys Gly Gly His Arg Ser
65                  70                  75                  80

Leu Pro Leu Ser Ala Ile Phe Thr Thr
                85

<210> SEQ ID NO 96
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Leu Pro Ala Pro Lys Asn Leu Val Val Ser Arg Val Thr Glu Asp Ser
1               5                   10                  15
```

```
Ala Arg Leu Ser Trp Thr Ala Pro Asp Ala Ala Phe Asp Ser Phe Ile
            20                  25                  30

Ile Ile Tyr Arg Glu Pro Pro Val Gly Glu Ala Ile Val Leu Thr
            35                  40                  45

Val Pro Gly Ser Glu Arg Ser Tyr Asp Leu Thr Gly Leu Lys Pro Val
 50                  55                  60

Thr Glu Tyr Leu Val Gln Ile Ala Gly Val Lys Gly Asp Phe Ser
 65                  70                  75                  80

Gln Pro Leu Ser Ala Ile Phe Thr Thr
                85
```

<210> SEQ ID NO 97
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 97

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Met
            20                  25                  30

Ile Thr Tyr Tyr Glu Val Ala Ile Cys Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Asn Val Asn Ile Asp Gly Val Lys Gly Lys Arg Ser
 65                  70                  75                  80

Ile Pro Leu Ser Ala Ile Phe Thr Thr
                85
```

<210> SEQ ID NO 98
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 98

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
            20                  25                  30

Ile Val Tyr His Glu Thr Ile Lys Asn Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Glu Val His Ile Pro Gly Val Lys Gly Gly Asp Pro Ser
 65                  70                  75                  80

Thr Pro Leu Ser Ala Ile Phe Thr Thr
                85
```

<210> SEQ ID NO 99
<211> LENGTH: 68
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Leu Pro Ala Pro Lys Asn Leu Val Val Ser Arg Ile Thr Tyr His Glu
1               5                   10                  15

Val Phe Trp Ile Gly Glu Ala Ile Arg Leu His Val Pro Gly Ser Glu
            20                  25                  30

Arg Ser Tyr Asp Leu Thr Gly Leu Lys Pro Gly Thr Glu Tyr Ile Val
        35                  40                  45

Glu Ile Arg Gly Val Lys Gly Gly Pro Ser Glu Pro Leu Thr Ala
    50                  55                  60

Asn Phe Thr Thr
65

<210> SEQ ID NO 100
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Pro Tyr Trp Glu Pro Glu Ser Trp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Gly Val Phe Ile Val Gly Val Lys Gly Gly Glu Val Ser
65                  70                  75                  80

Tyr Pro Leu Ser Ala Ile Phe Thr Thr
                85

<210> SEQ ID NO 101
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Gln Tyr Ile Glu Val Gln Glu Trp Gly Glu Ala Ile Val Leu Thr
        35                  40                  45

Val Pro Gly Ser Glu Arg Ser Tyr Asn Leu Thr Gly Leu Lys Pro Gly
    50                  55                  60

Thr Glu Tyr Ala Val Leu Ile Arg Gly Val Lys Gly Gly Phe Leu Ser
65                  70                  75                  80
```

```
Arg Pro Leu Ser Ala Ile Phe Thr Thr
                85

<210> SEQ ID NO 102
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Val
            20                  25                  30

Ile Val Tyr His Glu Gln Ser Lys Trp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Arg Ile Ala Gly Val Lys Gly Gly Asp Phe Ser
65                  70                  75                  80

Val Pro Arg Ser Ala Ile Phe Thr Thr
                85

<210> SEQ ID NO 103
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asn Ser Phe Asn
            20                  25                  30

Ile Thr Tyr Ile Glu Thr Val Val Trp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ser Val Phe Ile Gln Gly Val Lys Gly Gly Val Phe Ser
65                  70                  75                  80

Arg Pro Leu Tyr Ala Ile Phe Thr Thr
                85

<210> SEQ ID NO 104
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Leu Pro Ala Pro Lys Asn Leu Val Val Ser Arg Val Thr Glu Asp Ser
1               5                   10                  15
```

Ala Arg Leu Ser Trp Thr Ala Pro Asp Ala Ala Phe Asp Ser Phe Thr
            20                  25                  30

Ile His Tyr Leu Glu Val Arg Thr Trp Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Ala Val Phe Ile Phe Gly Val Lys Gly Gly Asn Arg Ser
65                  70                  75                  80

Arg Pro Leu Ser Ala Ile Phe Thr Thr
                85

<210> SEQ ID NO 105
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Phe
            20                  25                  30

Ile Lys Tyr Ile Glu Val Val Asn Trp Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Trp Val Gly Ile Gly Gly Val Lys Gly Gly Lys Val Ser
65                  70                  75                  80

Trp Pro Leu Ser Ala Ile Phe Thr Thr
                85

<210> SEQ ID NO 106
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Lys Tyr Ile Glu Val Ile Thr Trp Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Tyr Val Ile Ile Phe Gly Val Lys Gly Gly Val Phe Ser
65                  70                  75                  80

Gly Pro Leu Ser Ala Ile Phe Thr Thr
                85

<210> SEQ ID NO 107
<211> LENGTH: 89
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
                20                  25                  30

Ile Thr Tyr Ile Glu Thr Val Val Trp Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Ser Val Phe Ile Gln Gly Val Lys Gly Val Phe Ser
65                  70                  75                  80

Arg Pro Leu Tyr Ala Ile Phe Thr Thr
                85

<210> SEQ ID NO 108
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
                20                  25                  30

Ile Trp Tyr Ile Glu Arg Gln Ala Trp Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Ala Val Leu Ile Glu Gly Val Lys Gly Gly Trp Leu Ser
65                  70                  75                  80

Lys Pro Leu Ser Ala Ile Phe Thr Thr
                85

<210> SEQ ID NO 109
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Leu Pro Ala Pro Lys Asn Leu Ile Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Tyr Tyr Leu Glu Thr Lys Glu Trp Gly Glu Ala Ile Val Leu Thr
            35                  40                  45

Val Pro Gly Ser Glu Arg Ser Tyr Asp Leu Thr Gly Leu Lys Pro Gly
    50                  55                  60
```

```
Thr Glu Tyr Thr Val Val Ile Phe Gly Val Lys Gly Gly Arg Ser
 65                  70                  75                  80

Asp Pro Leu Tyr Ala Ile Phe Thr Thr
                 85
```

<210> SEQ ID NO 110
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

```
Leu Pro Ala Pro Lys Asn Leu Val Val Ser Arg Val Thr Glu Asp Ser
  1               5                  10                  15

Ala Arg Leu Ser Trp Thr Ala Pro Asp Ala Ala Phe Asp Ser Phe Ala
             20                  25                  30

Ile Tyr Tyr Leu Glu Thr Lys Glu Trp Gly Glu Ala Ile Val Leu Thr
         35                  40                  45

Val Pro Gly Ser Glu Arg Ser Tyr Asp Leu Thr Gly Leu Lys Pro Gly
     50                  55                  60

Thr Glu Tyr Thr Val Val Ile Phe Gly Val Lys Gly Gly Arg Ser
 65                  70                  75                  80

Asp Pro Leu Tyr Ala Ile Phe Thr Thr
                 85
```

<210> SEQ ID NO 111
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

```
Leu Pro Ala Pro Lys Asn Leu Val Val Ser Arg Val Thr Glu Asp Ser
  1               5                  10                  15

Ala Arg Leu Ser Trp Thr Ala Pro Asp Ala Ala Phe Asp Ser Phe Trp
             20                  25                  30

Ile Val Tyr Arg Glu Arg Val Gln Trp Gly Glu Ala Ile Val Leu Thr
         35                  40                  45

Val Pro Gly Ser Glu Arg Ser Tyr Asp Leu Thr Gly Leu Lys Pro Gly
     50                  55                  60

Thr Glu Tyr Tyr Val Gln Ile Pro Gly Val Lys Gly Gly Asp Pro Ser
 65                  70                  75                  80

Pro Pro Leu Ser Ala Ile Phe Thr Thr
                 85
```

<210> SEQ ID NO 112
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
            20                  25                  30

Ile Thr Tyr Ile Glu Thr Val Val Trp Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Ser Val Phe Ile Gln Gly Val Lys Gly Val Phe Ser
65                  70                  75                  80

Arg Pro Leu Tyr Ala Ile Ser Thr Thr
                85

<210> SEQ ID NO 113
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
            20                  25                  30

Ile Tyr Tyr Arg Glu Ile Ser Gln Glu Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Trp Val Lys Ile Ala Gly Val Lys Cys Gly Asp Phe Ser
65                  70                  75                  80

Asn Pro Leu Ser Ala Ile Phe Thr Thr
                85

<210> SEQ ID NO 114
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Ile Tyr Thr Glu Pro Pro Trp Gln Cys Gly Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Glu Val Arg Ile Ala Gly Val Lys Gly Gly Asp Pro Ser
65                  70                  75                  80

Glu Pro Leu Ser Ala Ile Phe Thr Thr
                85

```
<210> SEQ ID NO 115
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Phe Tyr Leu Glu Gln Lys Val Trp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ala Val Phe Ile Lys Gly Val Lys Gly Ala Ala Ser
65                  70                  75                  80

Gly Pro Leu Ser Ala Ile Phe Thr Thr
                85

<210> SEQ ID NO 116
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Val
            20                  25                  30

Ile Val Tyr Arg Glu Gln Pro Asp Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Tyr Val Gln Ile Ala Gly Val Lys Gly Gly Asp Leu Ser
65                  70                  75                  80

Tyr Pro Leu Ser Ala Ile Phe Thr Thr
                85

<210> SEQ ID NO 117
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Leu Pro Ala Pro Lys Asn Leu Val Ile Ser Arg Val Thr Glu Asp Ser
1               5                   10                  15

Ala Arg Leu Ser Trp Thr Ala Pro Asp Ala Ala Phe Asp Ser Phe Val
            20                  25                  30

Ile Val Tyr Arg Glu Trp Gly Ser Ala Gly Glu Ala Ile Val Leu Thr
        35                  40                  45
```

Val Pro Gly Ser Glu Arg Ser Tyr Asp Leu Thr Gly Leu Lys Pro Gly
            50                  55                  60

Thr Glu Tyr His Val Tyr Ile Ala Gly Val Lys Gly Gly Asp Phe Ser
 65                  70                  75                  80

Asn Pro Leu Ser Ala Ile Phe Thr Thr Thr
                85                  90

<210> SEQ ID NO 118
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Thr
                20                  25                  30

Ile Gly Tyr His Glu Leu Pro Asp Lys Gly Glu Ala Ile Val Leu Thr
                35                  40                  45

Val Pro Gly Ser Glu Arg Ser Tyr Asp Leu Thr Gly Leu Lys Pro Gly
            50                  55                  60

Thr Glu Tyr Ile Val Val Ile Arg Gly Val Lys Gly Gly Glu Trp Ser
 65                  70                  75                  80

Asp Pro Leu Ser Ala Ile Phe Thr Thr
                85

<210> SEQ ID NO 119
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Val
                20                  25                  30

Ile Val Tyr Asn Glu Leu Thr Asn Val Gly Glu Ala Ile Val Leu Thr
                35                  40                  45

Val Pro Gly Ser Glu Arg Ser Tyr Asp Leu Thr Gly Leu Lys Pro Gly
            50                  55                  60

Thr Glu Tyr Trp Val Arg Ile Ala Gly Val Lys Gly Gly Asp Phe Ser
 65                  70                  75                  80

Val Pro Leu Ser Ala Ile Phe Thr Thr
                85

<210> SEQ ID NO 120
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Val
                20                  25                  30

Ile Pro Tyr Ser Glu Ile His Ile Pro Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Trp Val Arg Ile Ser Gly Val Lys Gly Asp Leu Ser
65                  70                  75                  80

Leu Pro Leu Ser Ala Ile Phe Thr Thr
                85

<210> SEQ ID NO 121
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Phe
                20                  25                  30

Ile Gly Tyr Phe Glu Gln Asp Asn Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Ile Val Ala Ile Lys Gly Val Lys Gly Trp His Ser
65                  70                  75                  80

Arg Pro Leu Ser Ala Ile Phe Thr Thr
                85

<210> SEQ ID NO 122
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
                20                  25                  30

Ile Gly Tyr Trp Glu Ile Gly His Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Phe Val Phe Ile Ala Gly Val Lys Gly Leu Val Ser
65                  70                  75                  80

Phe Pro Leu Ser Ala Ile Phe Thr Thr

<210> SEQ ID NO 123
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 123

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Phe
                20                  25                  30

Ile Lys Tyr Ile Glu Val Val Asn Trp Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Trp Val Gly Ile Gly Gly Val Lys Gly Gly Lys Val Ser
65                  70                  75                  80

Trp Pro Leu Ser Ala Ile Val Thr Thr
                85
```

<210> SEQ ID NO 124
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 124

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Val
                20                  25                  30

Ile Val Tyr His Glu Ala His Tyr Ala Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Asn Val Arg Ile Ala Gly Val Lys Cys Gly Asp Phe Ser
65                  70                  75                  80

Trp Pro Leu Ser Ala Ile Phe Thr Thr
                85
```

<210> SEQ ID NO 125
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 125

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
                20                  25                  30
```

```
Ile Gln Tyr Ile Glu Val Gln Glu Trp Gly Glu Ala Ile Val Leu Thr
            35                  40                  45

Val Pro Gly Ser Glu Arg Ser Tyr Asp Leu Thr Gly Leu Lys Pro Gly
     50                  55                  60

Thr Glu Tyr Ala Val Leu Ile Arg Gly Val Lys Gly Gly Phe Leu Ser
65                  70                  75                  80

Arg Pro Leu Ser Ala Ile Phe Thr Thr
                85
```

<210> SEQ ID NO 126
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ile
            20                  25                  30

Ile Lys Tyr Ile Glu Val Val Trp Trp Gly Glu Ala Ile Val Leu Thr
            35                  40                  45

Val Pro Gly Ser Glu Arg Ser Tyr Asp Leu Thr Gly Leu Lys Pro Gly
     50                  55                  60

Thr Glu Tyr Tyr Val His Ile Glu Gly Val Lys Gly Gly Tyr Trp Ser
65                  70                  75                  80

Asn Pro Leu Ser Ala Ile Phe Thr Thr
                85
```

<210> SEQ ID NO 127
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
            20                  25                  30

Ile Ile Tyr Ile Glu Gln Lys Thr Trp Gly Glu Ala Ile Val Leu Thr
            35                  40                  45

Val Pro Gly Ser Glu Arg Ser Tyr Asp Leu Thr Gly Leu Lys Pro Gly
     50                  55                  60

Thr Glu Tyr Val Val Phe Ile Lys Gly Val Lys Gly Cys Ser Asn Ser
65                  70                  75                  80

Gln Pro Leu Ser Ala Ile Phe Thr Thr
                85
```

<210> SEQ ID NO 128
<211> LENGTH: 89
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 128

Leu Pro Ala Pro Lys Asn Leu Val Val Ser His Val Thr Glu Asp Ser
1               5                   10                  15

Ala Arg Leu Ser Trp Thr Ala Pro Asp Ala Ala Phe Asp Ser Phe Gly
            20                  25                  30

Ile Ala Tyr Gly Glu Arg Trp Ala Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Tyr Val Tyr Ile Asp Gly Val Lys Val Cys Tyr Tyr Ser
65                  70                  75                  80

Ala Pro Leu Ser Ala Ile Phe Thr Thr
                85

<210> SEQ ID NO 129
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Leu Pro Ala Pro Lys Asn Leu Val Val Ser Arg Val Thr Glu Asp Ser
1               5                   10                  15

Ala Arg Leu Ser Trp Thr Ala Gln Asp Ala Ala Phe Asp Ser Phe Gly
            20                  25                  30

Ile Ala Tyr Gly Glu Arg Trp Ala Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Tyr Val Tyr Ile Asp Gly Val Lys Val Cys Tyr Tyr Ser
65                  70                  75                  80

Ala Pro Leu Ser Ala Ile Phe Thr Thr
                85

<210> SEQ ID NO 130
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Leu Pro Ala Pro Lys Asn Leu Val Val Ser Arg Ile Thr Glu Asp Ser
1               5                   10                  15

Ala Arg Leu Ser Trp Thr Ala Pro Asp Ala Ala Phe Asp Ser Phe Gly
            20                  25                  30

Ile Ala Tyr Gly Glu Arg Trp Ala Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Tyr Val Tyr Ile Asp Gly Val Lys Val Cys Tyr Tyr Ser

Ala Pro Leu Ser Ala Ile Phe Thr Thr
                85

<210> SEQ ID NO 131
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Ser Tyr Glu Glu Ile Asp Cys Trp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr His Val Val Ile Trp Gly Val Lys Gly Gly Tyr His Ser
65                  70                  75                  80

Leu Pro Leu Ser Ala Ile Phe Thr Thr
                85

<210> SEQ ID NO 132
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Leu Pro Ala Pro Lys Asn Leu Val Val Ser Arg Val Thr Glu Asp Ser
1               5                   10                  15

Ala Arg Leu Ser Trp Thr Thr Pro Asp Ala Ala Phe Asp Ser Phe Phe
            20                  25                  30

Ile Pro Tyr Leu Glu Glu Gln Asp Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Gly Ile Gly Gly Val Lys Gly Gly Trp Phe Ser
65                  70                  75                  80

Val Pro Leu Ser Ala Ile Phe Thr Thr
                85

<210> SEQ ID NO 133
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Leu Pro Ala Pro Lys Asn Leu Val Val Ser Arg Val Thr Glu Asp Tyr
1               5                   10                  15

Ala Arg Leu Ser Trp Thr Ala Pro Asp Ala Ala Phe Asp Ser Phe Tyr
            20                  25                  30

Ile Ser Tyr Glu Glu Ile Asp Arg Trp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr His Val Val Ile Trp Gly Val Lys Gly Gly Tyr His Ser
65                  70                  75                  80

Leu Pro Leu Ser Ala Ile Phe Thr Thr
                85

<210> SEQ ID NO 134
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
            20                  25                  30

Ile Tyr Tyr Pro Glu Trp Asn Pro Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Gly Ile Trp Gly Val Lys Gly Gly Leu Asp Ser
65                  70                  75                  80

Trp Pro Leu Ser Val Ile Phe Thr Thr
                85

<210> SEQ ID NO 135
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Leu Pro Ala Pro Lys Asn Leu Val Val Ser Arg Val Thr Glu Asp Ser
1               5                   10                  15

Ala Arg Leu Ser Trp Thr Ala Pro Asn Ala Ala Phe Asp Ser Phe Tyr
            20                  25                  30

Ile Gly Tyr Tyr Glu Leu Arg Asn Ala Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Asp Val Ile Ile Pro Gly Val Lys Gly Gly Trp Thr Ser
65                  70                  75                  80

Asp Pro Leu Ser Ala Ile Phe Thr Thr
                85

<210> SEQ ID NO 136
<211> LENGTH: 89

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Ala Tyr Tyr Glu Tyr Val Ser Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Tyr Ile Gln Gly Val Lys Gly Gly Ile Pro Ser
65                  70                  75                  80

Glu Pro Leu Ser Ala Ile Phe Thr Thr
                85

<210> SEQ ID NO 137
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Lys Tyr Tyr Glu Ile His Asp Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Gly Val Tyr Ile Gln Gly Val Lys Gly Gly Trp Pro Ser
65                  70                  75                  80

Glu Pro Leu Ser Ala Ile Phe Thr Thr
                85

<210> SEQ ID NO 138
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

Leu Pro Ala Pro Lys Asn Leu Val Val Ser Arg Val Thr Glu Asp Ser
1               5                   10                  15

Ala Arg Leu Ser Trp Thr Ala Ser Asp Ala Ala Phe Asp Ser Phe Asp
            20                  25                  30

Ile Lys Tyr Tyr Glu Ile Arg Asp Gly Gly Glu Ala Ile Val Leu Thr
        35                  40                  45

Val Pro Gly Ser Glu Arg Ser Tyr Asp Leu Thr Gly Leu Lys Pro Gly
```

```
                    50                  55                  60
Thr Glu Tyr Gly Val Tyr Ile Gln Gly Val Lys Gly Gly Trp Pro Ser
 65                  70                  75                  80

Glu Pro Leu Ser Ala Ile Phe Thr Thr
                 85

<210> SEQ ID NO 139
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Leu Pro Ala Pro Lys Asn Leu Val Val Ser Arg Val Thr Glu Asp Ser
  1               5                  10                  15

Ala Arg Leu Ser Trp Thr Ala Pro Asp Ala Ala Phe Asp Ser Phe Phe
                 20                  25                  30

Ile Ile Tyr Gly Glu Gly Gln Leu Tyr Gly Glu Ala Ile Val Leu Thr
             35                  40                  45

Val Pro Gly Ser Glu Arg Ser Tyr Asp Leu Thr Gly Leu Lys Pro Gly
 50                  55                  60

Thr Glu Tyr Gln Val Trp Ile Tyr Gly Val Lys Gly Gly Asn Tyr Ser
 65                  70                  75                  80

Lys Pro Leu Ser Ala Ile Phe Thr Thr
                 85

<210> SEQ ID NO 140
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Leu Pro Ala Pro Lys Asn Leu Val Val Ser Arg Val Thr Glu Asp Ser
  1               5                  10                  15

Ala Arg Leu Ser Trp Thr Ala Pro Asp Ala Ala Phe Asp Ser Phe Gly
                 20                  25                  30

Ile Ala Tyr Tyr Glu Tyr Val Ser Tyr Gly Glu Ala Ile Val Leu Thr
             35                  40                  45

Val Pro Gly Ser Glu Arg Ser Tyr Asp Leu Thr Gly Leu Lys Pro Gly
 50                  55                  60

Thr Glu Tyr Phe Val Tyr Ile Gln Gly Val Lys Gly Gly Trp Pro Ser
 65                  70                  75                  80

Glu Pro Leu Ser Ala Ile Phe Thr Thr
                 85

<210> SEQ ID NO 141
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141
```

```
Leu Pro Ala Pro Lys Asn Leu Val Val Ser Arg Val Thr Glu Asp Ser
1               5                   10                  15

Ala Arg Pro Ser Trp Thr Ala Pro Asp Ala Ala Phe Asp Ser Phe Val
            20                  25                  30

Ile Tyr Tyr Trp Glu Thr Lys Trp Tyr Gly Glu Ala Ile Val Leu Thr
            35                  40                  45

Val Pro Gly Ser Glu Arg Ser Tyr Asp Leu Thr Gly Leu Lys Pro Gly
50                  55                  60

Thr Glu Tyr Ile Val Lys Ile Phe Gly Val Lys Gly Leu Ile Ser
65                  70                  75                  80

Glu Pro Leu Ser Ala Ile Phe Thr Thr
                85
```

<210> SEQ ID NO 142
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 142

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Lys Tyr Tyr Glu Ile Arg Asp Gly Glu Ala Ile Val Leu Thr
            35                  40                  45

Val Pro Gly Ser Glu Arg Ser Tyr Asp Leu Thr Gly Leu Lys Pro Gly
50                  55                  60

Thr Lys Tyr Gly Val Tyr Ile Gln Gly Val Lys Gly Gly Trp Pro Ser
65                  70                  75                  80

Glu Pro Leu Ser Ala Ile Phe Thr Thr
                85
```

<210> SEQ ID NO 143
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 143

```
Leu Pro Ala Pro Lys Asn Leu Val Val Ser Arg Val Thr Glu Asp Ser
1               5                   10                  15

Ala Arg Leu Ser Trp Thr Ala Leu Asp Ala Ala Phe Asp Ser Phe Ala
            20                  25                  30

Ile Val Tyr Tyr Glu Pro Arg Asn Asp Gly Glu Ala Ile Val Leu Thr
            35                  40                  45

Val Pro Gly Ser Glu Arg Ser Tyr Asp Leu Thr Gly Leu Lys Pro Gly
50                  55                  60

Thr Glu Tyr Ile Val Tyr Ile Gln Gly Val Lys Gly Gly Leu Pro Ser
65                  70                  75                  80

Glu Pro Leu Ser Ala Ile Phe Thr Thr
                85
```

```
<210> SEQ ID NO 144
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

Leu Pro Ala Pro Lys Asn Leu Val Val Ser Arg Val Thr Glu Asn Ser
1               5                  10                  15

Ala Arg Leu Ser Trp Thr Ala Pro Asp Ala Ala Phe Asp Ser Phe Ala
            20                  25                  30

Ile Val Tyr Tyr Glu Pro Arg Asn Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ile Val Tyr Ile Gln Gly Val Lys Gly Gly Leu Pro Ser
65                  70                  75                  80

Glu Pro Leu Ser Ala Ile Phe Thr Thr
                85

<210> SEQ ID NO 145
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Leu Pro Ala Pro Lys Asn Leu Val Val Ser His Val Thr Glu Asp Ser
1               5                  10                  15

Ala Arg Leu Ser Trp Thr Ala Pro Asp Ala Ala Phe Asp Ser Phe Phe
            20                  25                  30

Ile Trp Tyr Gly Glu Trp Lys Ser Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Trp Ile Trp Gly Val Lys Gly Gly Val Asp Ser
65                  70                  75                  80

Trp Pro Leu Ser Ala Ile Phe Thr Thr
                85
```

CHIMERIC ANTIGEN RECEPTORS COMPRISING BCMA-SPECIFIC FIBRONECTIN TYPE III DOMAINS AND USES THEREOF

CROSS-REFERENCE TO RELATED APPLICATIONS

This application is a U.S. National Stage Application under 35 U.S.C. § 371 of International Patent Application No. PCT/US2017/050888, filed Sep. 11, 2017, which claims the benefit of U.S. Provisional Application No. 62/394,329, filed Sep. 14, 2016, the disclosure of each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Aug. 31, 2017, is named JBI5097WOPCT_SL.txt and is 138,671 bytes in size.

FIELD OF THE INVENTION

The invention relates to BCMA-specific fibronectin type III (FN3) domains, BCMA-targeting chimeric antigen receptors (CARs) comprising the FN3 domains, and engineered BCMA-targeting immune cells expressing the CARs. Also provided are nucleic acids and expression vectors encoding the FN3 domains and the CARs, recombinant cells containing the vectors, and compositions comprising the engineered immune cells expressing the BCMA-targeting CARs. Methods of making the FN3 domains, CARs, and engineered immune cells, and methods of using the engineered immune cells to treat conditions including cancer are also provided.

BACKGROUND OF THE INVENTION

The genetic engineering of T cells to specifically engage and kill tumor cells in a target-specific manner has resulted in the establishment of new therapeutic options for cancer patients, referred to as engineered T cell therapy. This targeting is typically brought about by genetically manipulating patient-derived T cells with a recombinant DNA molecule that encodes a chimeric antigen receptor (CAR). CARs are synthetic receptors comprising an extracellular targeting domain that is linked to a linker peptide, a transmembrane (TM) domain, and one or more intracellular signaling domains. Traditionally, the extracellular domain consists of a single chain Fv fragment of an antibody (scFv) that is specific for a given tumor-associated antigen (TAA) or cell surface target. The extracellular scFv domain confers the tumor specificity of the CAR, while the signaling domains activate the T cell upon TAA/target engagement. These engineered T cells (CAR-T cells) are re-infused into cancer patients, where they specifically engage and kill cells expressing the TAA target of the CAR (Maus et al., Blood. 2014 Apr. 24; 123 (17):2625-35; Curran and Brentjens, J Clin Oncol. 2015 May 20; 33(15):1703-6). The immunoglobulin (Ig) fold is found in the variable regions of antibodies, as well as thousands of non-antibody proteins. It has been shown that one such Ig protein, the tenth fibronectin type III (FN3) repeat from human fibronectin, can tolerate a number of mutations in surface exposed loops while retaining the overall Ig-fold structure. Libraries of amino acid variants have been built into these loops and specific binders selected to a number of different targets. Such engineered FN3 domains have been found to bind to targets with high affinity, while retaining important biophysical properties. See, e.g., US2010/0216708 and references therein.

Many of clinical studies reporting the promising use of CAR-T therapies in hematologic malignancies focus on B-cell malignancies by targeting CD19 or CD20. Although CAR T-cell therapy is emerging as a powerful therapy, there is still a need for improving certain aspects of the therapy, such as, e.g., optimization of CAR signaling, identification of optimal target antigens, optimization of cell manufacturing methods, enhancement of CAR T-cell therapy safety, optimization of combinatorial strategies to improve the therapeutic potential of CAR T-cells, etc. (Dai et al., J Natl Cancer Inst. 2016 Jan. 27; 108(7)).

Multiple myeloma (MM) is a cancer that is characterized by an accumulation of clonal plasma cells. MM is the second most common hematologic malignancy, and it accounts for as many as 2% of deaths from all cancers. MM is a heterogeneous disease, and is characterized by a wide range of aggression and treatment resistance. Some patients live a decade or longer after diagnosis, while others suffer rapid treatment-resistant progression and die within 2 years. Despite progress in the development of new therapeutics, there is currently no cure for MM. Though current therapies often lead to remission of MM, the disease eventually relapses in nearly all patients and is ultimately fatal (Naymagon and Abdul-Hay, J Hematol Oncol. 2016 Jun. 30; 9(1):52). In addition, traditional methods of treatment, including chemotherapy and radiation therapy, have limited utility due to toxic side effects. Thus, there remains a need in the art for more effective therapeutics for treating MM.

A potential target for MM therapies is B cell maturation antigen (BCMA), a member of the tumor necrosis factor receptor family that is predominantly expressed on mature B cells (Coquery and Erickson, Crit Rev Immunol. 2012; 32(4):287-305). BCMA delivers pro-survival signals upon binding to its ligands, B cell activator of the TNF family (BAFF) and a proliferation inducing ligand (APRIL). BCMA triggers antigen presentation in B cells that is dependent on NF-κB and JNK signaling. In healthy individuals, BCMA plays a role in mediating the survival of plasma cells that maintain long-term humoral immunity, but its expression has also been linked to a number of cancers, autoimmune disorders, and infectious diseases. For example, BCMA RNA has been detected universally in MM cells and in other lymphomas, and BCMA protein has been detected on the surface of plasma cells from MM patients (Novak et al., Blood. 2004 Jan. 15; 103(2):689-94; Neri et al., Clin Cancer Res. 2007 Oct. 1; 13(19):5903-9; Bellucci et al., Blood. 2005 May 15; 105(10):3945-50; Moreaux et al., Blood. 2004 Apr. 15; 103(8):3148-57).

There is a need in the art for effective therapeutics that specifically and effectively target BCMA-expressing cells.

BRIEF SUMMARY OF THE INVENTION

The invention satisfies this need by providing BCMA-specific FN3 domains, BCMA-targeting CARs comprising the FN3 domains, engineered BCMA-targeting immune cells expressing the CARs, methods of making and methods of using thereof. When the BCMA-targeting CARs are expressed on the surface of pan T cells, the cells specifically kill BCMA-expressing tumor cell lines. Thus, the BCMA-targeting CARs of the invention can be used to effectively retarget T cells to kill BCMA-expressing cells in a highly specific manner.

While not wishing to be bound by theory, it is thought that the use of an FN3 domain, rather than an scFv, as the extracellular domain of a CAR will allow for more stable and controllable CAR molecules, because scFvs are inherently more prone to biophysical challenges. In addition, the small size of the FN3 domain will allow for better immunological synapse optimization and greater flexibility to target very specific domains of a TAA.

In one general aspect, the invention relates to an isolated FN3 domain that specifically binds to a BCMA, preferably the extracellular domain of a BCMA. In some embodiments, the FN3 is derived from Tencon.

In one embodiment, the isolated FN3 domain comprises an amino acid sequence that is at least 80% identical to SEQ ID NO: 1, wherein the FN3 domain binds to a human BCMA with a KD less than $1 \times 10^{-6}$ M as determined by using surface plasmon resonance.

In another embodiment, the isolated FN3 domain comprise the amino acid sequence of SEQ ID NO: 7.

In another embodiment, the isolated FN3 domain comprises an amino acid sequence that is at least 90% identical to one of SEQ ID NOs: 8-44 and 58-145. Preferably, the FN3 comprises the amino acid sequence of one of SEQ ID NOs: 8-44 and 58-145.

In other general aspects, the invention relates to an isolated polynucleotide encoding an FN3 domain of the invention, a vector comprising an isolated polynucleotide encoding an FN3 domain of the invention, and a host cell comprising an isolated nucleic acid encoding an FN3 domain of the invention. The invention also relates to a method of producing an FN3 domain of the invention, comprising culturing a host cell comprising a polynucleotide sequence encoding the FN3 domain under conditions to produce the FN3 domain, and recovering the FN3 domain from the cell or cell culture.

According to another general aspect, the invention relates to an isolated polynucleotide encoding a chimeric antigen receptor (CAR) of the invention comprising:
  an extracellular domain having an FN3 domain that specifically binds to a BCMA;
  a transmembrane domain; and
  an intracellular signaling domain.

The CAR can further comprise a signal peptide at the amino terminus and a hinge region connecting the extracellular domain and the transmembrane domain.

In some embodiments, the isolated polynucleotide encoding a CAR comprises:
  a signal peptide having an amino acid sequence that is at least 90% identical to SEQ ID NO: 2, preferably SEQ ID NO:2;
  an extracellular domain comprising an FN3 domain of the invention, such as an FN3 domain having an amino acid sequence that is at least 90% identical to one of SEQ ID NOs: 8-44 and 58-145, preferably one of SEQ ID NOs: 8-44 and 58-145;
  a hinge region having an amino acid sequence that is at least 90% identical to SEQ ID NO: 3, preferably SEQ ID NO:3;
  a transmembrane domain having an amino acid sequence that is at least 90% identical to SEQ ID NO: 4, preferably SEQ ID NO:4; and
  an intracellular signaling domain comprising a co-stimulatory domain having an amino acid sequence that is at least 90% identical to SEQ ID NO: 5, preferably SEQ ID NO:5, and a primary signaling domain having an amino acid sequence that is at least 90% identical to SEQ ID NO: 6, preferably SEQ ID NO:6.

In another general aspects, the invention relates to a CAR of the invention, a vector comprising a polynucleotide encoding a CAR of the invention, and a host cell comprising the vector or the isolated polynucleotide encoding a CAR of the invention. The invention also relates to a method of producing a CAR of the invention, comprising culturing a host cell comprising a polynucleotide sequence encoding the CAR under conditions to produce the CAR, and recovering the CAR. The CAR can be associated with the host cell or an isolated cell membrane from the host cell.

According to another general aspect, the invention relates to engineered immune cells comprising a CAR of the invention. Preferably, the engineered immune cells are T cell receptor knockout immune cells. Preferably, the engineered immune cells are HLA I/B2-microglobulin knockout immune cells. Optionally, the HLA I/B2-microglobulin knockout immune cells are additionally HLA II knockout immune cells that are devoid of allogeneic immune responses from the host patient. The engineered immune cells can comprise a second CAR having an extracellular domain binding specifically to a target different from BCMA. The engineered immune cells can also be resistant to at least one anti-cancer chemotherapy.

In another general aspect, the invention relates to pharmaceutical compositions comprising engineered immune cells of the invention.

In another general aspect, the invention relates to a method of treating a B cell-related condition in a subject in need thereof, comprising administering to the subject a therapeutically effective amount of a pharmaceutical composition of the invention. In a preferred embodiment, the B cell-related condition is multiple myeloma.

In another general aspect, the invention relates to a method of engineering an immune cell of the invention, comprising providing an immune cell, and introducing into the cell a polypeptide encoding a CAR of the invention.

In another general aspect, the invention relates to a method of producing a pharmaceutical composition, comprising combining an engineered immune cell of the invention with a pharmaceutically acceptable carrier to obtain the pharmaceutical composition Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings.

DETAILED DESCRIPTION OF THE INVENTION

Figure 1:
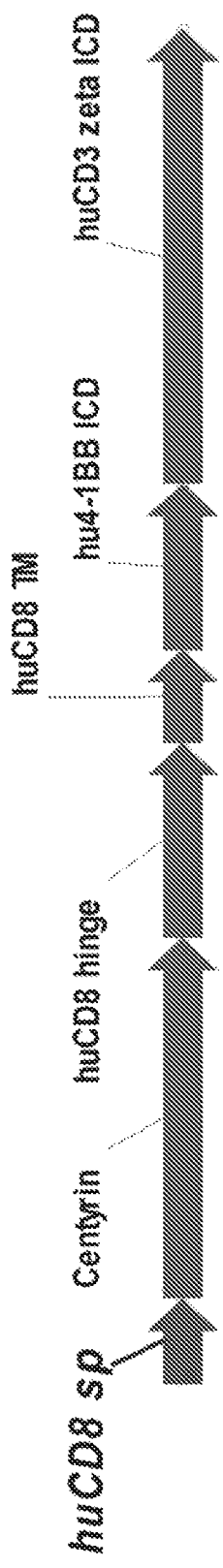
FIG. 1 shows the domain structure of a BCMA-targeting CAR according to an embodiment of the invention, where the signal peptide (huCD8 sp) at the N-terminal end is cleaved off in the mature CAR protein.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise stated, any numerical value, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

As used herein, the term "isolated" means a biological component (such as a nucleic acid, peptide or protein) has been substantially separated, produced apart from, or purified away from other biological components of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids.

An "isolated" FN3 domain, as used herein, is intended to refer to an FN3 domain which is substantially free of other FN3 domains having different antigenic specificities (for instance, an isolated FN3 domain that specifically binds to human BCMA is substantially free of FN3 domains that specifically bind antigens other than BCMA). An isolated FN3 domain that specifically binds to an epitope, isoform or variant of BCMA can, however, have cross-reactivity to other related antigens, for instance from other species (such as BCMA species homologs).

As used herein, the term "fibronectin type III domain" or "FN3 domain" refers to a domain occurring frequently in proteins including fibronectins, tenascin, intracellular cytoskeletal proteins, cytokine receptors and prokaryotic enzymes (Bork and Doolittle, PNAS USA 89:8990-8994, 1992; Meinke et al., J Bacteriol 175:1910-1918, 1993; Watanabe et al., J Biol Chem 265:15659-15665, 1990), or a derivative thereof. Exemplary FN3 domains are the 15 different FN3 domains present in human tenascin C, the 15 different FN3 domains present in human fibronectin (FN), and non-natural synthetic FN3 domains, for example, in U.S. Pat. No. 8,278,419. Individual FN3 domains are referred to by domain number and protein name, e.g., the 3$^{rd}$ FN3 domain of tenascin (TN3), or the 10th FN3 domain of fibronectin (FN10).

"Tencon" as used herein refers to a synthetic FN3 domain protein having the sequence shown in SEQ ID NO: 1 and described in US2010/0216708.

As used herein, the term "specifically binds" or "specific binding" refers to the ability of an FN3 domain of the invention to bind to a predetermined target with a dissociation constant ($K_D$) of about 1×10$^{-6}$ M or tighter, for example, about 1×10$^{-7}$ M or less, about 1×10$^{-8}$ M or less, about 1×10$^{-9}$ M or less, about 1×10$^{-10}$ M or less, about 1×10$^{-11}$ M or less, about 1×10$^{-12}$ M or less, or about 1×10$^{-13}$ M or less. The KD value can be determined using methods in the art in view of the present disclosure. For example, the KD of an FN3 domain protein can be determined by using surface plasmon resonance, such as by using a biosensor system, e.g., a Biacore® system or a Proteon Instrument (BioRad), or by using bio-layer interferometry technology, such as a Octet RED96 system. Typically, an FN3 domain binds to a predetermined target (i.e. human BCMA) with a $K_D$ that is at least ten fold less than its $K_D$ for a nonspecific target as measured by surface plasmon resonance using, for example, a Proteon Instrument (Bio-Rad). The FN3 domains that specifically bind to BCMA can, however, have cross-reactivity to other related targets, for example, to the same predetermined target from other species (homologs), such as *Macaca Fascicularis* (cynomolgous monkey, cyno) or Pan troglodytes (chimpanzee).

As used herein, the term "BCMA" refers to a B cell maturation antigen protein (also referred to as TNFRSF17, BCM or CD269), a tumor necrosis factor receptor (TNFR) family member that is expressed on plasma cells and on mature B cells.

For example, a human BCMA is a 184 amino acid-long protein encoded by a primary mRNA transcript 994 nucleotides long (NM_001192.2). The amino acid sequence of human BCMA is represented in GenBank Accession No. NP_001183.2. As used herein, the term "BCMA" includes proteins comprising mutations, e.g., point mutations, fragments, insertions, deletions and splice variants of full length wild type BCMA. The term "BCMA" also encompasses post-translational modifications of the BCMA amino acid sequence. Post-translational modifications include, but are not limited to, N- and O-linked glycosylation.

As used herein, a "BCMA-specific FN3 domain" refers to an FN3 domain that specifically binds to a BCMA.

As used herein, the term "randomizing" or "randomized" or "diversified" or "diversifying" refers to making at least one substitution, insertion or deletion in a polynucleotide or polypeptide sequence. As used herein, the term "library" refers to a collection of variants. The library can be composed of polypeptide or polynucleotide variants. As used herein, the term "variant" refers to a polypeptide or a polynucleotide that differs from a reference polypeptide or a reference polynucleotide by one or more modifications for example, substitutions, insertions or deletions. As used herein, the term "substituting" or "substituted" or "mutating" or "mutated" refers to altering, deleting or inserting one or more amino acids or nucleotides in a polypeptide or polynucleotide sequence to generate a variant of that sequence.

As used herein, a "Tencon library" refers to a collection of variants of Tencon. Molecules within a Tencon library are also referred to as "Centyrins."

As used herein, the term "chimeric antigen receptor" (CAR) refers to a recombinant polypeptide comprising at least an extracellular domain that binds specifically to an antigen or a target, a transmembrane domain and an intracellular T cell receptor-activating signaling domain. Engagement of the extracellular domain of the CAR with the target antigen on the surface of a target cell results in clustering of the CAR and delivers an activation stimulus to the CAR-containing cell. CARs redirect the specificity of immune effector cells and trigger proliferation, cytokine production, phagocytosis and/or production of molecules that can mediate cell death of the target antigen-expressing cell in a major histocompatibility (MHC)-independent manner.

As used herein, the term "signal peptide" refers to a leader sequence at the amino-terminus (N-terminus) of a nascent CAR protein, which co-translationally or post-translationally directs the nascent protein to the endoplasmic reticulum and subsequent surface expression.

As used herein, the term "extracellular antigen binding domain," "extracellular domain," or "extracellular ligand binding domain" refers to the part of a CAR that is located outside of the cell membrane and is capable of binding to an antigen, target or ligand.

As used herein, the term "hinge region" refers to the part of a CAR that connects two adjacent domains of the CAR protein, e.g., the extracellular domain and the transmembrane domain.

As used herein, the term "transmembrane domain" refers to the portion of a CAR that extends across the cell membrane and anchors the CAR to cell membrane.

As used herein, the term "intracellular T cell receptor-activating signaling domain", "cytoplasmic signaling domain," or "intracellular signaling domain" refers to the part of a CAR that is located inside of the cell membrane and is capable of transducing an effector signal.

As used herein, the term "stimulatory molecule" refers to a molecule expressed by a T cell that provides the primary cytoplasmic signaling sequence(s) that regulate primary activation of the T cell receptor (TCR) complex in a stimulatory way for at least some aspect of the T cell signaling pathway. Stimulatory molecules comprise two distinct classes of cytoplasmic signaling sequence, those that initiate antigen-dependent primary activation (referred to as "primary signaling domains"), and those that act in an antigen-independent manner to provide a secondary of co-stimulatory signal (referred to as "co-stimulatory signaling domains").

As used herein, the term "polynucleotide," synonymously referred to as "nucleic acid molecule," "nucleotides" or "nucleic acids," refers to any polyribonucleotide or polydeoxyribonucleotide, which can be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

As used herein, the term "vector" is a replicon in which another nucleic acid segment can be operably inserted so as to bring about the replication or expression of the segment.

As used herein, the term "host cell" refers to a cell comprising a nucleic acid molecule of the invention. The "host cell" can be any type of cell, e.g., a primary cell, a cell in culture, or a cell from a cell line. In one embodiment, a "host cell" is a cell transfected with a nucleic acid molecule of the invention. In another embodiment, a "host cell" is a progeny or potential progeny of such a transfected cell. A progeny of a cell may or may not be identical to the parent cell, e.g., due to mutations or environmental influences that can occur in succeeding generations or integration of the nucleic acid molecule into the host cell genome.

The term "expression" as used herein, and refer to the biosynthesis of a gene product. The term encompasses the transcription of a gene into RNA. The term also encompasses translation of RNA into one or more polypeptides, and further encompasses all naturally occurring post-transcriptional and post-translational modifications. The expressed FN3 domain or CAR can be within the cytoplasm of a host cell, into the extracellular milieu such as the growth medium of a cell culture, or anchored to the cell membrane.

As used herein, the term "immune cell" or "immune effector cell" refers to a cell that is involved in an immune response, e.g., in the promotion of an immune effector response. Examples of immune cells include T cells, B cells, natural killer (NK) cells, mast cells, and myeloid-derived phagocytes. According to particular embodiments, the engineered immune cells are T cells, and are referred to as CAR-T cells because they are engineered to express CARs of the invention.

As used herein, the term "engineered immune cell" refers to an immune cell, also referred to as an immune effector cell, that has been genetically modified by the addition of extra genetic material in the form of DNA or RNA to the total genetic material of the cell. According to embodiments herein, the engineered immune cells have been genetically modified to express a BCMA-targeting CAR according to the invention.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention.

As used herein, the term "subject" refers to an animal, and preferably a mammal. According to particular embodiments, the subject is a mammal including a non-primate (e.g., a camel, donkey, zebra, cow, pig, horse, goat, sheep, cat, dog, rat, rabbit, guinea pig or mouse) or a primate (e.g., a monkey, chimpanzee, or human). In particular embodiments, the subject is a human.

As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein, the terms "treat," "treating," and "treatment" are all intended to refer to an amelioration or reversal of at least one measurable physical parameter related to a cancer or autoimmunity, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

FN3 Sequence-Based Libraries

Tencon is a non-naturally occurring FN3 domain designed from a consensus sequence of fifteen FN3 domains from human tenascin-C (Jacobs et al., Protein Engineering, Design, and Selection, 25:107-117, 2012; US2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, PNAS USA 89:8990-8992, 1992; U.S. Pat. No. 6,673,901). These loops, or selected residues within each loop, can be randomized in order to construct libraries of FN3 domains that can be used to select novel molecules that bind BCMA. Table 1 shows positions and sequences of each loop and beta-strand in Tencon (SEQ ID NO: 1).

TABLE 1

| FN3 domain | Tencon (SEQ ID NO: 1) |
|---|---|
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Libraries designed based on the Tencon sequence can thus have randomized sequence in one or more of the loops or strands. For example, libraries based on Tencon can have randomized sequence in one or more of the AB loop, BC loop, CD loop, DE, EF loop and FG loop. For example, the Tencon BC loop is 7 amino acids long, thus 1, 2, 3, 4, 5, 6 or 7 amino acids can be randomized in a library based on Tencon sequence, diversified at the BC loop. The Tencon CD loop is 6 amino acids long, thus 1, 2, 3, 4, 5 or 6 amino acids can be randomized in a library based on Tencon sequence, diversified at the CD loop. The Tencon EF loop is 5 amino acids long, thus 1, 2, 3, 4 or 5 amino acids can be randomized in a library based on Tencon sequence, diversified at the EF loop. The Tencon FG loop is 7 amino acids long, thus 1, 2, 3, 4, 5, 6 or 7 amino acids can be randomized in a library based on Tencon sequence, diversified at the FG loop. Further diversity at loops in the Tencon libraries can be achieved by insertion and/or deletions of residues at loops. For example, the BC, CD, EF and/or FG loops can be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop can be diversified in sequence as well as in length to correspond to the antibody CDR3 length range of 4-28 residues. For example, the FG loop can be further diversified in length by extending the loop by an additional 1, 2, 3, 4 or 5 amino acids.

Libraries designed based on the Tencon sequence can also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface is described in US2013/0226834. Libraries designed based on the Tencon sequence also includes libraries designed based on Tencon variants, such as Tencon variants having substitutions at residues positions 11, 17, 46 and/or 86 (residue numbering corresponding to SEQ ID NO: 1), and which variants display improve thermal stability. Exemplary Tencon variants are described in US2011/0274623, and include Tencon27 (SEQ ID NO: 45) having substitutions E11R, L17A, N46V and E86I when compared to Tencon of SEQ ID NO: 1.

Tencon libraries and other FN3 sequence-based libraries can be randomized at chosen residue positions using a random or defined set of amino acids. For example, variants in the library having random substitutions can be generated using NNK codons, which encode all 20 naturally occurring amino acids. In other diversification schemes, DVK codons can be used to encode amino acids Ala, Trp, Tyr, Lys, Thr, Asn, Lys, Ser, Arg, Asp, Glu, Gly, and Cys. Alternatively, NNS codons can be used to give rise to all 20 amino acid residues while simultaneously reducing the frequency of stop codons. Libraries of FN3 domains with biased amino acid distribution at positions to be diversified can be synthesized, for example, using Slonomics® technology (http:_//www_sloning_com). This technology uses a library of pre-made double stranded triplets that act as universal building blocks sufficient for thousands of gene synthesis processes. The triplet library represents all possible sequence combinations necessary to build any desired DNA molecule. The codon designations are according to the well known IUB code.

BCMA-Specific FN3 Domains and Uses Thereof

In one general aspect, the invention relates to an isolated FN3 domain that specifically binds to a BCMA.

According to embodiments of the invention, the isolated FN3 domain specifically binds to the extracellular domain of BCMA, such as a sequence within residues 1 to 54 of the human BCMA.

In some embodiments, the isolated BCMA-specific FN3 domain comprises an initiator methionine (Met) linked to the N-terminus of the molecule.

In some embodiments, an isolated FN3 domain comprises an amino acid sequence that is at least 80%, 85%, 90% or 95% identical to SEQ ID NO: 1, and the FN3 domain binds to a BCMA, preferably a human BCMA, with a KD less than $1\times10^{-7}$ M as determined by using surface plasmon resonance. For example, the FN3 domain binds to a human BCMA with a KD less than $1\times10^{-6}$ M, $5\times10^{-7}$ M, $1\times10^{-7}$ M, $5\times10^{-8}$ M, $1\times10^{-8}$ M, $5\times10^{-9}$ M, $1\times10^{-9}$ M, $5\times10^{-10}$ M, $1\times10^{-10}$ M, $5\times10^{-11}$ M, $1\times10^{-11}$ M, $5\times10^{-12}$ M, $1\times10^{-12}$ M, $5\times10^{-13}$ M or $1\times10^{-13}$ M as determined by using a biosensor system, e.g., a Proteon Instrument (BioRad).

In some other embodiments, an isolated FN3 domain specifically binding to a BCMA, preferably a human BCMA, comprises an amino acid sequence that is at least 80%, 85%, 90% or 95% identical to SEQ ID NO:7.

According to other embodiments of the invention, an isolated FN3 domain comprises an amino acid sequence that is at least 90% identical to one selected from the group consisting of SEQ ID NOs: 8-44 and 58-145, wherein the FN3 domain specifically binds to a BCMA, preferably a human BCMA. In some embodiments, the isolated BCMA-specific FN3 domain has 1, 2, 3, 4, 5, 6, 7, 8, 9, 10, 11, 12, 13 or 14 substitutions when compared to the amino acid sequence of one of SEQ ID NOs: 8-44 and 58-145. Preferably, the isolated FN3 domain comprises one of the amino acid sequences of SEQ ID NOs: 8-44 and 58-145.

In certain embodiments, a BCMA-specific FN3 domain can comprise a variant of the sequence as set forth in one of SEQ ID NOs: 8-44 and 58-145, wherein the A-strand, B-strand, BC loop, C-strand, CD loop, D-strand, EF loop, F-strand, FG-loop and/or G loop are replaced with a respective set of A-strand, B-strand, BC loop, C-strand, CD loop, D-strand, EF loop, F-strand, FG-loop and/or G loop sequences from any of the described BCMA-specific FN3 domain sequences (i.e., SEQ ID NOs: 8-44 and 58-145), or sequences at least 85%, 90%, 95%, 96%, 97%, 98%, or 99% identical to the A-strand, B-strand, BC loop, C-strand, CD loop, D-strand, EF loop, F-strand, FG-loop and/or G loop sequences from any of the described BCMA-specific FN3 domain sequences (i.e., SEQ ID NOs: 8-44 and 58-145).

The FN3 domains specifically binding to a BCMA, such as a human BCMA, according to embodiments of the invention, can be generated using any FN3 domain as a template to generate a library and screening the library for molecules specifically binding to the BCMA using methods known to those skilled in the art in view of the present disclosure. Exemplary FN3 domains that can be used are the $3^{rd}$ FN3 domain of tenascin C (TN3), Fibcon, and the $10^{th}$ FN3 domain of fibronectin (FN10). See, e.g., U.S. Pat. No. 9,200,273.

Standard cloning and expression techniques are used to clone the libraries into a vector or synthesize double stranded cDNA cassettes of the library, to express, or to translate the libraries in vitro. For example, ribosome display (Hanes and Pluckthun, PNAS USA, 94, 4937-4942, 1997), mRNA display (Roberts and Szostak, PNAS USA, 94, 12297-12302, 1997), or other cell-free systems (U.S. Pat. No. 5,643,768) can be used. The libraries of the FN3 domain variants can be expressed as fusion proteins displayed on the surface, for example, of any suitable bacteriophage. Methods for displaying fusion polypeptides on the surface of a bacteriophage are well known (US2011/0118144, WO2009/085462, U.S. Pat. Nos. 6,969,108, 6,172,197, 5,223,409, 6,582,915, 6,472,147).

According to an embodiment of the invention, an FN3 domain specifically binding to a human BCMA can be isolated by producing an FN3 library, such as a Tencon library, using cis display to ligate DNA fragments encoding the FN3 scaffold proteins to a DNA fragment encoding RepA to generate a pool of protein-DNA complexes formed after in vitro translation, wherein each protein is stably associated with the DNA that encodes it (U.S. Pat. No. 7,842,476; Odegrip et al., PNAS USA 101, 2806-2810, 2004), and assaying the library for specific binding to the human BCMA, by any method known in the art and as described in the Examples.

Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains specifically binding to the human BCMA are further characterized according to the desired characteristics. FN3 domains specifically binding to a BCMA, such as a human BCMA, can be modified to improve their properties, such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr Opin Biotechnol, 12, 371-375, 2001). High thermal stability can increase the yield of the expressed protein, improve solubility or activity, decrease immunogenicity, and minimize the need of a cold chain in manufacturing.

Residues that can be substituted to improve thermal stability of Tencon (SEQ ID NO: 1) include, but are not limited to, one or more residues at positions 11, 14, 17, 37, 46, 73, and 86 of SEQ ID NO:1, as described in US2011/0274623, which is incorporated herein by reference. Substitutions corresponding to these residues can be incorporated to the FN3 domain according to embodiment of the invention.

An FN3 domain specifically binding to a BCMA, such as a human BCMA, according to embodiments of the invention can be used for therapeutic purpose, diagnostic purpose or any other purposes where specific binding to a BCMA is desired. For example, the FN3 domain can be used for diagnostic purpose to detect the presence or quantify the level of a BCMA in a biological sample. The FN3 domain can also be used for therapeutic purpose to prevent or treat a disease or disorder associated with a BCMA, such as those disclosed herein. In some embodiments, the invention also relates to a pharmaceutical composition comprising a FN3 domain of the invention and a pharmaceutically acceptable carrier, such as those disclosed herein. The FN3 domain could further be used together with one or more other components, for example, in the extracellular domain of a CAR according to the invention.

BCMA-Targeting Chimeric Antigen Receptors (CARs)

In other general aspects, the invention relates to a BCMA-targeting CAR comprising a BCMA-specific FN3 domain.

In one aspect, the invention relates to a CAR comprising:
an extracellular domain having an FN3 domain that specifically binds to a BCMA;
a transmembrane domain; and
an intracellular signaling domain.

In some embodiments, in a nascent CAR, the extracellular domain is preceded by a signal peptide at the N-terminus. Any suitable signal peptide can be used in the invention. The signal peptide can be derived from a natural, synthetic, semi-synthetic or recombinant source. According to one embodiment, the signal peptide is a human CD8 signal peptide, a human CD3 delta signal peptide, a human CD3 epsilon signal peptide, a human GMCSFR signal peptide, a human 41-BB signal peptide, or a derivative thereof. According to particular embodiments, the signal peptide has an amino acid sequence at least 90% identical to SEQ ID NO: 2, preferably the amino acid sequence of SEQ ID NO: 2. According to other particular embodiments, the signal peptide has an amino acid sequence at least 90% identical to one of SEQ ID NOs: 50-53, preferably the amino acid sequence of one of SEQ ID NOs: 50-53. The signal peptide can be cleaved by a signal peptidase during or after completion of translocation to generate a mature CAR free of the signal peptide.

According to embodiments of the invention, the extracellular domain of a CAR comprises a BCMA-specific FN3 domain. Any BCMA-specific FN3 domain according to embodiments of the invention, including but not limited to those described herein, can be used in the extracellular domain of the CAR.

According to embodiments of the invention, a CAR can further comprise a hinge region connecting the extracellular domain and the transmembrane domain. The hinge region functions to move the extracellular domain away from the surface of the engineered immune cell to enable proper cell/cell contact, binding to the target or antigen and activation (Patel et al., Gene Therapy, 1999; 6: 412-419). Any suitable hinge region can be used in a CAR of the invention. It can be derived from a natural, synthetic, semi-synthetic or recombinant source. According to some embodiments, the hinge region of the CAR is a 6×GS peptide, or a fragment thereof, or a hinge region from a CD8 protein, or a derivative thereof. In particular embodiments, the hinge region has an amino acid sequence at least 90% identical to SEQ ID NO: 3, preferably the amino acid sequence of SEQ ID NO: 3.

Any suitable transmembrane domain can be used in a CAR of the invention. The transmembrane domain can be derived from a natural, synthetic, semi-synthetic or recombinant source. According to some embodiments, the transmembrane domain is a transmembrane domain from molecules such as CD8, CD28, CD4, CD2, GMCSFR and the like. In particular embodiments, the transmembrane domain has an amino acid sequence at least 90% identical to SEQ ID NO: 4, preferably the amino acid sequence of SEQ ID NO: 4. In other embodiments, the transmembrane domain has an amino acid sequence at least 90% identical to one of SEQ ID NOs: 54-57, preferably the amino acid sequence of one of SEQ ID NOs: 54-57.

Any suitable intracellular signaling domain can be used in a CAR of the invention. In particular embodiments, the entire intracellular signaling domain is used. In other particular embodiments, a truncated portion of the signaling domain that transduces the effector signal is used. According to embodiments of the invention, the intracellular signaling domain generates a signal that promotes an immune effector function of the CAR-containing cell, e.g. a CAR-T cell, including, but not limited to, proliferation, activation, and/or differentiation. In particular embodiments, the signal promotes, e.g., cytolytic activity, helper activity, and/or cytokine secretion of the CAR-T cell.

According to some embodiments, the intracellular signaling domain comprises a functional signaling domain derived from CD3 zeta, TCR zeta, FcR gamma, FcR beta, CD3 gamma, CD3 delta, CD3 epsilon, CD16, CD22, CD27, CD28, CD30, CD79a, CD79b, CD134 (also known as TNFRSF4 or OX-40), 4-1BB (CD137), CD278 (also known as ICOS), FcεRI, DAP10, DAP12, ITAM domains or CD66d, and the like.

According to particular embodiments, the intracellular signaling domain comprises a primary signaling domain and one or more co-stimulatory signaling domains.

In one embodiment, the intracellular signaling domain comprises a primary intracellular signaling domain having a functional signaling domain derived from human CD3zeta. In particular embodiments, the primary intracellular signaling domain has an amino acid sequence at least 90% identical to SEQ ID NO: 6, preferably the amino acid sequence of SEQ ID NO: 6.

According to some embodiments, the intracellular signaling domain further comprises the co-stimulatory intracellular signaling domain derived from human 4-1BB. In particular embodiments, the co-stimulatory intracellular signaling domain has an amino acid sequence at least 90% identical to SEQ ID NO: 5, preferably the amino acid sequence of SEQ ID NO: 5.

In one embodiment, the intracellular signaling domain has an amino acid sequence at least 90% identical to SEQ ID NO: 49, preferably the amino acid sequence of SEQ ID NO: 49.

In particular embodiments, a CAR has the structure shown in FIG. 1, comprising, from the N-terminus to the C-terminus, a BCMA-specific FN3 domain (Centyrin), a human CD8 hinge region, a human CD8 transmembrane region, a human 4-1BB intracellular domain, and a human CD3 zeta intracellular domain. The nascent CAR further comprises a human CD8 signal peptide, which is subsequently cleaved in the mature CAR.

In one embodiment, a CAR of the invention is associated with a host cell expressing the CAR.

In another embodiment, a CAR of the invention is present in an isolated cell membrane of the host cell expressing the CAR.

In yet another embodiment, a CAR of the invention is purified or isolated from other components of the host cell expressing the CAR.

Polynucleotides, Vectors and Host Cells

In other general aspects, the invention relates to isolated polynucleotides and vectors encoding FN3 domains or CARs of the invention, and recombinant cells containing the vectors.

Nucleic acids encoding any of the various proteins or polypeptides disclosed herein can be synthesized chemically or using other methods in the art in view of the present disclosure. Codon usage can be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., PNAS USA. 2003 100(2):438-42; Sinclair et al. Protein Expr Purif 2002 (1):96-105; Connell, Curr Opin Biotechnol. 2001 (5):446-9; Makrides et al. Microbiol Rev. 1996 60(3):512-38; and Sharp et al. Yeast. 1991 7(7):657-78.

General techniques for nucleic acid manipulation are within the purview of one skilled in the art and are also described, for example, in Sambrook et al., Molecular Cloning: A Laboratory Manual, Vols. 1-3, Cold Spring Harbor Laboratory Press, 2 ed., 1989, or Ausubel et al., eds., 1994, Current Protocols in Molecular Biology, Vol. 1, John Wiley & Sons, Inc., New York, and periodic updates, herein incorporated by reference. The DNA encoding a protein is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated. Suitable regulatory elements are well-known in the art.

It will be appreciated by those skilled in the art that the coding sequence of a protein can be changed without changing the amino acid sequence of the protein. Accordingly, it will be understood by those skilled in the art that nucleic acid sequences encoding FN3 domains or CARs of the invention can be altered without changing the amino acid sequences of the proteins.

In one embodiments, the invention relates to a vector comprising an isolated nucleic acid encoding an FN3 domain or a CAR of the invention. Any vector known to those skilled in the art in view of the present disclosure can be used, such as a plasmid, cosmid, a phage vector or a viral vector. In one embodiment, the vector is an expression vector comprising a polynucleotide sequence encoding an FN3 domain or a CAR of the invention operably linked to a promoter sequence, optionally one or more other regulatory sequences.

In another embodiment, the invention relates to transient expression of a CAR of the invention by an mRNA encoding the CAR. In one aspect, the mRNA encoding the CAR is introduced into an immune effector cell as a form of transient transfection, wherein the expression of the non-integrated transgene is expressed for a period of hours, days or weeks, wherein the period of time of expression is less than the period of time for expression of the gene if integrated into the genome or contained within a stable plasmid replicon in the host cell. In one aspect, the mRNA is produced by in vitro transcription using a PCR-generated template.

In another general aspect, the invention relates to a host cell comprising an isolated nucleic acid encoding an FN3 domain or a CAR of the invention. The host cell can be stably or transiently transfected with a nucleic acid molecule of the invention. Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, can also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). In some instances, it will be desired to produce proteins in vertebrate cells, such as for glycosylation, and the propagation of vertebrate cells in culture (tissue culture) has become a routine procedure. Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines.

A host cell of the invention can be an engineered BCMA-targeting immune cell, which is described in detail infra.

Protein Production

In another general aspect, the invention relates to a method of producing a FN3 domain of the invention, comprising culturing a host cell comprising a nucleic acid encoding the FN3 domain under conditions to produce the FN3 domain of the invention, and recovering the FN3 domain from the cell or cell culture (e.g., from the supernatant). Expressed FN3 domains can be harvested from the cells or cell culture and purified according to conventional techniques known in the art in view of the present disclosure.

In another general aspect, the invention relates to a method of producing a CAR of the invention, comprising culturing a host cell comprising a nucleic acid encoding the CAR under conditions to produce the CAR of the invention, and recovering the CAR. Expressed CARs can be harvested from the cells and purified according to conventional techniques known in the art and as described herein.

Host cells are transformed with the expression or cloning vectors for protein production and cultured in conventional nutrient media modified as appropriate, e.g., for inducing promoters, selecting transformants, or amplifying the genes encoding the desired sequences.

The host cells used to produce the proteins of this invention can be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al, Meth. Enz. 58:44 (1979); Barnes et al, Anal. Biochem. 102:255 (1980); U.S. Pat. Nos. 4,767,704; 4,657,866; 4,927,762; 4,560,655; 5,122,469; WO90/03430; WO87/00195 or U.S. Pat. No. RE30985 can be used as culture media for the host cells. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements can also be included at appropriate concentrations that would be known to those skilled in the art. The culture conditions, such as temperature, pH, and the like, are those previously used with the host cell selected for expression, and will be apparent to the ordinarily skilled artisan.

Proteins disclosed herein can also be produced using cell-translation systems in vitro. For such purposes, the nucleic acids encoding the proteins must be modified to allow in vitro transcription to produce mRNA and to allow cell-free translation of the mRNA in the particular cell-free system being utilized. Exemplary eukaryotic cell-free translation systems include, for example, mammalian or yeast cell-free translation systems, and exemplary prokaryotic cell-free translation systems include, for example, bacterial cell-free translation systems.

Proteins disclosed herein can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, proteins can be exchanged into different buffers and/or concentrated by any of a variety of methods known to the art, including, but not limited to, filtration and dialysis.

The purified proteins are preferably at least 85% pure, more preferably at least 95% pure, and most preferably at least 98% pure.

Engineered BCMA-Targeting CAR-T Cells, Compositions and Methods Thereof

In another general aspect, the invention relates to engineered BCMA-targeting immune cells comprising a BCMA-targeting CAR of the invention, methods of making the engineered immune cells, compositions comprising the engineered immune cells, and methods of using the engineered immune cells to treat diseases such as multiple myeloma.

In one general aspect, the invention relates to engineered immune cells comprising BCMA-targeting CARs of the invention.

According to some embodiments, the immune cell can be made less allogeneic, for instance, by inactivating at least one gene expressing one or more component of T cell receptor (TCR) as described in WO 2013/176915, which can be combined with the inactivation of a gene encoding or regulating HLA I/B2-microglobulin (B2M) protein expression. Accordingly, the risk of graft versus host syndrome and graft rejection is significantly reduced. A T cell lacking a functional TCR, referred to as a "TCR knockout" or a "TCR-KO" cell, can be engineered such that it does not express any functional TCR on its surface, engineered such that it does not express one or more subunits that comprise a functional TCR (e.g., engineered such that it does not express (or exhibits reduced expression) of TCR alpha, TCR beta, TCR gamma, TCR delta, TCR epsilon, and/or TCR zeta) or engineered such that it produces very little functional TCR on its surface. Alternatively, the T cell can express a substantially impaired TCR (i.e., a TCR that will not elicit an adverse immune reaction in a host), e.g., by expression of mutated or truncated forms of one or more of the subunits of the TCR. Modified T cells that lack expression of a functional TCR and/or B2M can be obtained by any suitable means, including a knock out or knock down of one or more subunit of TCR and/or B2M. For example, the T cell can include a knock down of TCR and/or B2M using siRNA, shRNA, clustered regularly interspaced short palindromic repeats (CRISPR), transcription-activator like effector nuclease (TALEN), megaTAL, meganuclease, or zinc finger endonuclease (ZFN).

In particular embodiments, the immune effector cell comprising a BCMA-targeting CAR of the invention is a T cell, a NKT cell or a NK cell, preferably, a human T cell or human NK cell, more preferably a TCR knockout cell, most preferably a human TCR knockout cell and/or an HLA I/B2M knockout cell. In other embodiments, the immune effector cell comprising a BCMA-targeting CAR of the invention is an engineered T cell line, such as a TALL-104 T cell line (i.e., a IL-2-dependent human non-restricted cytotoxic T cell line that expresses CD8 and CD3 but not CD16).

Immune effector cells of the invention can be autologous (i.e., "self," e.g., autogenic) or non-autologous (i.e., "non-self," e.g., allogenic, syngenic, xenogenic). Autologous refers to any material derived from the same individual into whom it is later to be re-introduced. Non-autologous refers to any material derived from a different individual of the same species as the individual into whom the material is later to be introduced In another general aspect, the invention relates to methods of making the engineered BCMA-targeting immune cells comprising BCMA-targeting CARs of the invention. A vector encoding the CAR can be directly transduced into an immune cell. Alternatively, in vitro transcribed RNA or synthetic RNA encoding the CAR can be introduced into an immune cell.

According to particular embodiments, the method of making the engineered BCMA-targeting immune cells comprises transfecting or transducing immune effector cells isolated from an individual such that the immune effector cells express one or more CAR(s) according to embodiments of the invention. Methods of preparing immune cells for immunotherapy are described, e.g., in WO2014/130635, WO2013/176916 and WO2013/176915, which are incorporated herein by reference. Individual steps that can be used for preparing engineered immune cells are disclosed, e.g., in WO2014/039523, WO2014/184741, WO2014/191128, WO2014/184744 and WO2014/184143, which are incorporated herein by reference.

In a particular embodiment, the immune effector cells, such as T cells, are genetically modified with CARs of the invention (e.g., transduced with a viral vector comprising a nucleic acid encoding a CAR) and then are activated and expanded in vitro. In various embodiments, T cells can be activated and expanded before or after genetic modification to express a CAR, using methods as described, for example, in U.S. Pat. Nos. 6,352,694, 6,534,055, 6,905,680, 6,692, 964, 5,858,358, 6,887,466, 6,905,681, 7,144,575, 7,067,318, 7,172,869, 7,232,566, 7,175,843, 5,883,223, 6,905,874, 6,797,514, 6,867,041, US2006/121005, which are incorporated herein by reference. T cells can be expanded in vitro or in vivo. Generally, the T cells of the invention can be expanded by contact with a surface having attached thereto an agent that stimulates a CD3/TCR complex-associated signal and a ligand that stimulates a co-stimulatory molecule on the surface of the T cells. As non-limiting examples, T cell populations can be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore, or by activation of the CAR itself. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include, e.g., an appropriate media (e.g., Minimal Essential Media or RPMI Media 1640 or, X-vivo 5 (Lonza)) that can contain factors necessary for proliferation and viability, including serum (e.g., fetal bovine or human serum), cytokines, such as IL-2, IL-7, IL-15, and/or IL-21, insulin, IFN-g, GM-CSF, TGFb and/or any other additives for the growth of cells known to the skilled artisan. In other embodiments, the T cells can be activated and stimulated to proliferate with feeder cells and appropriate antibodies and cytokines using methods such as those described in U.S. Pat. Nos. 6,040,177, 5,827,642, and WO2012129514, which are incorporated herein by reference.

In some embodiments, a CAR-expressing cell of the invention can further comprise a second CAR having an extracellular domain that specifically binds to the same target or a different target. Preferably, the immune cell expresses two CARs that specifically bind to two different targets, or the immune cell expresses a bispecific receptor, such as a CAR comprising two FN3 domains that specifically bind to two different targets, i.e., a BCMA and another target, associated with the same disease of interest. For example, the other target can also be associated with multiple myeloma, such as CD19, CD20, CS-1, kappa light chain, CD138, Lewis Y antigen, or CD38 (Garfall et al., Discovery Medicine, 2014, 17(91):37-46)). More preferably, the two CARs also have different intracellular signaling domains, for example, the first CAR has a costimulatory signaling domain but not a primary signaling domain, and the second CAR has a primary signaling domain but not a costimulatory signaling domain, or vice versa. By the placement of a costimulatory signaling domain, such as that from 4-1BB, CD28, CD27 ICOS, or OX-40, onto one CAR, and the primary signaling domain, such as that from CD3 zeta, on the other CAR, one can limit the CAR activity to cells where both targets are expressed, e.g., for enhanced specificity.

In some embodiments, a CAR-expressing cell of the invention can further comprise an inhibitory CAR as a self-regulating safety switch to constrain T cell-based therapies and avoid off-tumor toxicity. For example, the inhibitory CAR can include an extracellular domain that binds specifically to a target found on normal cells but not on the target cancer cells. The inhibitory CAR also includes an intracellular domain having an inhibitory receptor signaling domain, such as an intracellular domain of an inhibitory molecule including, but not limited to, PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, and TGFR beta. Cells expressing a BCMA-targeting CAR and an inhibitory CAR are suppressed when encountering a normal cell, but activated when encountering a tumor cell not expressing the normal cell target.

In some other embodiments, a CAR-expressing cell of the invention can further comprise an agent that enhances the activity of a CAR-expressing cell. For example, the agent can inhibit the activity of an inhibitory molecule, such as those described herein, in the host cell.

According to particular embodiments, the engineered immune CAR-expressing cells are further genetically engineered to be resistant to at least one anti-cancer chemotherapy. This drug resistance can allow the engineered immune cells to survive in the presence of drugs while selectively targeting BCMA-expressing cells.

According to some embodiments, drug resistance can be conferred on the CAR-expressing cells by genetically engineering them to express at least one drug resistance gene. A drug resistance gene of the invention can encode resistance to anti-metabolite, methotrexate, vinblastine, cisplatin, alkylating agents, anthracyclines, cytotoxic antibiotics, anti-immunophilins, their analogs or derivatives, etc. Several drug resistance genes have been identified that can be used to confer drug resistance to engineered immune CAR-expressing cells of the invention. See, e.g., Takebe et al., Mol Ther. 2001 January; 3(1):88-96.; Sugimoto et al, J Gene Med. 2003 May; 5(5):366-76; Zielske et al., J Clin Invest. 2003 November; 112(10):1561-70; Nivens et al, Cancer Chemother Pharmacol. 2004 February; 53(2):107-15; Bardenheuer et al., Leukemia. 2005 December; 19(12): 2281-8; Kushman et al., Carcinogenesis. 2007 January; 28(1):207-14. Examples of drug resistance genes that can be expressed in the cells include a mutant or modified form of Dihydrofolate reductase (DHFR), a mutant or modified form of ionisine-5'-monophosphate dehydrogenase II (IMPDH2), multidrug resistance protein 1 (MDR1), calcineurin, methylguanine transferase (MGMT), microRNA-21, the antibiotic resistance genes ble and mcrA, etc. According to particular embodiments, said drug resistance genes can be expressed in the cell by any suitable means, including, e.g., introducing a transgene encoded by at least one vector into a cell.

Resistance to anti-cancer chemotherapies can also be conferred, e.g., by inactivating genes that are responsible for the cell's sensitivity to the drug. Examples of genes that can be inactivated to confer drug resistance to the cells include, e.g., CD52, glucocorticoid receptors, CD3, human hypoxanthine-guanine phosphoribosyl transferase (HPRT), human deoxycytidine kinase (dCK), etc. Genes responsible for the cell's sensitivity to anti-cancer drugs can be inactivated by any suitable means, including a knock out or knock down of the gene, e.g., using siRNA, shRNA, CRISPR, TALEN, or ZFN.

In another general aspect, the invention relates to a pharmaceutical composition, comprising an engineered BCMA-targeting immune cell of the invention and a pharmaceutically acceptable carrier. In view of the present disclosure, any pharmaceutically acceptable carrier suitable for use in CAR-T pharmaceutical composition can be used in the invention.

In another general aspect, the invention relates to a method of treating a B cell-related disease in a subject in need thereof, comprising administering to the subject a therapeutically effective amount of a pharmaceutical composition of the invention. B cell-related diseases include diseases, disorders or conditions associated with inappropriate B cell activity and B cell malignancies, e.g., proliferative diseases such as a cancer or malignancy, precancerous conditions, or non-cancer conditions associated with cells that express BCMA. According to particular embodiments, the invention relates to a method of treating multiple myeloma in a subject in need thereof, comprising administering to the subject a pharmaceutical composition of the invention.

According to embodiments of the invention, a therapeutically effective amount of the pharmaceutical composition stimulates an immune response in a subject in need thereof, preferably results in treatment of a disease, disorder, or condition; prevents or slows the progression of the disease, disorder, or condition; or reduces or completely alleviates symptoms associated with the immune disease, disorder, or condition.

According to particular embodiments, the disease, disorder or condition to be treated is a hyperproliferative disease. According to other particular embodiments, the disease, disorder or condition to be treated is a cancer or tumor, or a malignant hyperproliferative disease, preferably a cancer selected from the group consisting of a solid tumor, a hematologic cancer, bladder cancer, biliary cancer, brain cancer, breast cancer, colon cancer, esophageal cancer, gastric cancer, glioma, head cancer, leukemia, liver cancer, lung cancer, lymphoma, multiple myeloma, neck cancer, ovarian cancer, melanoma, pancreatic cancer, renal cancer, salivary cancer, stomach cancer, thymic epithelial cancer, and thyroid cancer. Preferably, the disease, disorder or condition to be treated is cancer or malignancy, or a precancerous condition chosen from one or more of a myelodysplasia, a myelodysplastic syndrome or a preleukemia.

According to some embodiments, the disease, disorder or condition to be treated is an acute leukemia chosen from one or more of B-cell acute lymphoid leukemia (BALL), T-cell acute lymphoid leukemia (TALL), acute lymphoid leukemia (ALL); chronic myelogenous leukemia (CML), chronic lymphocytic leukemia (CLL); B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia; a prostate cancer, pancreatic cancer, lung cancer; or a plasma cell proliferative disorder, monoclonal gammapathy of undetermined significance (MGUS), Waldenstrom's macroglobulinemia, a plasmacytoma, systemic amyloid light chain amyloidosis, and POEMS syndrome, or a combination thereof.

According to an embodiment, the disease, disorder or condition to be treated is multiple myeloma. According to particular embodiments, the multiple myeloma is selected from the group consisting of overt multiple myeloma, smoldering multiple myeloma, plasma cell leukemia, non-secretory myeloma, IgD myeloma, osteosclerotic myeloma, solitary plasmacytoma of bone, and extramedullary plasmacytoma.

According to particular embodiments, a therapeutically effective amount of the BCMA-targeting immune cell composition is sufficient to achieve one, two, three, four, or more of the following effects in a subject in need thereof: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy. In particular embodiments, a therapeutically effective amount refers to the amount of therapy which is sufficient to achieve one, two, three, four, or more of the following effects: (i) decrease the tumor volume; (ii) decrease the number of tumor cells; (iii) decrease the number of metastases; (iv) increase the life expectancy; (v) decrease tumor cell proliferation; (vi) decrease tumor cell survival; (vii) ameliorate physiological symptoms associated with the cancerous condition; and/or (viii) prevent the occurrence of tumor.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy. The exact dose can be ascertained by one skilled in the art using known techniques. In general, the BCMA-targeting immune cells are administered at a dose of about $10^5$ to $10^8$ cells/kg body weight. According to some embodiments, the total dose of cells can be administered to the subject by dose fractionation, e.g., one, two, three or more separate administration of a partial dose.

According to particular embodiments, the compositions described herein are formulated to be suitable for the intended route of administration to a subject. For example, the compositions described herein can be formulated to be suitable for intravenous, subcutaneous, or intramuscular administration.

According to particular embodiments, a composition used in the treatment of a cancer can be used in combination with another treatment including, but not limited to, a chemotherapy, a lympho-depleting therapy, a radiation therapy, other immune-oncology drug, a targeted therapy, a cancer vaccine, or other anticancer drugs.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of redirecting immune cells to target their killing of BCMA-presenting cells in a subject in need thereof, comprising administering to the subject a pharmaceutical composition of the invention.

In another general aspect, the invention relates to a method of producing a pharmaceutical composition comprising BCMA-targeting immune cells of the invention, comprising combining BCMA-targeting immune cells with a pharmaceutically acceptable carrier to obtain the pharmaceutical composition.

The invention provides also the following non-limiting embodiments.

EMBODIMENTS

Embodiment 1 is an isolated FN3 domain, wherein the FN3 domain specifically binds to a BCMA, preferably a human BCMA.

Embodiment 2 is the isolated FN3 domain of Embodiment 1, wherein the FN3 domain specifically binds to the extracellular domain of the BCMA, such as a sequence within residues 1 to 54 of the human BCMA.

Embodiment 3 is the isolated FN3 domain of Embodiment 1, comprising an amino acid sequence that is at least 80%, 85%, 90% or 95% identical to SEQ ID NO: 1, and the FN3 domain binds to the BCMA, preferably the human BCMA, with a KD less than $1\times10^{-6}$ M, $5\times10^{-7}$ M, $1\times10^{-7}$ M, $5\times10^{-8}$ M, $1\times10^{-8}$ M, $5\times10^{-9}$ M, $1\times10^{-9}$ M, $5\times10^{-10}$ M, $1\times10^{-10}$ M, $5\times10^{-11}$ M, $1\times10^{-11}$ M, $5\times10^{-12}$ M, $1\times10^{-12}$ M, $5\times10^{-13}$ M or $1\times10^{-13}$ M as determined by using surface plasmon resonance, such as by using a biosensor system, e.g., a Proteon Instrument (BioRad).

Embodiment 4 is the isolated FN3 domain of Embodiment 1, comprising an amino acid sequence that is at least 80%, 85%, 90% or 95% identical to SEQ ID NO: 7.

Embodiment 5 is the isolated FN3 domain of Embodiment 1, comprising an amino acid sequence that is at least 90% identical to one of SEQ ID NOs: 8-44 and 58-145, preferably comprising the amino acid sequence of one of SEQ ID NOs: 8-44 and 58-145.

Embodiment 6 is an isolated polynucleotide encoding the FN3 domain of any one of Embodiments 1-5.

Embodiment 7 is a vector comprising the polynucleotide of Embodiment 6.

Embodiment 8 is host cell comprising the polynucleotide of Embodiment 6 or the vector of Embodiment 7.

Embodiment 9 is a method of producing the FN3 domain of any of Embodiments 1-5, comprising culturing the host cell comprising a nucleic acid encoding the FN3 domain under conditions to produce the FN3 domain, and recovering the FN3 domain from the cell or cell culture.

Embodiment 10 is a pharmaceutical composition comprising the FN3 domain of any of Embodiments 1-5 and a pharmaceutically acceptable carrier.

Embodiment 11 is a method of detecting a BCMA in a biological sample, comprising contacting the biological sample with the FN3 domain of any of Embodiments 1-5, and detecting the FN3 domain binding specifically to the BCMA, preferably the FN3 domain is labeled.

Embodiment 12 is a method of treating a disease associated with a BCMA in a subject in need thereof, comprising administering to the subject a therapeutically effective amount of the pharmaceutical composition of Embodiment 10.

Embodiment 13 is an isolated polynucleotide encoding a BCMA-targeting chimeric antigen receptor (CAR) comprising:
an extracellular domain having an FN3 domain that specifically binds to a BCMA;
a transmembrane domain; and
an intracellular signaling domain.

Embodiment 14 is the isolated polynucleotide of Embodiment 13, wherein the FN3 domain specifically binds to the extracellular domain of the BCMA, such as a sequence within residues 1 to 54 of the human BCMA.

Embodiment 15 is the isolated polynucleotide of Embodiment 13, wherein the FN3 domain comprises an amino acid sequence that is at least 80%, 85%, 90% or 95% identical to SEQ ID NO: 1, and the FN3 domain binds to the BCMA, preferably the human BCMA, with a KD less than $1\times10^{-6}$ M, $5\times10^{-7}$ M, $1\times10^{-7}$ M, $5\times10^{-8}$ M, $1\times10^{-8}$ M, $5\times10^{-9}$ M, $1\times10^{-9}$ M, $5\times10^{-10}$ M, $1\times10^{-10}$ M, $5\times10^{-11}$ M, $1\times10^{-11}$ M, $5\times10^{-12}$ M, $1\times10^{-12}$ M, $5\times10^{-13}$ M or $1\times10^{-13}$ M as determined by using surface plasmon resonance, such as by using a biosensor system, e.g., a Proteon Instrument (BioRad).

Embodiment 16 is the isolated polynucleotide of Embodiment 13, wherein the FN3 domain comprises an amino acid sequence that is at least 80%, 85%, 90% or 95% identical to SEQ ID NO: 7.

Embodiment 17 is the isolated polynucleotide of Embodiment 13, wherein the FN3 domain comprises an amino acid sequence that is at least 90% identical to one of SEQ ID NOs: 8-44 and 58-145, preferably comprising the amino acid sequence of one of SEQ ID NOs: 8-44 and 58-145.

Embodiment 18 is the isolated polynucleotide of any of Embodiments 13-18, wherein the CAR further comprises a hinge region that connects the extracellular domain to the transmembrane domain; preferably, the hinge region comprises an amino acid sequence that is at least 90% identical to SEQ ID NO: 3; more preferably the hinge region comprises the amino acid sequence of SEQ ID NO: 3.

Embodiment 19 is the isolated polynucleotide of any of Embodiments 13-18, wherein the CAR further comprises a signal peptide at the amino terminus; preferably, the signal peptide comprises an amino acid sequence that is at least 90% identical to SEQ ID NO: 2; more preferably the signal peptide comprises the amino acid sequence of SEQ ID NO: 2.

Embodiment 20 is the isolated polynucleotide of any of Embodiments 13-19, wherein the transmembrane domain comprises an amino acid sequence that is at least 90% identical to SEQ ID NO: 4; more preferably the transmembrane domain comprises the amino acid sequence of SEQ ID NO: 4.

Embodiment 21 is the isolated polynucleotide of any of Embodiments 13-20, wherein the intracellular signaling domain comprises a functional signaling domain derived from CD3 zeta, TCR zeta, FcR gamma, FcR beta, CD3 gamma, CD3 delta, CD3 epsilon, CD16, CD22, CD27, CD28, CD30, CD79a, CD79b, CD134 (also known as TNFRSF4 or OX-40), 4-1BB (CD137), CD278 (also known as ICOS), FcεRI, DAP10, DAP12, ITAM domains or CD66d, and the like.

Embodiment 22 is the isolated polynucleotide of any of Embodiments 13-21, wherein the intracellular signaling domain comprises a primary signaling domain and one or more co-stimulatory signaling domains.

Embodiment 23 is the isolated polynucleotide of any of Embodiments 13-22, wherein the intracellular signaling domain comprises a primary intracellular signaling domain having an amino acid sequence that is at least 90% identical to SEQ ID NO: 6; more preferably a primary intracellular signaling domain having the amino acid sequence of SEQ ID NO: 6.

Embodiment 24 is the isolated polynucleotide of any of Embodiments 13-23, wherein the intracellular signaling domain comprises a co-stimulatory intracellular signaling domain having an amino acid sequence at least 90% identical to SEQ ID NO: 5; more preferably a co-stimulatory intracellular signaling domain having the amino acid sequence of SEQ ID NO: 5.

Embodiment 25 is an isolated polynucleotide encoding a chimeric antigen receptor (CAR) comprising:
- a signal peptide having an amino acid sequence that is at least 90% identical to SEQ ID NO: 2;
- an extracellular domain comprising an FN3 domain having an amino acid sequence that is at least 80%, 85%, 90% or 95% identical to SEQ ID NO: 1, and the FN3 domain binds to the BCMA, preferably the human BCMA, with a KD less than $1 \times 10^{-6}$ M, $5 \times 10^{-7}$ M, $1 \times 10^{-7}$ M, $5 \times 10^{-8}$ M, $1 \times 10^{-8}$ M, $5 \times 10^{-9}$ M, $1 \times 10^{-9}$ M, $5 \times 10^{-10}$ M, $1 \times 10^{-10}$ M, $5 \times 10^{-11}$ M, $1 \times 10^{-11}$ M, $5 \times 10^{-12}$ M, $1 \times 10^{-12}$ M, $5 \times 10^{-13}$ M or $1 \times 10^{-13}$ M as determined by using surface plasmon resonance, such as by using a biosensor system, e.g., a Proteon Instrument (BioRad);
- a hinge region having an amino acid sequence that is at least 90% identical to SEQ ID NO: 3;
- a transmembrane domain having an amino acid sequence that is at least 90% identical to SEQ ID NO: 4; and
- an intracellular signaling domain comprising a co-stimulatory domain having an amino acid sequence that is at least 90% identical to SEQ ID NO: 5, and a primary signaling domain having an amino acid sequence that is at least 90% identical to SEQ ID NO: 6.

Embodiment 26 is an isolated polynucleotide encoding a chimeric antigen receptor (CAR) comprising:
- a signal peptide having an amino acid sequence that is at least 90% identical to SEQ ID NO: 2;
- an extracellular domain comprising an FN3 domain having an amino acid sequence that is at least 80%, 85%, 90% or 95% identical to SEQ ID NO: 7, preferably the FN3 domain comprises the amino acid sequence of SEQ ID NO: 7, wherein the FN3 binds a BCMA specifically;
- a hinge region having an amino acid sequence that is at least 90% identical to SEQ ID NO: 3;
- a transmembrane domain having an amino acid sequence that is at least 90% identical to SEQ ID NO: 4; and
- an intracellular signaling domain comprising a co-stimulatory domain having an amino acid sequence that is at least 90% identical to SEQ ID NO: 5, and a primary signaling domain having an amino acid sequence that is at least 90% identical to SEQ ID NO: 6.

Embodiment 27 is an isolated polynucleotide encoding a chimeric antigen receptor (CAR) comprising:
- a signal peptide having an amino acid sequence that is at least 90% identical to SEQ ID NO: 2;
- an extracellular domain comprising an FN3 domain having an amino acid sequence that is at least 90% identical to one of SEQ ID NOs: 8-44 and 58-145, wherein the FN3 binds a BCMA specifically;
- a hinge region having an amino acid sequence that is at least 90% identical to SEQ ID NO: 3;
- a transmembrane domain having an amino acid sequence that is at least 90% identical to SEQ ID NO: 4; and
- an intracellular signaling domain comprising a co-stimulatory domain having an amino acid sequence that is at least 90% identical to SEQ ID NO: 5, and a primary signaling domain having an amino acid sequence that is at least 90% identical to SEQ ID NO: 6.

Embodiment 28 is the isolated polynucleotide of Embodiment 27, wherein:
- the signal peptide has the amino acid sequence of SEQ ID NO: 2;
- the extracellular domain has the amino acid sequence of one of SEQ ID NOs: 8-44 and 58-145;
- the hinge region has the amino acid sequence of SEQ ID NO: 3;
- the transmembrane domain has the amino acid sequence of SEQ ID NO: 4; and
- the intracellular signaling domain comprises the amino acid sequence of SEQ ID NO: 5 and the amino acid sequence of SEQ ID NO: 6.

Embodiment 29 is an isolated polynucleotide encoding a chimeric antigen receptor (CAR).

Embodiment 30 is a vector comprising the polynucleotide of any of Embodiments 13-29, preferably an expression vector comprising a promoter operably linked to the polynucleotide of any of Embodiments 13-29.

Embodiment 31 is a host cell comprising the polynucleotide of any of Embodiments 13-29, or the vector of Embodiment 30.

Embodiment 32 is an isolated cell membrane of the host cell of Embodiment 31.

Embodiment 33 is a method of preparing an isolated cell membrane, comprising:
culturing the host cell of Embodiment 31 under conditions to produce the CAR, and
isolating the cell membrane from the host cell.

Embodiment 34 is an engineered immune cell comprising the polynucleotide of any of Embodiments 13-29 or the vector of Embodiment 30, wherein the polynucleotide of any of Embodiments 13-29 is operably linked to a promoter.

Embodiment 35 is the engineered immune cell of Embodiment 34, wherein the immune cell is an engineered T cell receptor knockout immune cell.

Embodiment 36 is the engineered immune cell of Embodiment 34 or 35, wherein the immune cell further expresses a second CAR having an extracellular domain that specifically binds to a second target different from the BCMA.

Embodiment 37 is the engineered immune cell of Embodiment 36, wherein the second target is a target associated with multiple myeloma, such as, CD19, CD20, CS-1, kappa light chain, CD138, Lewis Y antigen, CD38, or the like.

Embodiment 38 is the engineered immune cell of Embodiment 36, wherein the second target is a target expressed on normal cells but not on cancer cells, and the second CAR comprises an intracellular domain having an inhibitory receptor signaling domain.

Embodiment 39 is the engineered immune cell of any of Embodiment 34-38, wherein the cell is resistant to at least one anti-cancer chemotherapy.

Embodiment 40 is the engineered immune cell of Embodiment 39, wherein the cell further expresses one or more drug resistance genes, such as that selected from the group consisting of dihydrofolate reductase (DHFR), a mutant or modified form of ionisine-5'-monophosphate dehydrogenase II (IMPDH2), multidrug resistance protein 1 (MDR1), calcineurin, methylguanine transferase (MGMT), microRNA-21, the antibiotic resistance genes ble and mcrA, and the like.

Embodiment 41 is the engineered immune cell of Embodiment 39, wherein the cell further expresses one or more inactivated genes that are responsible for the cell's sensitivity to the drug, such as inactivated genes selected from the group consisting of CD52, glucocorticoid receptors, CD3, human hypoxanthine-guanine phosphoribosyl transferase (HPRT), human deoxycytidine kinase (dCK), and the like.

Embodiment 42 is a pharmaceutical composition, comprising an engineered immune cell of any of Embodiments 34-41 and a pharmaceutically acceptable carrier.

Embodiment 43 is a method of treating a B cell-related condition in a subject in need thereof, comprising administering to the subject a therapeutically effective amount of the pharmaceutical composition of Embodiment 42.

Embodiment 44 is the method of Embodiment 43, wherein the B cell-related condition is cancer or malignancy, or a precancerous condition chosen from one or more of a myelodysplasia, a myelodysplastic syndrome or a preleukemia.

Embodiment 45 is the method of Embodiment 43, wherein the B cell-related condition is an acute leukemia chosen from one or more of B-cell acute lymphoid leukemia (BALL), T-cell acute lymphoid leukemia (TALL), acute lymphoid leukemia (ALL); chronic myelogenous leukemia (CML), chronic lymphocytic leukemia (CLL); B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia; a prostate cancer, pancreatic cancer, lung cancer; or a plasma cell proliferative disorder, monoclonal gammapathy of undetermined significance (MGUS), Waldenstrom's macroglobulinemia, a plasmacytoma, systemic amyloid light chain amyloidosis, and POEMS syndrome, or a combination thereof.

Embodiment 46 is the method of Embodiment 45, wherein the B cell-related condition is multiple myeloma, such as the multiple myeloma selected from the group consisting of overt multiple myeloma, smoldering multiple myeloma, plasma cell leukemia, non-secretory myeloma, IgD myeloma, osteosclerotic myeloma, solitary plasmacytoma of bone, and extramedullary plasmacytoma, or a combination thereof.

Embodiment 47 is the method of Embodiment 43 to 46, further comprising administering to the subject another treatment, such as a chemotherapy, a lympho-depleting therapy, a radiation therapy, another immune-oncology drug, a targeted therapy, or another anticancer drug.

Embodiment 48 is a method of engineering an immune cell, comprising: (a) providing an immune cell; and (b) introducing into the cell the polynucleotide of any of Embodiments 13-29, or the vector of Embodiment 30.

Embodiment 49 is a method of producing a pharmaceutical composition, comprising combining the engineered immune cells of any of Embodiments 34-41 with a pharmaceutically acceptable carrier to obtain the pharmaceutical composition.

Embodiment 50 is a use of the polynucleotide of any of Embodiments 13-29, the vector of Embodiment 30, the engineered immune cells of any of Embodiments 34-41, or the pharmaceutical composition of Embodiment 42 for manufacturing a medicament for the treatment of a B cell-related condition in a subject in need thereof, preferably, the B cell-related condition is multiple myeloma.

Embodiment 51 is the polynucleotide of any of Embodiments 13-29, the vector of Embodiment 30, the engineered immune cells of any of Embodiments 34-41, or the pharmaceutical composition of Embodiment 42 for treating a B cell-related condition in a subject in need thereof, preferably, the B cell-related condition is multiple myeloma.

EXAMPLES

The following examples of the invention are to further illustrate the nature of the invention. It should be understood that the following examples do not limit the invention and that the scope of the invention is to be determined by the appended claims.

Example 1—Panning of FN3 Domain Libraries Against Recombinant BCMA Proteins by CIS Display Two constructs for BCMA recombinant protein target antigen were purchased from AB Biosciences. One was BCMA protein alone (catalog #P011Xp), and the other was BCMA fused to the Fc domain of mouse IgG2a (catalog #P001F).

FN3 Domain CIS-Display Library Selection

CIS-display was used to select BCMA-binding FN3 domains from the TCL18, TCL19, TCL21, TCL23, and TCL24 libraries.

TCL19, TCL21 and TCL23 Tencon libraries (SEQ ID NO: 46) are randomized at positions within the C and F strands and within the CD and FG loops, with the distribution of amino acids occurring at these positions as shown in Table 2. TCL19 and TCL21 were designed to include an equal distribution of 18 natural amino acids at every position (5.55% of each), excluding only cysteine and methionine. TCL23 was designed such that each randomized position approximates the amino acid distribution found in the CDR-H3 loops of functional antibodies (Birtalan et al., J Mol Biol. 2008 Apr. 11; 377(5):1518-28), with cysteine and methionine excluded. The TCL24 Tencon library (SEQ ID NO: 47) was designed to include four additional randomized Tencon positions, as compared to libraries TCL19, TCL21, and TCL23. These positions include N46 and T48 from the D strand and S84 and I86 from the G strand. These positions were chosen because the side chains of these residues are surface-exposed from the D and G beta-strands, and they lie structurally adjacent to the randomized portions of the C and F strands, thus increasing the surface area accessible for binding to target proteins. The amino acid distribution used at each position for TCL24 is identical to that described for TCL19 and TCL21 in Table 2.

TABLE 2

| Amino Acid | Amino acid frequency (%) at each randomized position for the Tencon libraries | | | |
|---|---|---|---|---|
| | TCL19 | TCL21 | TCL23 | TCL24 |
| Ala | 5.6 | 5.6 | 6.0 | 5.6 |
| Arg | 5.6 | 5.6 | 6.0 | 5.6 |
| Asn | 5.6 | 5.6 | 3.9 | 5.6 |
| Asp | 5.6 | 5.6 | 7.5 | 5.6 |
| Cys | 0.0 | 0.0 | 0.0 | 0.0 |
| Gln | 5.6 | 5.6 | 1.5 | 5.6 |
| Glu | 5.6 | 5.6 | 2.5 | 5.6 |
| Gly | 5.6 | 5.6 | 15.0 | 5.6 |
| His | 5.6 | 5.6 | 2.3 | 5.6 |
| Ile | 5.6 | 5.6 | 2.5 | 5.6 |
| Leu | 5.6 | 5.6 | 5.0 | 5.6 |
| Lys | 5.6 | 5.6 | 1.5 | 5.6 |
| Met | 0.0 | 0.0 | 0.0 | 0.0 |
| Phe | 5.6 | 5.6 | 2.5 | 5.6 |

TABLE 2-continued

| | Amino acid frequency (%) at each randomized position for the Tencon libraries | | | |
|---|---|---|---|---|
| Amino Acid | TCL19 | TCL21 | TCL23 | TCL24 |
| Pro | 5.6 | 5.6 | 4.0 | 5.6 |
| Ser | 5.6 | 5.6 | 10.0 | 5.6 |
| Thr | 5.6 | 5.6 | 4.5 | 5.6 |
| Trp | 5.6 | 5.6 | 4.0 | 5.6 |
| Tyr | 5.6 | 5.6 | 17.3 | 5.6 |
| Val | 5.6 | 5.6 | 4.0 | 5.6 |

The TCL18 Tencon library (SEQ ID NO: 48) is randomized within the BC and FG loops, and it comprises a combination of randomized BC loop lengths, from 6 to 9 residues, and randomized FG loop lengths, from 7 to 12 residues.

For in vitro transcription and translation (ITT), 3 µg of library DNA were incubated with 0.1 mM complete amino acids, 1×S30 premix components, and 15 µL of S30 extract (Promega) in a total volume of 50 µL and incubated at 30° C. After 1 hour, 375 µL of blocking solution (lx TBS pH 7.4, 2% BSA, 100 ug/ml herring sperm DNA) were added and the reactions were incubated on ice for 15 minutes. The ITT reactions were incubated with biotinylated recombinant BCMA protein fused to the Fc domain of mouse IgG2a (AB Biosciences, catalog #P011F). A competition binding assay with 4 uM mouse IgG2a (CNTO1037) was performed to enrich for FN3 domains that specifically bind BCMA instead of mouse Fc.

The biotinylated recombinant protein and the bound library members were captured on neutravidin- or streptavidin-coated magnetic beads. Unbound library members were removed by successive washes with TBST and TBS. After washing, DNA was eluted from the target protein by heating to 85° C. for 10 minutes and amplified by PCR for further rounds of panning. High-affinity binders were isolated by successively lowering the concentration of target BCMA-mFc protein during each round from 400 nM to 100 nM and increasing the washing stringency. Five successive rounds of selection were performed.

Off-Rate Selection

Outputs from the fifth round of selection were subjected to four rounds of off-rate selection. The ITT reactions were incubated with biotinylated recombinant BCMA extracellular domain protein fused to the Fc of mouse IgG2a. The concentration of the biotinylated target protein was successively lowered from 25 nM in the first two rounds to 2.5 nM in the last two rounds to select for FN3 domains with increased affinity of the FN3 domains to the target protein. A competition binding assay with 2.5 uM mouse IgG2a (CNTO1037) was performed to enrich for FN3 domains that specifically bind BCMA instead of mouse Fc.

The biotinylated target protein and the bound library members were captured on neutravidin- or streptavidin-coated magnetic beads, and washed extensively with TBST. The bound complexes were then washed with 5 uM cold recombinant BCMA-mFc proteins for 1 hour to and washed successively with TBST and TBS before the DNA was eluted to select for FN3 domains with slower dissociation rates.

Panning Round 5 Cloning

Outputs from panning were Infusion-cloned into a pET15b vector and transformed into BL21 (DE3) Gold competent cells. Single colonies were picked using an automated colony picker and grown in 2 mL 96-well plates in Luria Broth +100 ug/mL Ampicillin for 6 hours. Bacterial growths were used to inoculate cultures in Terrific Broth+100 ug/mL Ampicillin+Auto-induction media. After 24 hours, bacteria were pelleted by centrifugation and lysed with Bugbuster HT+0.2 mg/mL Lysozyme (Sigma).

Panning Round 5 Screening

Nunc maxisorp plates were coated with 5 ug/mL Neutravidin in PBS at 100 uL/well overnight. The following day, plates were washed using BioTek platewasher (3×300 uL TBST), and blocked with StartingBlock T20 (Thermo) for 1 hour. Plates were washed with 3×300 uL TBST. Antigens (1 ug/mL bt-BCMA, 1 ug/mL bt-BCMA-mFc, or 5 ug/mL CNTO1037 control), were coated in 100 uL StartingBlock T20 per well for 1 hour.

Fresh bacterial lysates were prepared and added to the ELISA plates at a 1:5 dilution for 1 hour. The plates were then washed once more, and 100 uL of anti-Tencon25 antibody pAb25-HRP were added at a 1:5000 dilution for 1 more hour. Plates were washed one final time, and 50 uL of POD Substrate (Roche) was added to each plate at a 1:100 dilution, one at a time before reading the luminescence on a Spectramax M5 plate reader.

Signal (S) over background (B) was analyzed in 3DX, and clones with less than 10-fold S/B and Relative Luminescence Units (RLU) less than 50,000 were discarded. A total of 7 hits were identified using the bt-BCMA antigen without the Fc tag, while 281 hits were identified using bt-BCMA-mFc. After sequence analysis, 142 unique sequences were identified.

Panning Round 9 Cloning

Outputs from panning were Infusion-cloned into pD444-CH vector and transformed into BL21 (DE3) Gold competent cells. Single colonies were picked using an automated colony picker and grown in 2 mL 96-well plates in Luria Broth +100 ug/mL Ampicillin for 6 hours. Bacterial growths were used to inoculate cultures in Terrific Broth+100 ug/mL Ampicillin+Auto-induction media. After 24 hours, bacteria were pelleted by centrifugation and lysed with Bugbuster HT+0.2 mg/mL Lysozyme (Sigma).

Pan 290 Round 9 Screening

Outputs were screened using the methods described above for R5, except that a 10,000-fold lysate dilution was used, and only the bt-BCMA-mFc (1 ug/mL) and bt-CNTO1037 (2 ug/mL) antigens were used. Clones with less than 10-fold S/B at this dilution were discarded. A total of 145 hits were identified and sequenced. After sequence analysis, 77 unique sequences were identified (see, e.g., SEQ ID NOs: 8-44 and 58-145).

Example 2—Screening of BCMA-Specific FN3 Domains for Binding to HEK293F Cells Transiently Expressing Human BCMA Cell counts and cell viability of hBCMA-expressing HEK293F and Mock HEK293F cells were measured, and 25×10$^6$ of each cell type were spun down at 175 g for 5 min. The media was aspirated and replaced with 25 mL FACS buffer. 100,000 cells were seeded per well in two V-bottom 96-well plates per cell type, and the plates were kept on ice throughout the experiment. The samples were set up as follows:

hBCMA cells; 2 uM treatment
hBCMA cells; 0.2 uM treatment
Mock cells; 2 uM treatment
Mock cells; 0.2 uM treatment Positive and negative antibody controls were included. 12.5 uL of control antibodies were added to 238.5 uL FACS buffer to achieve 5 uL antibody (2.5 ug) per 100 uL treatment volume. Buffer controls were also included. The buffer control wells contained only 250 uL FACS buffer.

The plates were spun at 1200 rpm for 5 min at 4° C. to pellet the cells. Buffer was discarded by inverting the plates, and 100 uL of diluted FN3 domain or control were added to the cells and mixed by pipette. Some residual liquid remained in the wells after inverting the plates, but the amount was fairly consistent among wells.

The plates were incubated on ice for 1 hr. Afterwards, cells were collected from 4 wells of one of the "Mock; 2 uM treatment" plates to check cell count and viability using Trypan blue on the Vi-Cell system. The cell count was about 75,000/well at >90% viability.

After 1 hr, the plates were spun at 1200 rpm for 5 min at 4° C. to pellet the cells. Buffer was discarded by inverting the plates, and 100 uL FACS buffer were added to the wells. The FACS buffer wash was repeated two more times. The plates were spun at 1200 rpm for 5 min at 4° C. to pellet the cells, and buffer was discarded by inverting the plates.

50 uL secondary antibody in FACS buffer was added to the wells. Anti-His mAb was added at a 1/100 dilution to all of the wells except the secondary antibody control wells, to which anti-Mouse mAb was added at a 1/1000 dilution, or the buffer control wells. The plates were incubated on ice for 1 hr. Afterwards, cells were collected from 4 wells of one of the "Mock; 2 uM treatment" plates to check cell count and viability using Trypan blue on the Vi-Cell system. The cell count was about 67,000/well at 96% viability.

After 1 hr, the plates were spun at 1200 rpm for 5 min at 4° C. to pellet the cells. Buffer was discarded by inverting the plates, and 100 uL FACS buffer were added to the wells. The FACS buffer wash was repeated two more times. The plates were spun at 1200 rpm for 5 min at 4° C. to pellet the cells, and buffer was discarded by inverting the plates.

Cells were resuspended in 30 uL Intellicyt buffer (FACS buffer, 0.1% Pluronic Acid, 1 mM EDTA, SytoX Red Live/Dead Stain at a 1:1000 dilution) and mixed well to break up lumps. The plates were kept on ice and read on an Intellicyt plate reader. Cells were gated in the following order: (a) cells, (b) single cells, (c) viable cells. The Geometric Mean of Alexa 488 channel was calculated, and the percentage of viable cells was calculated. Data was collected on a table with the ratio of hBCMA/Mock Alexa 488 signal used as a reference end-point. Based on the data, 14 BCMA-specific FN3 domains were selected for further analysis.

Example 3—Dose Response Curve (DRC) Assessment of Anti-BCMA FN3 Domains for Binding to HEK293F Cells Transiently Expressing Human BCMA Ten 3-fold dilutions of FN3 domains were titrated in BD FACS buffer, with a starting concentration of 5 uM. Control samples were diluted in FACS buffer. Source plates, each with 7 FN3 domains in single-point dose titrations, were generated alongside a non-specific Tencon25 control for overlay onto HEK293F cells transiently expressing human BCMA. The assay controls included:
A Tencon25 dose-response curve series on each plate to measure non-specific binding;
Untreated cells stained with anti-His Alexa-488 to measure non-specific labeling;
Untreated cells with no anti-His antibody staining to measure absolute background;
A positive control of 1 uM of the FN3 domain referred to as 'G10' was used as a reference to control for plate-to-plate variability in signal intensity; and Viability testing wells to troubleshoot apparent low viability.

Cell counts and cell viability of hBCMA-expressing HEK293F cells were measured, and $45 \times 10^6$ hBCMA-expressing cells were spun down at 175 g for 5 min. The media was aspirated and replaced with 25 mL FACS buffer. 100,000 cells were seeded per well in four V-bottom 96-well plates, and the plates were kept on ice throughout the experiment. $5 \times 10^6$ cells not used for plating were kept on ice for later comparison viability testing.

The plates were spun at 1200 rpm for 5 min at 4° C. to pellet the cells. Buffer was discarded by inverting the plates, and 60 uL of diluted FN3 domain or control were added to cells and mixed gently by vortexing the plates.

The plates were incubated on ice for 1 hr. After 1 hr, the plates were spun at 1200 rpm for 5 min at 4° C. to pellet the cells. Buffer was discarded by inverting the plates, and 100 uL FACS buffer were added to the wells. The FACS buffer wash was repeated two more times. The plates were spun at 1200 rpm for 5 min at 4° C. to pellet the cells, and buffer was discarded by inverting the plates. The cells were mixed gently by vortexing the plates.

50 uL secondary antibody in FACS buffer was added to the wells. Anti-His mAb was added at a 1/100 dilution to all of the wells except for the FACS buffer only negative control wells. The plates were incubated on ice for 1 hr. Afterwards, cells were collected and combined from two wells from all four plates to check cell count and viability using Trypan blue on the Vi-Cell system. The cell count was about 67,500/well at 96.6% viability. The cell count of the control cells that were kept on ice for comparison was $1 \times 10^6$/mL at 95.1% viability.

After 1 hr of staining, the plates were spun at 1200 rpm for 5 min at 4° C. to pellet the cells. Buffer was discarded by inverting the plates, and 100 uL FACS buffer were added to the wells. The FACS buffer wash was repeated two more times. The plates were spun at 1200 rpm for 5 min at 4° C. to pellet the cells, and buffer was discarded by inverting the plates.

Figure 2:
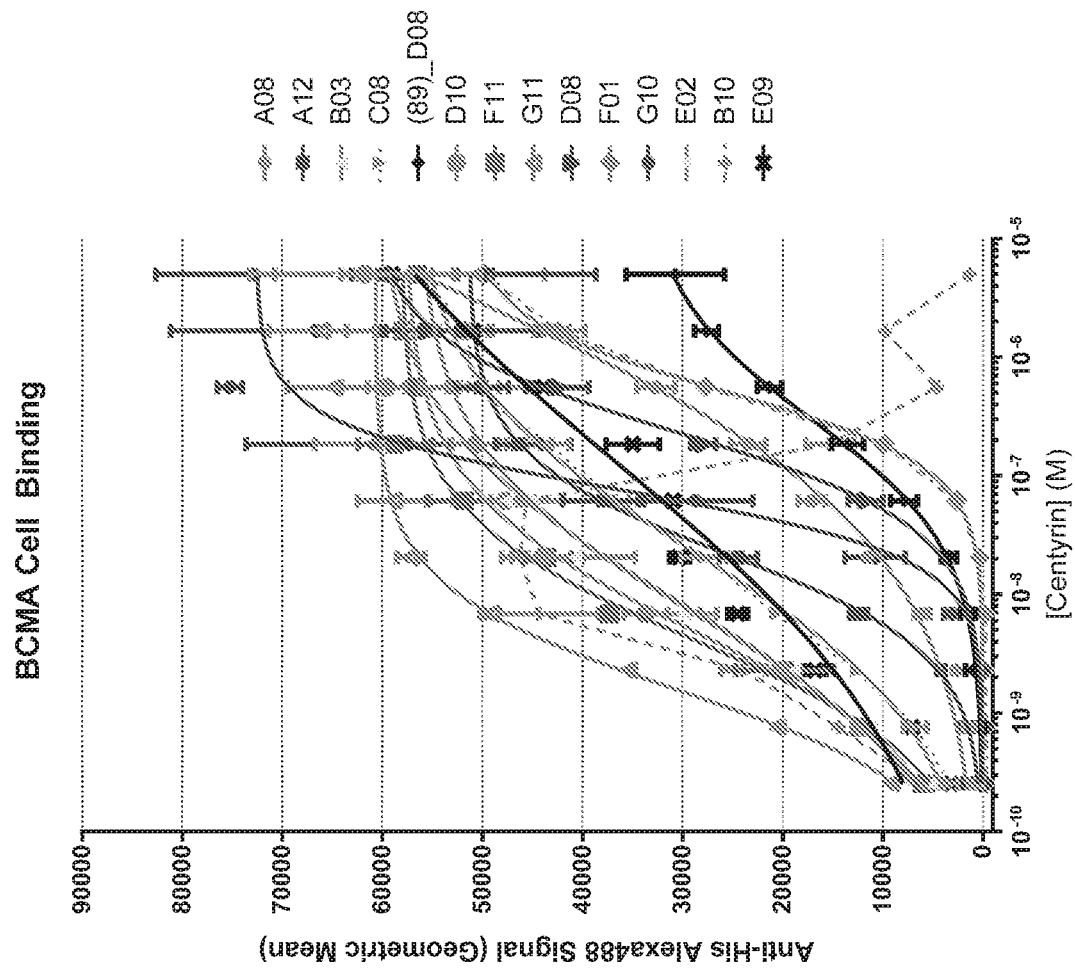
FIG. 2 shows the normalized and calibrated data from a dose response curve (DRC) assessment of anti-BCMA FN3 domains according to embodiments of the invention for binding to HEK293F cells transiently expressing human BCMA, the data were subject to PRISM curve fit analysis, with binding-saturation, one-site, specific binding.

Cells were resuspended in 30 uL Intellicyt buffer (FACS buffer, 0.1% Pluronic Acid, 1 mM EDTA, SytoX Red Live/Dead Stain at a 1:1000 dilution) and mixed gently by vortexing the plates. The plates were kept on ice and read on an Intellicyt plate reader. Cells were gated in the following order: (a) cells, (b) single cells, (c) viable cells. The Geometric Mean of Alexa 488 channel was calculated, and the percentage of viable single cells was calculated. The results with normalized and calibrated data are shown in FIG. 2 (PRISM curve fit analysis, using the binding-saturation, one-site specific binding curve-fitting program) and Table 3, which shows the Bmax and dissociation constant (Kd) that were calculated using the PRISM software.

TABLE 3

| Sample | Bmax | Kd |
|---|---|---|
| G11 | 60,715 | 1.60E−09 |
| F11 | 58,152 | 4.20E−09 |
| D10 | 57,767 | 4.90E−09 |
| E02 | 56,654 | 6.50E−09 |
| B03 | 60,866 | 8.70E−09 |
| A12 | 51,406 | 2.20E−08 |
| C08 | 57,883 | 2.30E−08 |
| G10 | 72,596 | 7.60E−08 |
| E09 | 73,558 | 1.30E−07 |
| D08 | 61,169 | 2.30E−07 |
| (89)-D08 | 34,158 | 3.00E−07 |
| F01 | 51,610 | 5.20E−07 |
| A08 | 101,024 | 3.00E−06 |

Example 4—Generation of BCMA-Specific FN3 Domain-Containing CARs

Twenty-three BCMA-specific FN3 domains (SEQ ID NOs: 8-19 and 58-68) were selected from the list of 125 (SEQ ID NOs: 8-44 and 58-145) to be engineered into CAR constructs according to the domain structure shown in FIG. 1.

The amino acid sequences for the components of the BCMA-targeting CAR constructs were as shown in Table 4:

TABLE 4

| Domain | Sequence |
|---|---|
| human CD8 signal peptide | SEQ ID NO: 2<br>MALPVTALLLPLALLLHAARP |
| human CD8 hinge | SEQ ID NO: 3<br>TTTPAPRPPTPAPTIASQPLSLRPEACRPAAGGAVHTRGLDFACDIY |
| extracellular BCMA-specific FN3 domain | SEQ ID NO: 8 (B03)<br>MLPAPKNLVVSRITEDSARLSWTAPDAAFDSFPIRYIETLIWGEAI<br>WLDVPGSERSYDLTGLKPGTEYTVVIDGVKGGGRSQPLVATFTT<br><br>SEQ ID NO: 9 (E02)<br>MLPAPKNLVVSRVTEDSARLSWTAPDAAFDSFVIVYSEPDVCGEA<br>IVLTVPGSERSYDLTGLKPGTEYWVRIAGVKGGDFSRPLSAIFTT<br><br>SEQ ID NO: 10 (G10)<br>MLPAPKNLVVSRVTEDSARLSWIAPDAAFDSFIIVYRENIETGEAI<br>VLTVPGSERSYDLTGLKPGTEYYVQIAGVKGGNISFPPLSAIFTT<br><br>SEQ ID NO: 11 (F11)<br>MLPAPKNLVVSRVTEDSARLSWTAPDAAFDSFPIRYIETLIWGEAI<br>WLDVPGSERSYDLTGLKPGTEYVVVIDGVKGGDHSKPLVATFTT<br><br>SEQ ID NO: 12 (C08)<br>MLPAPKNLVVSRITEDSARLSWTAPDAAFDSFPIRYIETLIWGEAI<br>WLYVPGSERSYDLTGLKPGTEYTVVISGVKGGESSYPLIAAFTT<br><br>SEQ ID NO: 13 (D08)<br>MLPAPKNLVVSHVTEDSARLSWTAPDAAFDSFIIVYRENIETGEAI<br>VLTVPGSERSYDLTDLKPGTEYYVQIAGVKGGNISFPPLSAIFTT<br><br>SEQ ID NO: 14 (A08)<br>MLPAPKNLVVSRITEDSARLSWTAPDAAFDSFPIRYIETLIWGEAI<br>WLDVPGSERSYDLTGLKPGTEYAVVITGVKGGRFSSPLVASFTT<br><br>SEQ ID NO: 15 (F01)<br>MLPAPKNLVVSRVTEDSARLSWTAPDAAFDSFIIVYRENIETGEAI<br>VLTVPGSERSYDLTGLKPGTEYYVQIAGVKGGNISFPPLSAIFTT<br><br>SEQ ID NO: 16 (G11)<br>MLPAPKNLVVSRITEDSARLSWTAPDAAFDSFWIRYVERLVWGE<br>AIHLHVPGSERSYDLTGLKPGTEYVVVISGVKGGWESTPLVAPFT<br>T<br>SEQ ID NO: 17 (D10)<br>MLPAPKNLVVSRITEDSARLSWTAPDAAFDSFPIRYIETLIWGEAI<br>WLYVPGSERSYDLTGLKPGTEYTVVIDGVKGGGRSQPLVASFTT<br><br>SEQ ID NO: 18 (E09)<br>MLPAPKNLVVSRVTEDSARLSWTAPDAAFDSFRIRYVEVIAWGE<br>AIWLVVPGSERSYDLTGLKPGTEYVVVIDGVKGGKTSIPLIAHFTT<br><br>SEQ ID NO: 19 (A12)<br>MLPAPKNLVVSRITEDSARLSWTAPDAAFDSFTIKYIERATWGEAI<br>WLNVPGSERSYDLTGLKPGTEYVVLINGVKGPESWPLIAHFTT<br><br>SEQ ID NO: 58 (BCMS13)<br>LPAPKNLVVSRVTEDSARLSWTAPDAAFDSFKINYREEPIFGEAIV<br>LTVPGSERSYDLTGLKPGTEYQVWIDGVKGGLWSLPLSAIFTT<br><br>SEQ ID NO: 59 (BCMS14)<br>LPAPKNLVVSRVTEDSARLSWTAPDAAFDSFWIWYWETKWEGE<br>AIVLAVPGSERSYDLTGLKPGTEYNVKIFGVKGGYPSDPLSAIFTT<br><br>SEQ ID NO: 60 (BCMS15)<br>LPAPKNLVVSRVTEDSARLSWTAPDAAFDSFDIWYWEQFWFGEA<br>IVLTVPGSERSYDLTGLKPGTEYNVKIYGVKGGLPSNPLSAIFTT<br><br>SEQ ID NO: 61 (BCMS16)<br>LPAPKNLVVSRVTEDSARLSWTAPDAAFDSFLIGYWETYEGGEAI<br>VLTVPGSERSYDLTGLKPGTEYLVAIQGVKGGGYSLPLSAIFTT<br><br>SEQ ID NO: 62 (BCMS17)<br>LPAPKNLVVSRVTEDSARLSWTAPDAAFDSFTIAYWETYVDGEAI<br>VLTVPGSERSYDLTGLKPGTEYLVAIVGVKGGYTSTPLSAIFTT |

TABLE 4-continued

| Domain | Sequence |
|---|---|
| | SEQ ID NO: 63 (BCMS18)<br>LPAPKNLVVSRVTEDSARLSWTAPDAAFDFFKINYREEPIFGEAIV<br>LTVPGSERSYDLTGLKPGTEYQVWIDGVKGGLWSLPLSAIFTT |
| | SEQ ID NO: 64 (BCMS19)<br>LPAPKNLVVSRVTEDSARLSWTAPDAAFDSFGISYYEYRALGEAI<br>VLTVPGSERSYDLTGLKPGTEYYVYIQGVKGGLPSEPLSAIFTT |
| | SEQ ID NO: 65 (BCMS20)<br>LPAPKNLVVSRVTEDSARLSWTAPDAAFDSFWIEYAEIANYGEAI<br>VLTVPGSERSYDLTGLKPGTEYKVWILGVKGGYYSGPLSAIFTT |
| | SEQ ID NO: 66 (BCMS21)<br>LPAPKNLVVSRVTEDSARLSWTAPDAAFDSFWIEYWEIDHRGEAI<br>VLTVPGSERSYDLTGLKPGTEYIVFILGVKGGYYSDPLSAIFTT |
| | SEQ ID NO: 67 (BCMS22)<br>LPAPKNLVVSRVTEDSARLSWTAPDAAFDSFWIEYWEKSQAGEAI<br>VLTVPGSERSYDLTGLKPGTEYIVGIIGVKGGRYSPPLSAIFTT |
| | SEQ ID NO: 68 (BCMS23)<br>LPAPKNLVVSRVTEDSARLSWTAPDAAFDSFYIAYPETYWYGEAI<br>VLTVPGSERSYDLTGLKPGTEYQVGIQGVKGGTKSSPLSAIFTT |
| human CD8<br>TM domain | SEQ ID NO: 4<br>IWAPLAGTCGVLLLSLVITLYCK |
| human 4-1BB<br>intracellular<br>domain | SEQ ID NO: 5<br>RGRKKLLYIFKQPFMRPVQTTQEEDGCSCRFPEEEEGGCEL |
| human CD3<br>zeta<br>intracellular<br>domain | SEQ ID NO: 6<br>RVKFSRSADAPAYKQGQNQLYNELNLGRREEYDVLDKRRGRDPE<br>MGGKPRRKNPQEGLYNELQKDKMAEAYSEIGMKGERRRGKGHD<br>GLYQGLSTATKDTYDALHMQALPPR |

Primers for each of the BCMA-targeting CAR genes were synthesized for the amplification of a dsDNA PCR template including a 5' T7 promoter for mRNA synthesis. BCMA-targeting CAR mRNA was produced using the commercially available mMESSAGE mMACHINE® T7 ULTRA Transcription Kit.

Figure 3:
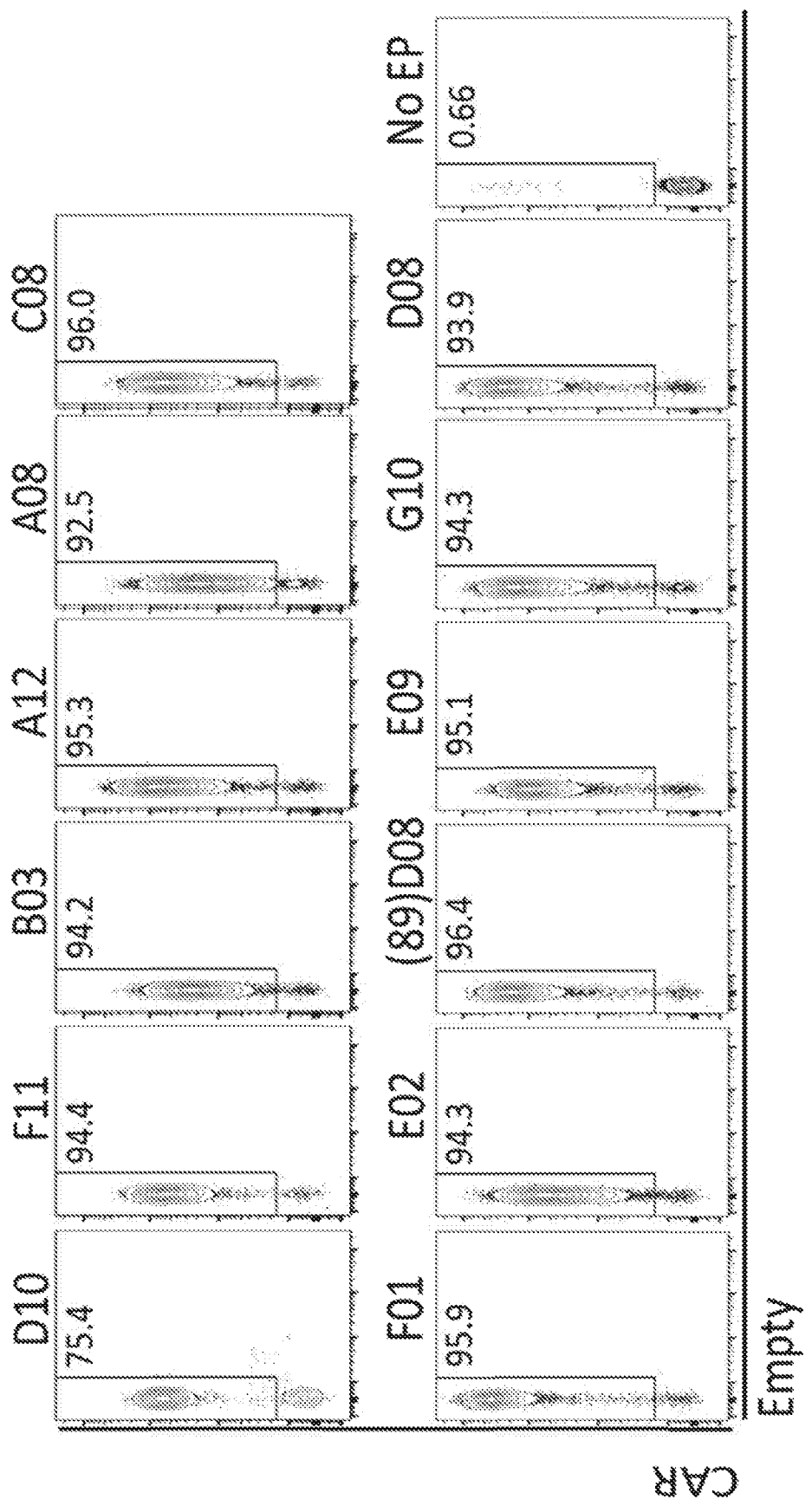
FIG. 3 shows the expression in primary T cells of BCMA-targeting CARs according to embodiments of the invention.
Figure 4:
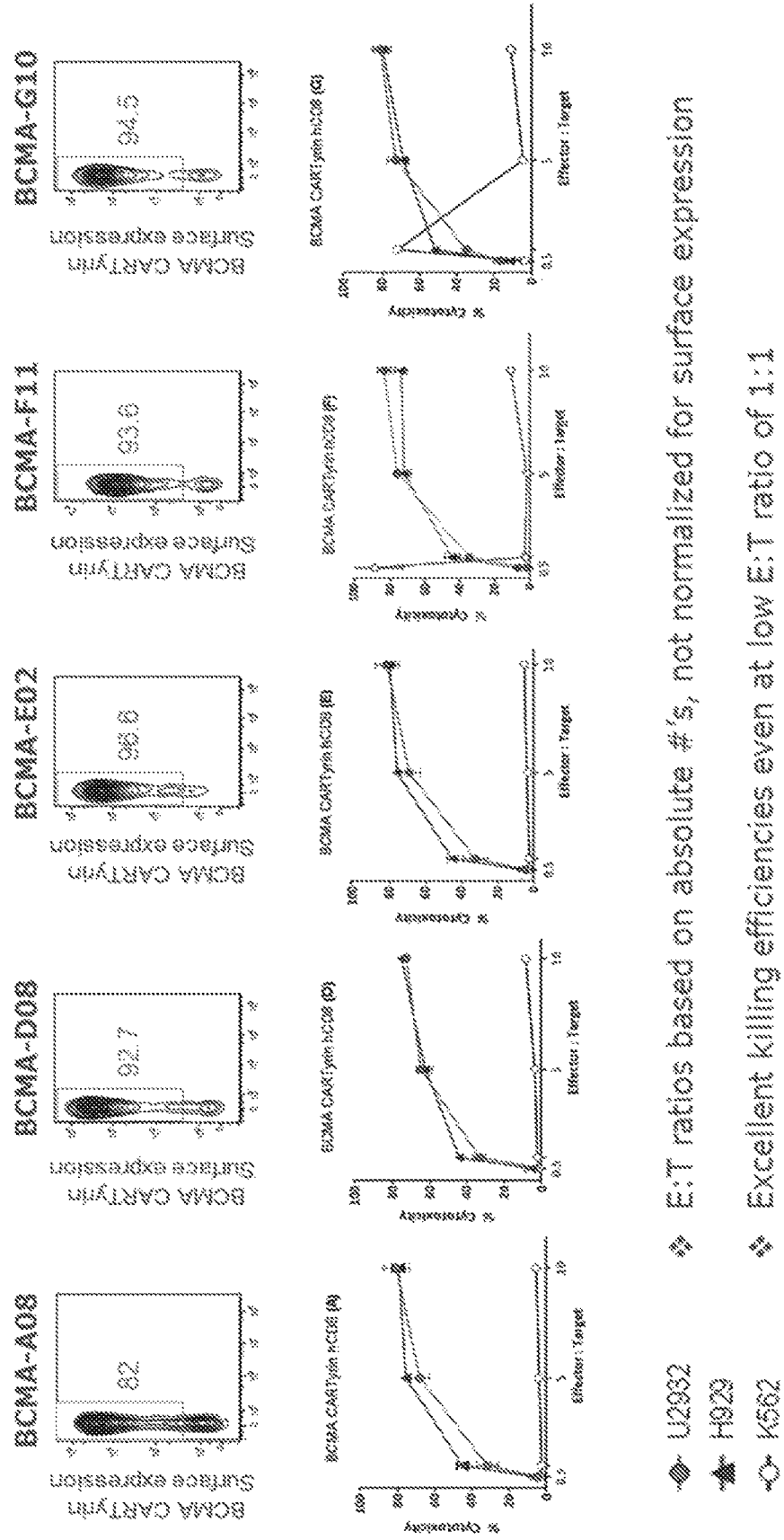
FIG. 4 shows the expression in primary T cells of BCMA-targeting CARs according to embodiments of the invention, and their specific killing of BCMA-expressing cells, where U2932 cells are CD19$^+$/BCMA$^+$, H929 cells are CD19$^-$/BCMA$^+$, and K562 cells are CD19$^-$/BCMA$^-$; and the effector:target ratio is based on absolute cell numbers, not normalized for surface expression.
Figure 5:
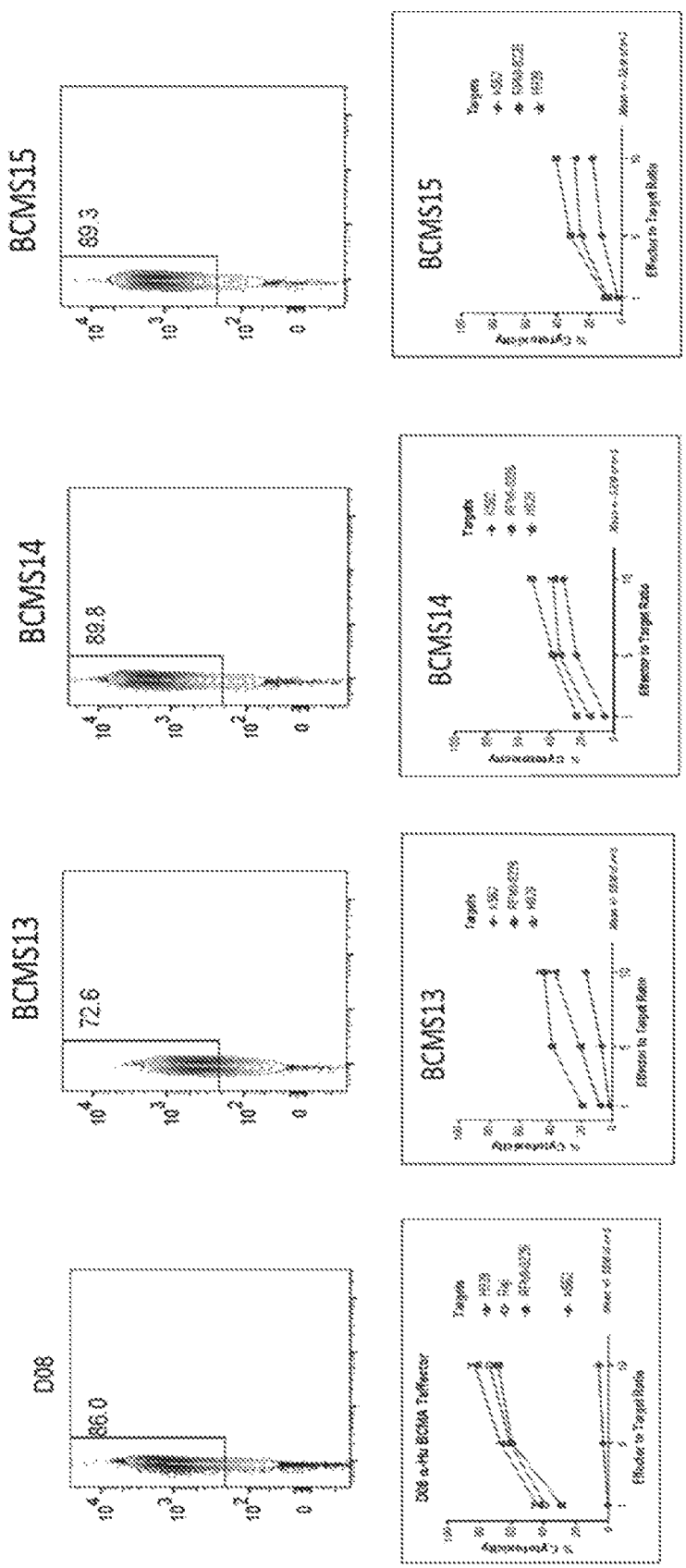
FIG. 5 shows the expression in primary T cells of BCMA-targeting CARs according to embodiments of the invention, and their specific killing of BCMA-expressing cells.
Figure 6:
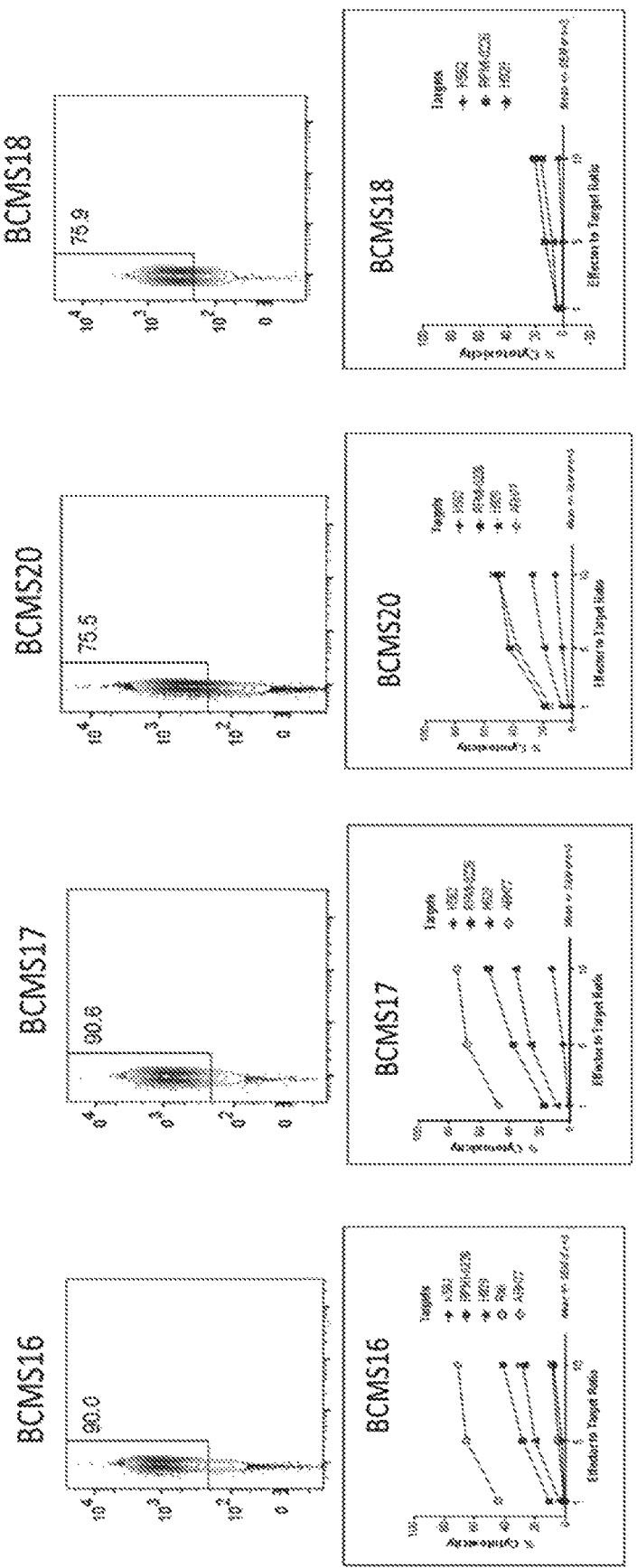
FIG. 6 shows the expression in primary T cells of BCMA-targeting CARs according to embodiments of the invention, and their specific killing of BCMA-expressing cells.
Figure 7:
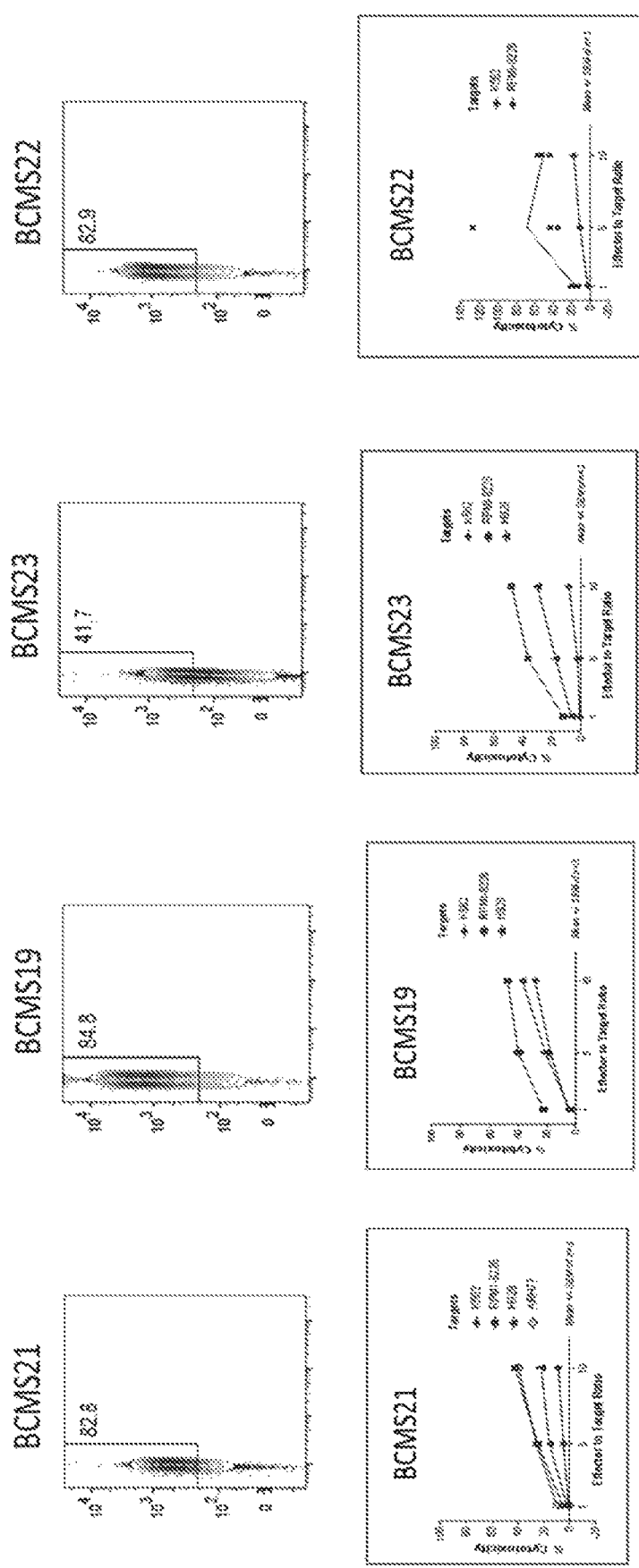
FIG. 7 shows the expression in primary T cells of BCMA-targeting CARs according to embodiments of the invention, and their specific killing of BCMA-expressing cells.

Example 5—Generation and Analysis of Engineered Immune Cells Expressing BCMA-Targeting CARs mRNA was electroporated into pan T-cells derived from normal human blood (Normal Blood Donor Service—TSRD using the ECM 830 Square Wave Electroporation System (BTX). 5×10$^6$ pan T-cells received a single electric pulse (500V, 750 us) per the manufacturer's protocol, either with or without bug of BCMA-targeting CAR mRNA. Surface expression of CARs was assessed 24 hours later using a polyclonal anti-FN3 domain Ab. The results are shown in FIG. 3.

The BCMA-targeting CAR cells were then assessed in a chromium release cytotoxicity assay.

The effectors were the BCMA-targeting CAR-expressing T cells, scFv-expressing T cells, CD19 CAR-T cells and wild type T cells. T cells underwent electroporation with the corresponding mRNAs, and approximately 90% surface expression was achieved.

The target cells used were U2932 (a CD19$^+$/BCMA$^+$ B cell lymphoma cell line), H929 (a CD19$^-$/BCMA$^+$ Plasmacytoma myeloma cell line), and K562 (a CD19$^-$/BCMA$^-$ Chronic Myeloid Leukemia cell line).

Targets were loaded with 100 uCi Cr-51 per 10×10$^6$ tumor target cells for 1 hour at 37° C. and then washed 3 times. 10,000 target cells were then incubated at the indicated ratio of engineered effector T cells to tumor target (E:T) for about 13-14 hours. The "maximal release" samples were incubated targets with Triton-X; the "no T cells, spontaneous release" samples were targets alone. Counts were collected for 60 sec, and the assay was set up in triplicate. The calculation for % cytotoxicity was as follows:

% Cytotoxicity=(experimental CPM−spontaneous release CPM)×100%/(maximal release CPM−spontaneous release CPM)

The data, shown in FIG. 4-7, was analyzed and graphed on Prism and is displayed as the mean % Cytotoxicity +/−SEM.

The results show that expression of FN3 domain-containing CARs on primary T cells can induce TAA-specific cell killing.

While the invention has been described in detail, and with reference to specific embodiments thereof, it will be apparent to one of ordinary skill in the art that various changes and modifications can be made therein without departing from the spirit and scope of the invention.

We claim:

1. An isolated fibronectin type III (FN3) domain specifically binding to a BCMA, wherein the FN3 domain has the amino acid sequence of one of SEQ ID NOs: 8-44 and 58-145.

2. An isolated fibronectin type III (FN3) domain specifically binding to a BCMA, wherein the FN3 domain has the amino acid sequence of SEQ ID NO: 13.

* * * * *